United States Patent [19]

Iimura et al.

[11] Patent Number: 4,708,955
[45] Date of Patent: Nov. 24, 1987

[54] 3-(SUBSTITUTED)PROPENYL-7-AMINO-THIAZOL-YLCEPHALOSPORANIC ACIDS AND ESTERS THEREOF

[75] Inventors: Seiji Iimura; Yoshio Abe, both of Tokyo; Jun Okumura, Yokohama; Takayuki Naito, Kawasaki; Hajime Kamachi, Chiba, all of Japan

[73] Assignee: Bristol-Myers Company, New York, N.Y.

[21] Appl. No.: 748,359

[22] Filed: Jun. 24, 1985

[51] Int. Cl.$^4$ .................. A61K 31/545; C07D 501/22; C07D 501/24
[52] U.S. Cl. ..................................... 514/202; 540/222
[58] Field of Search .......................... 544/22; 514/202; 540/222

[56] References Cited

U.S. PATENT DOCUMENTS

| | | | |
|---|---|---|---|
| 3,917,778 | 7/1976 | Cook et al. | 540/222 |
| 4,065,620 | 12/1977 | Webber | 544/16 |
| 4,307,116 | 12/1981 | Farge et al. | 540/227 |
| 4,307,230 | 12/1981 | Farge | 544/22 |
| 4,307,233 | 12/1981 | Farge et al. | 540/222 |
| 4,396,618 | 8/1983 | Heymes | 544/22 |
| 4,559,334 | 12/1985 | Takaya | 514/202 |
| 4,585,860 | 4/1986 | Takaya | 540/222 |

FOREIGN PATENT DOCUMENTS

| | | |
|---|---|---|
| 30630 | 6/1981 | European Pat. Off. |
| 53074 | 6/1982 | European Pat. Off. |
| 53537 | 6/1982 | European Pat. Off. |
| 53538 | 6/1982 | European Pat. Off. |
| 0135894 | 8/1983 | Japan ................... 544/22 |
| 1399086 | 6/1975 | United Kingdom . |

OTHER PUBLICATIONS

Dunn, J. Antimicrobial Chemotherapy, (1982), 10, Supple. C, pp. 1–10.

Primary Examiner—David M. Naff
Assistant Examiner—Robert Benson
Attorney, Agent, or Firm—Robert E. Carnahan

[57] ABSTRACT

This invention provides novel cephalosporanic acids and esters thereof having the general formula

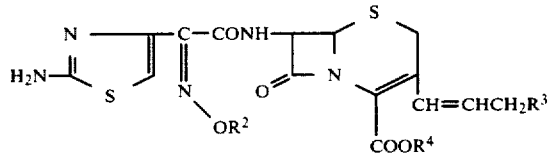

wherein
$R^2$ is hydrogen, lower alkyl, lower alkenyl, lower alkynyl, cyclo(lower)alkyl or acyl, $R^3$ is hydrogen, lower alkyl, lower alkoxy, lower alkanoyloxy, and
$R^4$ is hydrogen, pivaloyloxymethyl, acetoxymethyl, 1-acetoxyethyl, 5-methyl-2-oxo-1, 3-dioxolen-4-ylmethyl or 4-glycyloxybenzoyloxymethyl. These compounds, especially esters, are useful as broad spectrum antibiotics in the treatment and prevention of infectious diseases of mammals, and for other purposes known in the art.

62 Claims, No Drawings

3-(SUBSTITUTED)PROPENYL-7-AMINO-THIAZOL-YLCEPHALOSPORANIC ACIDS AND ESTERS THEREOF

BACKGROUND AND PRIOR ART (A) Published European Patent Application No. 30,630 discloses a vast number of 7-acylamino-3-vinyl-cephalosporanic acid derivatives including, inter alia, those of the formula

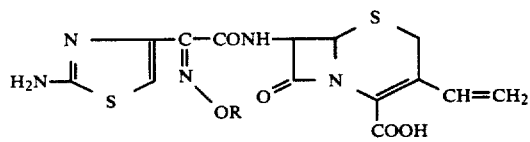

wherein R inter alia may be (lower)alkyl, (lower)alkenyl, (lower)alkynyl or carboxy(lower)alkyl. The compounds are prepared, inter alia, by reaction of the corresponding 3-halomethyl compound with a triarylphosphine, followed by treatment with a base and reaction with formaldehyde. In each case, the final 3-substituent is the vinyl group. There is no disclosure or suggestion of a propenyl or a substituted propenyl moiety for the 3-substituent. There is also no disclosure or suggestion of an ester as pro-drug for oral use referring to the 4-carboxylic acid moiety. That compound wherein R is —$CH_2CO_2H$ has been referred to in the literature as FK-027 and as cefvixim.

(B) U.K. Patent Specification No. 1,399,086 contains a generic disclosure encompassing a vast number of cephalosporins of the formula

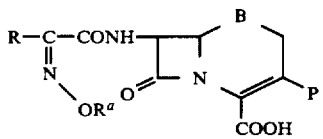

wherein R is hydrogen or an organic group, $R^a$ is an etherifying monovalent organic group linked to the oxygen through a carbon atom, B is >S or >S→O, and P is an organic group. In one embodiment, P may be inter alia a vinyl group of the formula

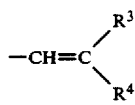

in which $R^3$ and $R^4$ independently may be hydrogen, nitrile, (lower)alkoxycarbonyl, or substituted or unsubstituted aliphatic, cycloaliphatic, araliphatic or aromatic. However, the 2-aminothiazol-4-yl group is not identified as a possible R substituent and there is no disclosure or suggestion about an ester as pro-drug for oral use concerning the 4-carboxylic acid thereof. U.S. Pat. No. 3,971,778 and its divisionals U.S. Pat. Nos. 4,024,133, 4,024,137, 4,064,346, 4,033,950, 4,079,178, 4,091,209, 4,092,477 and 4,093,803 have similar disclosures.

(C) U.S. Pat. No. 4,307,233 discloses, inter alia, 3-vinyl cephalosporin derivatives of the formula

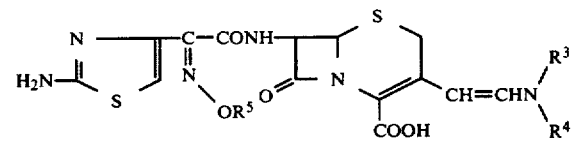

in which $R^5$ inter alia may be alkyl, vinyl, cyanomethyl or a protective group such as 2-methoxyprop-2-yl, and $R^3$ and $R^4$ are alkyl groups (optionally substituted by hydroxy, alkoxy, amino, alkylamino or dialkylamino) or phenyl groups, or $R^3$ and $R^4$, taken together with the nitrogen to which they are attached, may form a saturated heterocyclic ring of 5 or 6 members, optionally containing another heteroatom selected from N, O and S, and optionally substituted by an alkyl group. The compounds are useful as intermediates in the preparation of 3-thiovinyl cephalosporin derivatives. There is no disclosure or suggestion of a substituted or an unsubstituted propenyl moiety for the 3-substituent and also no disclosure or suggestion concerning a pro-drug ester for oral use for the 4-carboxylic acid. Published United Kingdom Patent Application No. 2,051,062 is concordant thereto and has a similar disclosure.

(D) Published European Patent Application No. 53,537 discloses, inter alia, 3-vinylcephalosporin derivatives of the formula

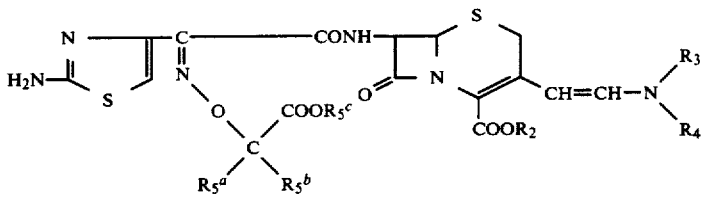

in which $R_5{}^a$ and $R_5{}^b$ are the same or different and are hydrogen or alkyl, or taken together, form an alkylene group containing 2 or 3 carbon atoms, $R_5{}^c$ is an acid protecting group, $R_2$ is an acid protecting group such as an ester, $R_3$ and $R_4$ are the same or different and are hydrogen, alkyl (optionally substituted by hydroxy, alkoxy, amino, alkylamino or dialkylamino) or phenyl groups, or $R_3$ and $R_4$, taken together with the nitrogen to which they are attached, may form a saturated heterocyclic ring of 5 or 6 members, optionally containing another heteroatom selected from N, O and S, and optionally substituted by an alkyl group. The compounds are useful as intermediates in the preparation of 3-thiovinyl cephalosporin derivatives. There is no disclosure or suggestion of a substituted or an unsubstituted propenyl group for the 3-substituent and an ester of the 4-carboxylic acid for oral use.

(E) U.S. Pat. No. 4,307,116 discloses 3-thiovinylcephalosporins of the formula

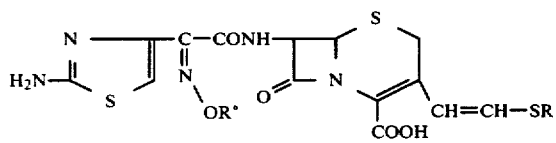

in which $R^o$ is hydrogen, alkyl, vinyl or cyanomethyl, and R inter alia may be one of a vast number of heterocyclic rings. There is no disclosure or suggestion of a substituted or an unsubstituted propenyl moiety for the 3-substituent and also there is no disclosure or suggestion of an ester thereof for oral use.

(F) Published European Patent Application No. 53,074 generically discloses a vast number of 3-vinyl-cephalosporin derivatives of the formula

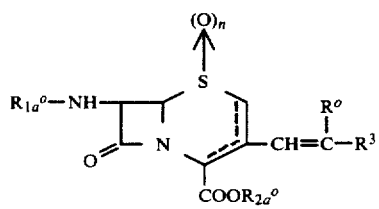

wherein $R_{1a}^o$ (in one of several embodiments) may be

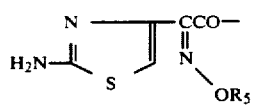

in which $R^5$ inter alia may be hydrogen, alkyl, vinyl, cyanomethyl, an oxime-protecting group such as trityl, etc., or a group of the formula

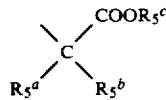

in which $R_5^a$ and $R_5^b$ are the same or different, and may be hydrogen, alkyl or, taken together, an alkylene radical of 2 or 3 carbon atoms, and $R_5^c$ is hydrogen or an acid-protecting radical; $R_{2a}^o$ is hydrogen or an acid-protecting radical such as methoxymethyl; $R^o$ (in one of several embodiments) may be a methyl group substituted by a 5- or 6-membered aromatic heterocyclic ring containing a single heteroatom, such as 2- or 3-pyridyl, 2- or 3-thienyl or 2- or 3-furyl; and $R_3$ is a group of the formula

in which $R_4$ may be alkyl, trihalomethyl or optionally substituted phenyl. These compounds are stated to be intermediates in the preparation of compounds in which the 3-substituent is a group of the formula

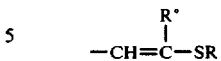

which are stated to have antibacterial activity. Although this patent includes the possibility of $R^o$ being a methyl group substituted by an N-containing heterocyclic ring, in both the intermediates and final product (thus giving a heterocyclic-substituted propenyl moiety), the reference exemplifies $R^o$ in the intermediates and final product only as methyl and further in both the intermediates and final product, the propenyl group must contain a second substituent ($-O_3SR^4$ or $-SR$ respectively). There is no disclosure or suggestion of an ester thereof for oral use.

(G) Published European Patent Application No. 53,538 discloses, inter alia, 3-vinylcephalosporin intermediates of the formula

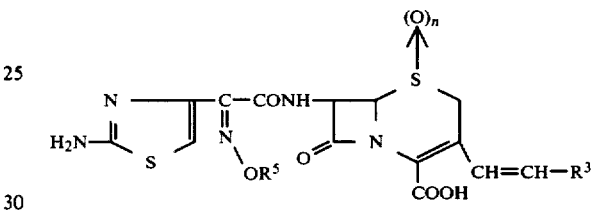

in which n is 0 or 1, $R^5$ is hydrogen, alkyl, vinyl, cyanomethyl or an oxime-protecting group, and $R^3$ is halogen.

Complete Disclosure

This application relates to novel cephalosporin derivatives which are potent antibacterial agents and some of which may be used orally. More particularly, it relates to compounds of the formula

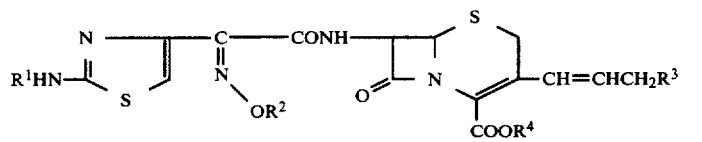

wherein
$R^1$ is hydrogen or a conventional amino-protecting group,
$R^2$ is hydrogen, a straight or branched chain alkyl having 1 to 4 carbon atoms, an alkenyl or alkynyl having 2 to 4 carbon atoms, cycloalkyl having 3 to 6 carbon atoms, or acyl having 2 to 4 carbon atoms,
$R^3$ is hydrogen, lower alkyl having 1 to 3 carbon atoms, lower alkoxy having 1 to 3 carbon atoms, lower alkanoyloxy having 2 to 3 carbon atoms, and
$R^4$ is hydrogen or physiologically hydrolyzable ester groups such as acetoxymethyl, 1-acetoxyethyl, pivaloyloxymethyl, 5-methyl-2-oxo-1,3-dioxolen-4-ylmethyl or 4-glycyloxybenzoyloxymethyl.

Also included within the scope of the invention are the pharmaceutically acceptable acid addition salts, the metal salts (when $R^4$ is H) and the solvates (including hydrates) of the compounds of Formula I, which may exist in various tautomeric forms which are also included, e.g. the 2-iminothiazolin-4-yl form of the 2-aminothiazol-4-yl moiety.

In another aspect, this application relates to a process for the preparation of the compounds of Formula I.

As shown in the structural formula, the compounds of Formula I have the "syn" or "Z" configuration with respect to the alkoxyimino group. Because the compounds are geometric isomers, some of the "anti" isomer may also be present. This invention comprises compounds of Formula I containing at least 90% of the "syn" isomer. Preferably, the compounds of Formula I are "syn" isomers which are essentially free of the corresponding "anti" isomers.

In addition to geometric isomers possible with respect to the alkoxyimino group, the compounds of Formula I (and the intermediates VIII, XII, XIII and XIV) also form geometric (cis and trans, or Z and E) isomers about the double bond of the propenyl group at the 3-position. Both the cis ("Z") and trans ("E") isomers of these compounds are specifically included within the scope of this invention.

The pharmaceutically acceptable acid addition salts of Formula I are those in which anion does not contribute significantly to the toxicity of the salt and are compatible with the customary pharmaceutical vehicles and adapted for oral or parenteral administration. The pharmaceutically acceptable acid addition salts include the salts of Formula I with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, p-toluenesulfonic acid and other acids known and used in the penicillin and cephalosporin arts. Preparation of these salts is carried out by conventional techniques involving reaction of Formula Ia with the acid in a substantially equivalent amount.

Those substances of Formula I wherein $R^4$ is hydrogen also form pharmaceutically acceptable metal and amine salts in which the cation does not contribute significantly to the toxicity or biological activity of the salt. These salts are also part of the present invention. Suitable metal salts include the sodium, potassium, barium, zinc and aluminum salts. The sodium or potassium salts are preferred. Amine salts prepared from amines used, for instance, with benzyl penicillin which are capable of forming stable salts with the acidic carboxyl group include trialkylamines such as triethylamine, procaine, dibenzylamine, N-benzyl-β-phenethylamine, 1-ephenamine, N,N'-dibenzylethylenediamine, dehydroabiethylamine, N-ethylpiperidine, benzylamine and dicyclohexylamine.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Suitable esters are the acetoxymethyl, pivaloyloxymethyl, 1-acetoxyethyl, 1-pivaloyloxyethyl, 3-phthalidyl, p-glycyloxybenzoyloxymethyl, 5-methyl-1,3-dioxacyclopent-4-en-2-on-4-ylmethyl and others known in the penicillin and cephalosporin art. The most preferred esters are 1-acetoxyethyl and pivaloyloxymethyl.

The compounds of Formula I may be formulated for oral or parenteral use in a conventional manner using known pharmaceutical carriers and excipients, and they may be presented in unit dosage form or in multiple dose containers. The compositions may be in the form of tablets, capsules, solutions, suspensions or emulsions. These compounds may also be formulated as suppositories utilizing conventional suppository bases such as cocoa butter or other fatty materials. The compounds may, if desired, be administered in combination with other antibiotics including cephalosporins, penicillins and aminoglycosides.

When provided in unit dosage forms, the compositions will preferably contain from about 50 to about 1500 mg of the active ingredient of Formula I. The dosage of the compounds of Formula I is dependent on such factors as the weight and age of the patient, as well as the particular nature and severity of the disease, and within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient.

In the compounds of Formula I, hydrogen is particularly preferred for $R^1$, hydrogen, acetyl or methyl for $R^2$ and pivaloyloxymethyl or 1-acetoxyethyl for $R^4$. The most preferred compounds of the invention are listed below, and experimental details for their preparation and characterization follow. Those which are not shown by specific example are readily prepared by analagous procedures.

(1) 7β-[(Z)-2-(2-aminothiazol-4-yl)-2-(methoxyimino)acetamido]-3-[(Z)-prop-1-en-1-yl]-3-cephem-4-carboxylic acid, (2) 1-acetoxyethyl 7β-[(Z)-2-(2-aminothiazol-4-yl)-2-(methoxyimino)acetamido]-3-[(Z)-prop-1-en-1-yl]-3-cephem-4-carboxylate, (3) pivaloyloxymethyl 7β-[(Z)-2-(2-aminothiazol-4-yl)-2-(methoxyimino)acetamido]-3-[(Z)-prop-1-en-1-yl]-3-cephem-4-carboxylate, (4) 7β-[(Z)-2-(2-aminothiazol-4-yl)-2-(methoxyimino)acetamido]-3-[(E)-prop-1-en-1-yl]-3-cephem-4-carboxylic acid, (5) 1-acetoxyethyl 7β-[(Z)-2-(2-aminothiazol-4-yl)-2-(methoxyimino)acetamido]-3-[(E)-prop-1-en-1-yl]-3-cephem-4-carboxylate, (6) pivaloyloxymethyl 7β-[(Z)-2-(2-aminothiazol-4-yl)-2-(methoxyimino)acetamido]-3-[(E)-prop-1-en-1-yl]-3-cephem-4-carboxylate, (7) 7β-[(Z)-2-(2-aminothiazol-4-yl)-2-(methoxyimino)acetamido]-3-[(Z)-but-1-en-1-yl]-3-cephem-4-carboxylic acid, (8) acetoxymethyl 7β-[(Z)-2-(2-aminothiazol-4-yl)-2-(methoxyimino)acetamido]-3-[(Z)-but-1-en-1-yl]-3-cephem-4-carboxylate, (9) 1-acetoxyethyl 7β-[(Z)-2-(2-aminothiazol-4-yl)-2-(methoxyimino)acetamido]-3-[(Z)-but-1-en-1-yl]-3-cephem-4-carboxylate,

(10) pivaloyloxymethyl 7β-[(Z)-2-(2-aminothiazol-4-yl)-2-(methoxyimino)acetamido]-3-[(Z)-but-1-en-1-yl]-3-cephem-4-carboxylate,

(11) 4-glycyloxybenzoyloxymethyl 7β-[(Z)-2-(2-aminothiazol-4-yl)-2-(methoxyimino)acetamido]-3-[(Z)-but-1-en-1-yl]-3-cephem-4-carboxylate,

(12) 7β-[(Z)-2-(2-aminothiazol-4-yl)-2-(methoxyimino)acetamido]-3-[(E)-but-1-en-1-yl]-3-cephem-4-carboxylic acid,
(13) acetoxymethyl 7β-[(Z)-2-(2-aminothiazol-4-yl)-2-(methoxyimino)acetamido]-3-[(E)-but-1-en-1-yl]-3-cephem-4-carboxylate,
(14) 1-acetoxyethyl 7β-[(Z)-2-(2-aminothiazol-4-yl)-2-(methoxyimino)acetamido]-3-[(E)-but-1-en-1-yl]-3-cephem-4-carboxylate,
(15) pivaloyloxymethyl 7β-[(Z)-2-(2-aminothiazol-4-yl)-2-(methoxyimino)acetamido]-3-[(E)-but-1-en-1-yl]-3-cephem-4-carboxylate,
(16) 4-glycyloxybenzoyloxymethyl 7β-[(Z)-2-(2-aminothiazol-4-yl)-2-(methoxyimino)acetamido]-3-[(E)-but-1-en-1-yl]-3-cephem-4-carboxylate,
(17) 7β-[(Z)-2-(2-aminothiazol-4-yl)-2-(methoxyimino)acetamido]-3-[(Z)-pent-1-en-1-yl]-3-cephem-4-carboxylic acid,
(18) 1-acetoxyethyl 7β-[(Z)-2-(2-aminothiazol-4-yl)-2-(methoxyimino)acetamido]-3-[(Z)-pent-1-en-1-yl]-3-cephem-4-carboxylate,
(19) pivaloyloxymethyl 7β-[(Z)-2-(2-aminothiazol-4-yl)-2-(methoxyimino)acetamido]-3-[(Z)-pent-1-en-1-yl]-3-cephem-4-carboxylate,
(20) 7β-[(Z)-2-(2-aminothiazol-4-yl)-2-(methoxyimino)acetamido]-3-[(E)-pent-1-en-1-yl]-3-cephem-4-carboxylic acid,
(21) 1-acetoxyethyl 7β-[(Z)-2-(2-aminothiazol-4-yl)-2-(methoxyimino)acetamido]-3-[(E)-pent-1-en-1-yl]-3-cephem-4-carboxylate,
(22) pivaloyloxymethyl 7β-[(Z)-2-(2-aminothiazol-4-yl)-2-(methoxyimino)acetamido]-3-[(E)-pent-1-en-1-yl]-3-cephem-4-carboxylate,
(23) 7β-[(Z)-2-(2-aminothiazol-4-yl)-2-(methoxyimino)acetamido]-3-[(Z)-3-methoxyprop-1-en-1-yl]-3-cephem-4-carboxylic acid,
(24) 1-acetoxyethyl 7β-[(Z)-2-(2-aminothiazol-4-yl)-2-(methoxyimino)acetamido]-3-[(Z)-3-methoxyprop-1-en-1-yl]-3-cephem-4-carboxylate,
(25) pivaloyloxymethyl 7β-[(Z)-2-(2-aminothiazol-4-yl)-2-(methoxyimino)acetamido]-3-[(Z)-3-methoxyprop-1-en-1-yl]-3-cephem-4-carboxylate,
(26) 7β-[(Z)-2-(2-aminothiazol-4-yl)-2-(methoxyimino)acetamido]-3-[(E)-3-methoxyprop-1-en-1-yl]-3-cephem-4-carboxylic acid,
(27) 1-acetoxyethyl 7β-[(Z)-2-(2-aminothiazol-4-yl)-2-(methoxyimino)acetamido]-3-[(E)-3-methoxyprop-1-en-1-yl]-3-cephem-4-carboxylate,
(28) pivaloyloxymethyl 7β-[(Z)-2-(2-aminothiazol-4-yl)-2-(methoxyimino)acetamido]-3-[(E)-3-methoxyprop-1-en-lyl]-3-cephem-4-carboxylate,
(29) 7β-[(Z)-2-(2-aminothiazol-4-yl)-2-(hydroxyimino)acetamido]-3-[(Z)-prop-1-en-1-yl]-3-cephem-4-carboxylic acid,
(30) 1-acetoxyethyl 7β-[(Z)-2-(2-aminothiazol-4-yl)-2-(hydroxyimino)acetamido]-3-[(Z)-prop-1-en-1-yl]-3-cephem-4-carboxylate,
(31) pivaloyloxymethyl 7β-[(Z)-2-(2-aminothiazol-4-yl)-2-(hydroxyimino)acetamido]-3-[(Z)-prop-1-en-1-yl]-3-cephem-4-carboxylate,
(32) acetoxymethyl 7β-[(Z)-2-(2-aminothiazol-4-yl)-2-(hydroxyimino)acetamido]-3-[(Z)-prop-1-en-1-yl]-3-cephem-4-carboxylate,
(33) 7β-[(Z)-2-(2-aminothiazol-4-yl)-2-(hydroxyimino)acetamido]-3-[(E)-prop-1-en-1-yl]-3-cephem-4-carboxylic acid,
(34) acetoxymethyl 7β-[(Z)-2-(2-aminothiazol-4-yl)-2-(hydroxyimino)acetamido]-3-[(E)-prop-1-en-1-yl]-3-cephem-4-carboxylate,
(35) 1-acetoxyethyl 7β-[(Z)-2-(2-aminothiazol-4-yl)-2-(hydroxyimino)acetamido]-3-[(E)-prop-1-en-1-yl]-3-cephem-4-carboxylate,
(36) pivaloyloxymethyl 7β-[(Z)-2-(2-aminothiazol-4-yl)-2-(hydroxyimino)acetamido]-3-[(E)-prop-1-en-1-yl]-3-cephem-4-carboxylate,
(37) 7β-[(Z)-2-(2-aminothiazol-4-yl)-2-(hydroxyimino)acetamido]-3-[(Z)-3-acetoxyprop-1-en-1-yl]-3-cephem-4-carboxylic acid,
(38) acetoxymethyl 7β-[(Z)-2-(2-aminothiazol-4-yl)-2-(hydroxyimino)acetamido]-3-[(Z)-3-acetoxyprop-1-en-1-yl]-3-cephem-4-carboxylate,
(39) 1-acetoxyethyl 7β-[(Z)-2-(2-aminothiazol-4-yl)-2-(hydroxyimino)acetamido]-3-[(Z)-3-acetoxyprop-1-en-1-yl]-3-cephem-4-carboxylate,
(40) pivaloyloxymethyl 7β-[(Z)-2-(2-aminothiazol-4-yl)-2-(hydroxyimino)acetamido]-3-[(Z)-3-acetoxyprop-1-en-1-yl]-3-cephem-4-carboxylate,
(41) 7β-[(Z)-2-(2-aminothiazol-4-yl)-2-(hydroxyimino)acetamido]-3-[(E)-3-acetoxyprop-1-en-1-yl]-3-cephem-4-carboxylic acid,
(42) acetoxymethyl 7β-[(Z)-2-(2-aminothiazol-4-yl)-2-(hydroxyimino)acetamido]-3-[(E)-3-acetoxyprop-1-en-1-yl]-3-cephem-4-carboxylate,
(43) 1-acetoxyethyl 7β-[(Z)-2-(2-aminothiazol-4-yl)-2-(hydroxyimino)acetamido]-3-[(E)-3-acetoxyprop-1-en-1-yl]-3-cephem-4-carboxylate,
(44) pivaloyloxymethyl 7β-[(Z)-2-(2-aminothiazol-4-yl)-2-(hydroxyimino)acetamido]-3-[(E)-acetoxyprop-1-en-1-yl]-3-cephem-4-carboxylate,
(45) 7β-[(Z)-2-(2-aminothiazol-4-yl)-2-(methoxyimino)acetamido]-3-[(Z)-3-acetoxyprop-1-en-1-yl]-3-cephem-4-carboxylic acid,
(46) acetoxymethyl 7β-[(Z)-2-(2-aminothiazol-4-yl)-2-(methoxyimino)acetamido]-3-[(Z)-3-acetoxyprop-1-en-1-yl]-3-cephem-4-carboxylate,
(47) 1-acetoxyethyl 7β-[(Z)-2-(2-aminothiazol-4-yl)-2-(methoxyimino)acetamido]-3-[(Z)-acetoxyprop-1-en-1-yl]-3-cephem-4-carboxylate,
(48) pivaloyloxymethyl 7β-[(Z)-2-(2-aminothiazol-4-yl)-2-(methoxyimino)acetamido]-3-[(Z)-3-acetoxyprop-1-en-1-yl]-3-cephem-4-carboxylate,
(49) 7β-[(Z)-2-(2-aminothiazol-4-yl)-2-(methoxyimino)acetamido]-3-[(E)-3-acetoxyprop-1-en-1-yl]-3-cephem-4-carboxylic acid,
(50) acetoxymethyl 7β-[(Z)-2-(2-aminothiazol-4-yl)-2-(methoxyimino)acetamido]-3-[(E)-3-acetoxyprop-1-en-1-yl]-3-cephem-4-carboxylate,
(51) 1-acetoxyethyl 7β-[(Z)-2-(2-aminothiazol-4-yl)-2-(methoxyimino)acetamido]-3-[(E)-acetoxyprop-1-en-1-yl]-3-cephem-4-carboxylate,
(52) pivaloyloxymethyl 7β-[(Z)-2-(2-aminothiazol-4-yl)-2-(methoxyimino)acetamido]-3-[(E)-3-acetoxyprop-1-en-1-yl]-3-cephem-4-carboxylate, (53) 7β-[(Z)-2-(2-aminothiazol-4-yl)-2-(acetoxyimino)acetamido]-3-[(Z)-prop-1-en-1-yl]-3-cephem-4-carboxylic acid,
(54) acetoxymethyl 7β-[(Z)-2-(2-aminothiazol-4-yl)-2-(acetoxyimino)acetamido]-3-[(Z)-prop-1-en-1-yl]-3-cephem-4-carboxylate,
(55) 1-acetoxyetnyl 7β-[(Z)-2-(2-aminothiazol-4-yl)-2-(acetoxyimino)acetamido]-3-[(Z)-prop-1-en-1-yl]-3-cephem-4-carboxylate,

(56) pivaloyloxymethyl 7β-[(Z)-2-(2-aminothiazol-4-yl)-2-(acetoxyimino)acetamido]-3-[(Z)-prop-1-en-1-yl]-3-cephem-4-carboxylate,

(57) 5-methyl-2-oxo-1,3-dioxolen-4-ylmethyl 7β-[(Z)-2-(2-aminothiazol-4-yl)-2-(acetoxyimino)acetamido]-3-[(Z)-prop-1-en-1-yl]-3-cephem-4-carboxylate,

(58) 7β-[(Z)-2-(2-aminothiazol-4-yl)-2-(acetoxyimino)acetamido]-3-[(E)-prop-1-en-1-yl]-3-cephem-4-carboxylic acid,

(59) acetoxymethyl 7β-[(Z)-2-(2-aminothiazol-4-yl)-2-(acetoxyimino)acetamido]-3-[(E)-prop-1-en-1-yl]-3-cephem-4-carboxylate,

(60) 1-acetoxyethyl 7β-[(Z)-2-(2-aminothiazol-4-yl)-2-(acetoxyimino)acetamido]-3-[(E)-prop-1-en-1-yl]-3-cephem-4-carboxylate,

(61) pivaloyloxymethyl 7β-[(Z)-2-(2-aminothiazol-4-yl)-2-(acetoxyimino)acetamido]-3-[(E)-prop-1-en-1-yl]-3-cephem-4-carboxylate,

(62) 5-methyl-2-oxo-1,3-dioxolen-4-ylmethyl 7β-[(Z)-2-(2-aminothiazol-4-yl)-2-(acetoxyimino)acetamido]-3-[(E)-prop-1-en-1-yl]-3-cephem-4-carboxylate,

(63) 7β-[(Z)-2-(2-aminothiazol-4-yl)-2-(acetoxyimino)acetamido]-3-[(Z)-3-acetoxyprop-1-en-1-yl]-3-cephem-4-carboxylic acid,

(64) acetoxymethyl 7β-[(Z)-2-(2-aminothiazol-4-yl)-2-(acetoxyimino)acetamido]-3-[(Z)-3-acetoxyprop-1-en-1-yl]-3-cephem-4-carboxylate,

(65) 1-acetoxyethyl 7β-[(Z)-2-(2-aminothiazol-4-yl)-2-(acetoxyimino)acetamido]-3-[(Z)-3-acetoxyprop-1-en-1-yl]-3-cephem-4-carboxylate,

(66) pivaloyloxymethyl 7β-[(Z)-2-(2-aminothiazol-4-yl)-2-(acetoxyimino)acetamido]-3-[(Z)-3-acetoxyprop-1-en-1-yl]-3-cephem-4-carboxylate,

(67) 5-methyl-2-oxo-1,3-dioxolen-4-ylmethyl 7β-[(Z)-2-(2-aminothiazol-4-yl)-2-(acetoxyimino)acetamido]-3-[(Z)-3-acetoxyprop-1-en-1-yl]-3-cephem-4-carboxylate,

(68) 7β-[(Z)-2-(2-aminothiazol-4-yl)-2-(acetoxyimino)acetamido]-3-[(E)-3-acetoxyprop-1-en-1-yl]-3-cephem-4-carboxylic acid,

(69) acetoxymethyl 7β-[(Z)-2-(2-aminothiazol-4-yl)-2-(acetoxyimino)acetamido]-3-[(E)-3-acetoxyprop-1-en-1-yl]-3-cephem-4-carboxylate,

(70) 1-acetoxyethyl 7β-[(Z)-2-(2-aminothiazol-4-yl)-2-(acetoxyimino)acetamido]-3-[(E)-3-acetoxyprop-1-en-1-yl]-3-cephem-4-carboxylate,

(71) pivaloyloxymethyl 7β-[(Z)-2-(2-aminothiazol-4-yl)-2-(acetoxyimino)acetamido]-3-[(E)-3-acetoxyprop-1-en-1-yl]-3-cephem-4-carboxylate,

(72) 5-methyl-2-oxo-1,3-dioxolen-4-ylmethyl 7β-[(Z)-2-(2-aminothiazol-4-yl)-2-(acetoxyimino)acetamido]-3-[(E)-3-acetoxyprop-1-en-1-yl]-3-cephem-4-carboxylate,

(73) 7β-[(Z)-2-(2-aminothiazol-4-yl)-2-(isopropyloxyimino)acetamido]-3-[(Z)-prop-1-en-1-yl]-3-cephem-4-carboxylic acid,

(74) 1-acetoxyethyl 7β-[(Z)-2-(2-aminothiazol-4-yl)-2-(isopropyloxyimino)acetamido]-3-[(Z)-prop-1-en-1-yl]-3-cephem-4-carboxylate,

(75) pivaloyloxymethyl 7β-[(Z)-2-(2-aminothiazol-4-yl)-2-(isopropyloxyimino)acetamido]-3-[(Z)-prop-1-en-1-yl]-3-cephem-4-carboxylate,

(76) 7β-[(Z)-2-(2-aminothiazol-4-yl)-2-(allyloxyimino)acetamido]-3-[(Z)-prop-1-en-1-yl]-3-cephem-4-carboxylic acid,

(77) 1-acetoxyethyl 7β-[(Z)-2-(2-aminothiazol-4-yl)-2-(allyloxyimino)acetamido]-3-[(Z)-prop-1-en-1-yl]-3-cephem-4-carboxylate,

(78) pivaloyloxymethyl 7β-[(Z)-2-(2-aminothiazol-4-yl)-2-(allyloxyimino)acetamido]-3-[(Z)-prop-1-en-1-yl]-3-cephem-4-carboxylate,

(79) 7β-[(Z)-2-(2-aminothiazol-4-yl)-2-(ethoxyimino)acetamido]-3-[(Z)-prop-1-en-1-yl]-3-cephem-4-carboxylic acid,

(80) 1-acetoxyethyl 7β-[(Z)-2-(2-aminothiazol-4-yl)-2-(ethoxyimino)acetamido]-3-[(Z)-prop-1-en-1-yl]-3-cephem-4-carboxylate,

(81) pivaloyloxymethyl 7β-[(Z)-2-(2-aminothiazol-4-yl)-2-(ethoxyimino)acetamido]-3-[(Z)-prop-1-en-1-yl]-3-cephem-4carboxylate,

(82) 7β-[(Z)-2-(2-aminothiazol-4-yl)-2-(cyclopropylmethoxyimino)acetamido]-3-[(Z)-prop-1-en-1-yl]-3-cephem-4-carboxylic acid,

(83) 1-acetoxyethyl 7β-[(Z)-2-(2-aminothiazol-4-yl)-2-(cyclopropylmethoxyimino)acetamido]-3-[(Z)-prop-1-en-1-yl]-3-cephem-4-carboxylate,

(84) pivaloyloxymethyl 7β-[(Z)-2-(2-aminothiazol-4-yl)-2-(cyclopropylmethoxyimino)acetamido]-3-[(Z)-prop-1-en-1-yl]-3-cephem-4-carboxylate,

(85) 7β-[(Z)-2-(2-aminothiazol-4yl)-2-(propargyloxyimino)acetamido]-3-[(Z)-prop-1-en-1-yl]-3-cephem-4-carboxylic acid,

(86) 1-acetoxyethyl 7β-[(Z)-2-(2-aminothiazol-4-yl)-2-(propargyloxyimino)acetamido]-3-[(Z)-prop-1en-1-yl]-3-cephem-4-carboxylate,

(87) pivaloyloxymethyl 7β-[(Z)-2-(2-aminothiazol-4-yl)-2-(propargyloxyimino)acetamido]-3-[(Z)-prop-1-en-1-yl]-3-cephem-4-carboxylate, The in vitro antibacterial activity of parent cephalosporanic acids of Formula I is shown in Table 1 in terms of geometric mean of the Minimum Inhibitory Concentrations (MIC's) which were determined by the two-fold serial agar dilution method in Mueller-Hinton agar against 25 strains of test organisms in six groups.

Table 2 shows the mouse blood levels of pro-drug esters of Formula I which were determined after oral administrations.

Table 3 shows the in vivo activity of pro-drug esters of Formula I against *S. aureus* Smith, *E. coli* Juhl, *Pr. mirabilis* A9900, *Pr. vulgaris* A9436 and *Ser. marcescens* A20019.

Table 4 shows the urinary recovery of various esters in the mouse.

TABLE 1

In vitro Activity of Cephalosporin Acids

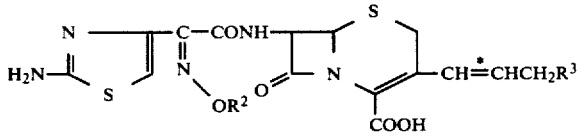

| Compound No. (BMY No.) | Ia * | Ia R² | Ia R³ | Geometric mean of MIC (mcg/ml) GpIa (5*) | GpIb (5) | GnIa (5) | GnIb (5) | GnII (5) |
|---|---|---|---|---|---|---|---|---|
| 29 (28232) | Z | H | H | 0.20 | 0.40 | 0.066 | 0.35 | 6.3 |
| 37 (28266) | Z | H | OAc | 0.17 | 0.40 | 0.025 | 0.1 | 1.1 |
| 53 (28270) | Z | Ac | H | 0.17 | 0.40 | 0.057 | 0.26 | 3.6 |
| 1 (28098) | Z | CH₃ | H | 1.8 | 3.6 | 0.1 | 0.52 | 6.3 |
| 4 (28252) | E | CH₃ | H | 2.4 | 3.6 | 0.3 | 0.91 | 8.4 |
| 7 (28154) | Z | CH₃ | CH₃ | 1.8 | 3.1 | 0.30 | 0.80 | 6.3 |
| 12 (28204) | E | CH₃ | CH₃ | 1.8 | 4.1 | 0.69 | 1.8 | 14 14 |
| 17 (28215) | Z | CH₃ | CH₂CH₃ | 1.1 | 1.6 | 0.53 | 1.2 | 7.2 |
| 20 (28217) | E | CH₃ | CH₂CH₃ | 1.2 | 2.4 | 0.46 | 0.91 | 6.3 |
| 45 (28248) | Z | CH₃ | OAc | 1.2 | 1.6 | 0.05 | 0.15 | 0.91 |
| 49 (28280) | E | CH₃ | OAc | 0.53 | 1.6 | 0.025 | 0.087 | 0.60 |
| 23 (28157) | Z | CH₃ | OCH₃ | 2.1 | 2.4 | 0.10 | 0.35 | 5.5 |
| 79 (28235) | Z | CH₂CH₃ | H | 2.1 | 3.1 | 0.30 | 0.91 | 7.3 |
| 73 (28233) | Z | CH(CH₃)₂ | H | 1.6 | 2.7 | 0.53 | 1.2 | 8.3 |
| 76 (28234) | Z | CH₂CH=CH₂ | H | 1.4 | 1.8 | 0.30 | 1.0 | 7.3 |
| 85 28237 | Z | CH₂C≡CH | H | 1.4 | 1.6 | 0.23 | 0.91 | 14.0 |
| 82 (28236) | Z | CH₂-◁ | H | 0.8 | 1.6 | 0.70 | 1.2 | 8.3 |
| Cefadroxil | | | | 1.4 | 3.6 | 8.3 | 17 | >100 |
| Cefaclor | | | | 0.7 | 4.7 | 0.92 | 11 | >100 |
| Cefvixim[1] (FK-027) | | 4.7 | 12.5 | 0.016 | 3.1 | 3.2 | | |

Gp-Ia: Penicillin (PC) - sensitive *S. aureus*
Gp-Ib: PC-resistant *S. aureus*
Gn-Ia: Cephalothin (CET) - sensitive *E. coli* (2 strains), *K. pneumoniae* (1) and *P. mirabilis* (2)
Gn-Ib: CET-resistant *E. coli* (3) and *K. pneumoniae* (2)
Gn-II: *M. morganii* (1), *E. cloacae* (2) and *S. marcescens* (2)

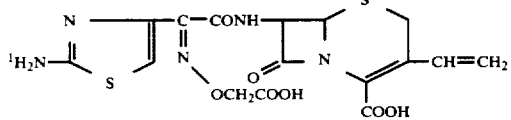

TABLE 2

Mouse Blood Levels of Pro-Drug Esters

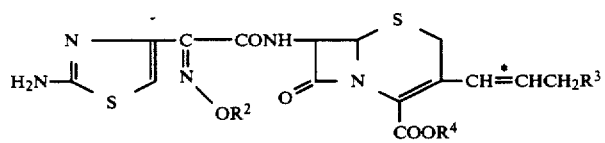

| Compound No. (BMY No.) | Ib R² | Ib R³ | Ib R⁴ | * | 100 mg/kg, po $C_{max}$ (mcg/ml) | T½ (hr) | AUC (mcg hr/ml) | 20 mg/kg, po $C_{max}$ (mcg/ml) | T½ (hr) | AUC (mcg hr/ml) |
|---|---|---|---|---|---|---|---|---|---|---|
| 30 (28271) | H | H | AX[3] | Z | 36 | 1.3 | 61 | 9.9 | 1.0 | 16 |
| 39 (28277) | H | OAc | AX | Z | | | | | | |
| 55 (28258) | Ac | H | AX | Z | 27 | 0.8 | 40 | 7.6 | 0.8 | 9.4 |
| 3 (28099) | CH₃ | H | PV[1] | Z | 33 | 2.2 | 76 | 6.9 | 2.4 | 18 |
| 2 (28191) | CH₃ | H | AX | Z | 50 | 2.3 | 118 | 21 | 1.9 | 37 |
| 5 (28255) | CH₃ | H | AX | E | | | | | | |
| 10 (28155) | CH₃ | CH₃ | PV | Z | 21 | 3.0 | 51 | 6.7 | 4.0 | 14 |
| 8 (28225) | CH₃ | CH₃ | AM[2] | Z | | | | 7.4 | 1.7 | 15 |
| 9 (28170) | CH₃ | CH₃ | AX | Z | 43 | 1.5 | 58 | 5.0 | 0.80 | 7.1 |
| 11 (28231) | CH₃ | CH₃ | GBM[4] | Z | | | | 5.4 | 2.30 | 13 |
| 14 (28205) | CH₃ | CH₃ | AX | E | 55 | 7.0 | 698 | 12 | 13 | 239 |
| 18 (28216) | CH₃ | CH₂CH₃ | AX | Z | 46 | 2.5 | 98 | 9.1 | 1.9 | 22 |
| 25 (28158) | CH₃ | OCH₃ | PV | Z | 15 | 2.3 | 27 | 3.3 | 1.7 | 6.1 |
| 24 (28171) | CH₃ | OCH₃ | AX | Z | 15 | 1.1 | 21 | 4.3 | 1.3 | 6.2 |
| Cefaclor | | | | | 26 | 1.2 | 35 | 8.5 | 0.91 | 8.9 |
| Cefvixim | | | | | 28 | 1.6 | 75 | 10 | 1.5 | 25 |

TABLE 2-continued

Mouse Blood Levels of Pro-Drug Esters

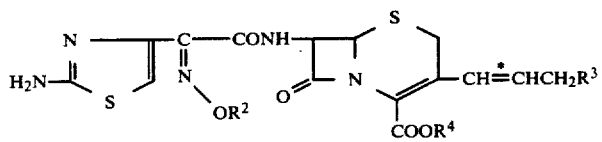

| | Ib | | | 100 mg/kg, po | | | 20 mg/kg, po | | |
|---|---|---|---|---|---|---|---|---|---|
| Compound No. (BMY No.) | $R^2$ | $R^3$ | $R^4$ * | $C_{max}$ (mcg/ml) | $T\frac{1}{2}$ (hr) | AUC (mcg hr/ml) | $C_{max}$ (mcg/ml) | $T\frac{1}{2}$ (hr) | AUC (mcg hr/ml) |
| Cefadroxil | | | | 57 | 1.6 | 69 | 12 | 1.4 | 16 |

[1]PV = $-CH_2OCOC(CH_3)_3$;
[2]AM = $-CH_2OCOCH_3$
[3]AX = $-CH(CH_3)OCOCH_3$

[4]GBM = 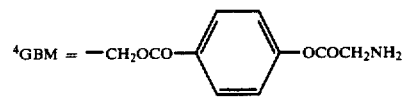

TABLE 3

In vivo Activity of Pro-Drug Esters in Mice
$PD_{50}$ (mg/kg, po)

| Compound No. (BMY No.) | S. aureus Smith | E. coli Juhl | P. mirabilis A9900 | P. vulgaris A9436 | S. marcescens A20019 |
|---|---|---|---|---|---|
| 55 (28258) | 1.8 | 0.36 | | | |
| 3 (28099) | 6.3 | 4.5 | | | |
| 2 (28191) | 8.5 | 1.6 | | | |
| 10 (28155) | 7.7 | 3.4 | 3.4 | 0.55 | 2.6 |
| 8 (28225) | 11 | | | | |
| 9 (28170) | 6.3 | 1.7 | 2.7 | <0.39 | 3.6 |
| 11 (28231) | >25 | | | | |
| 14 (28205) | 11 | | | | |
| 25 (28158) | 8.1 | | | | |
| 24 (28171) | 22.5 | | | | |
| Cefaclor | 0.35 | 0.63 | 3.0 | 3.1 | >25 |
| Cefvixim | >25 | 1.6 | 1.2 | 0.68 | 1.1 |
| Cefadroxil | 0.4 | 13 | — | — | — |

TABLE 4

Mouse Urinary Recovery of Oral Pro-Drug Esters

| Compound | Dose (mg/kg, po) | % Recovery | | | | |
|---|---|---|---|---|---|---|
| | | 0–2 hr | 2–4 | 4–6 | 6–24 | Total |
| BMY-28170[a] | 100 | 17 | 6.3 | 2.2 | 3.5 | 29 |
| | 20 | 13 | 4.0 | 1.1 | 1.6 | 19 |
| FK-027 | 100 | 2.9 | 9.1 | 6.9 | 6.5 | 25 |
| | 20 | 2.8 | 4.1 | 3.2 | 2.9 | 13 |

Assay standard
[a]BMY-28154

Another aspect of this invention relates to processes for the preparation of the compounds of Formula I. The preferred procedures are shown below in Reaction Schemes 1 and 2. In these reaction schemes the abbreviation Ph represents the phenyl group. Thus, the CH(Ph)$_2$ moiety is the benzhydryl or diphenylmethyl group which is preferred carboxyl protecting group. The abbreviation Tr means the trityl or triphenylmethyl group which is a preferred amino protecting group. $R^{2a}$ is a conventional protecting group used in cephalosporin chemistry with respect to hydroxy groups and includes trityl, chloroacetyl, formyl, trichloroethoxycarbonyl, tert.-butoxycarbonyl, carbobenzyloxy, etc. The definition of $R^{2a}$ also includes those same groups included in the definition of $R^2$ except for hydrogen.

Reaction Scheme 1 shows that the desired 7-side chain acid is introduced in the early stage. Then the group of the 3-position is converted to the substituted propenyl moiety. On the other hand, in Scheme 2 the 7-amino group of the starting Compound II is protected as a Schiff's base during most of the reaction stage and the desired 7-side chain acid is added later in the synthesis. Deblocking of both VIII and XIV gives the parent acids Ia which are converted to the pro-drug esters Ib by conventional procedures.

Reaction Scheme 1 shows two alternate means of going from Compound IV to Compound VI. One is the direct route of the reaction of the chloro derivative IV with triphenylphosphine to give the phosphonium and another is that the chloro derivative is converted to the more active iodo Compound V, then this is reacted with triphenylphosphine to give the phosphonium VI. There is no significant difference between them in their yields.

Reaction Scheme 2 shows two alternate means of going from Compound XIII to Compound Ia. One is acylation of XIII with 2-aminothiazolyl acid XX to Compound XIV followed by deblocking to Compound Ia. The other is acylation with a thiazolyl acid III having 2-N-protected-amino (such as N-tritylamino) group to give Compound VIII which is deblocked to Compound Ia.

In Reaction Schemes 1 and 2, the benzhydryl group was shown as the preferred carboxyl-protecting group. It will be appreciated by those skilled in the art that other carboxyl-protecting groups, well-known in the art, may be used. The acylating acid III or XX may be used in the form of a derivative such as its acid halide, activated ester, mixed acid anhydride, etc., all of which are well-known in the art. Acylating acid III also may have its amino group protected by any of the common amino-protecting groups, e.g. N-trityl, N-formyl, N-t-butoxycarbonyl or the like.

The base used to convert the phosphonium halide (VI or X) to give the phosphorylide (VII or XI) may be NaOH, Na$_2$CO$_3$, IRA-410 (OH$^-$) resin, IRA (CO$_3^{--}$) resin, or the like, or a mixture thereof. Reaction of the ylide VII (or XI) with acetaldehyde or substituted acetaldehyde will give the 3-propenyl derivative VIII (or XII).

We have found that Compound XII from XI (Scheme 2) typically had a Z:E ratio of about 3–5:1 at the 3-(1-propenyl) configuration, while Compound VIII from VII (Scheme 1) exclusively had the Z configuration. The difference may not be in the route used, but in the conditions utilized in the Wittig reaction (VII to VIII or XI to XII). We have also found that the use of an appropriate lithium halide such as lithium chloride, lithium bromide or lithium iodide in the Wittig reaction caused improvement of the yield and purity of the Wittig reaction product VIII (or XII). The reaction is preferably carried out with 5–15 equivalents of the lithium halide. If desired the Z isomer of the Compound XIII (XIII(Z) in Scheme 3) may be converted to the corresponding E isomer (XIII(E)) by photochemical reaction in the presence of a sensitizer. The reaction is usually carried out in a solvent selected from methanol, ethanol, propanol, benzene, toluene, acetone, acetonitrile, dichloromethane, DMF, ethyl acetate, THF, pyridine and the like in the presence of 0.5–10 equivalent(s) of a sensitizer selected from acetophenone, benzophenone, benzil, naphthalene, ethyl pyruvate and the like. In the Scheme 3, $R^{4a}$ means hydrogen or benzhydryl.

Deblocking of VIII (or XIV) to Ia is usually carried out with trifluoroacetic acid (TFA) in an adequate solvent in the presence of anisole. The acid Ia thus obtained was purified by reverse phase column chromatography utilizing a glass column containing the packing removed from a Waters' Associates Prep-PAK500/$C_{18}$ cartridge.

The ester Ib may be prepared in a conventional manner, for example by reacting the acid Ia or a salt thereof (such as sodium, potassium, triethylammonium, etc.) with a halogenated compound of the formula $$R^4-X$$

wherein X is chloro, bromo or iodo and $R^4$ is a group selected from

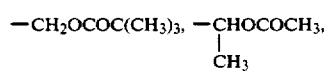

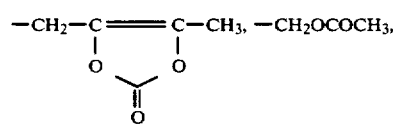

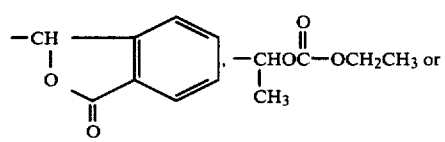

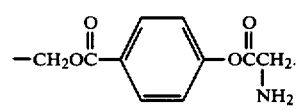

The reaction is carried out effectively in an inert organic solvent such as N,N-dimethylformamide, N,N-dimethylacetamide, dimethylsulfoxide, acetone, acetonitrile, or the like, at a temperature in the range of from −10° C. to +50° C., conveniently between 0° C. and 5° C. The ester Ib thus obtained is purified by conventional column chromatography by using silica gel.

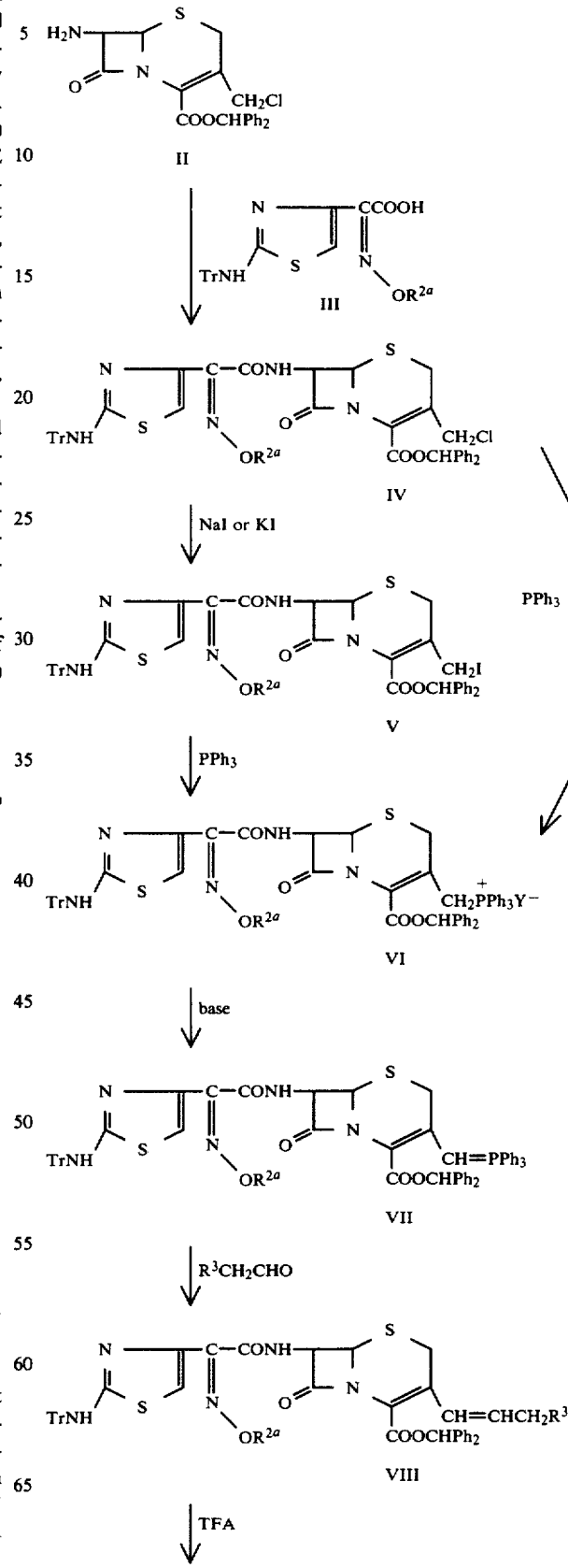

Reaction Scheme 1

-continued
Reaction Scheme 1
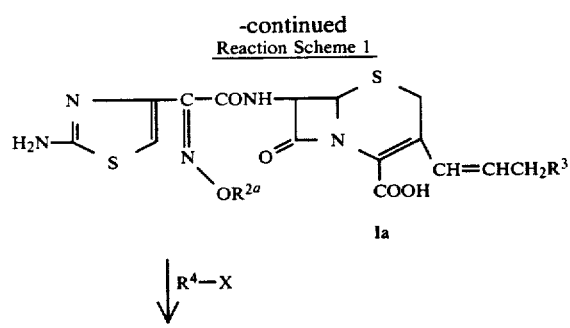
Ia
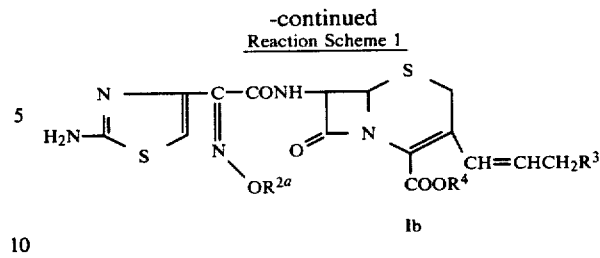
Ib
↓ R⁴—X
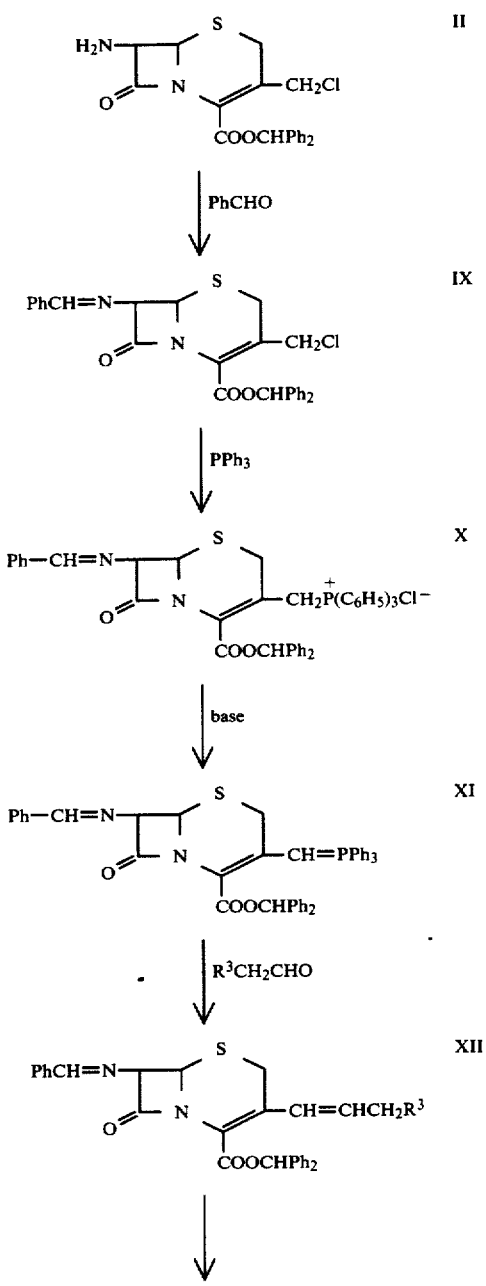

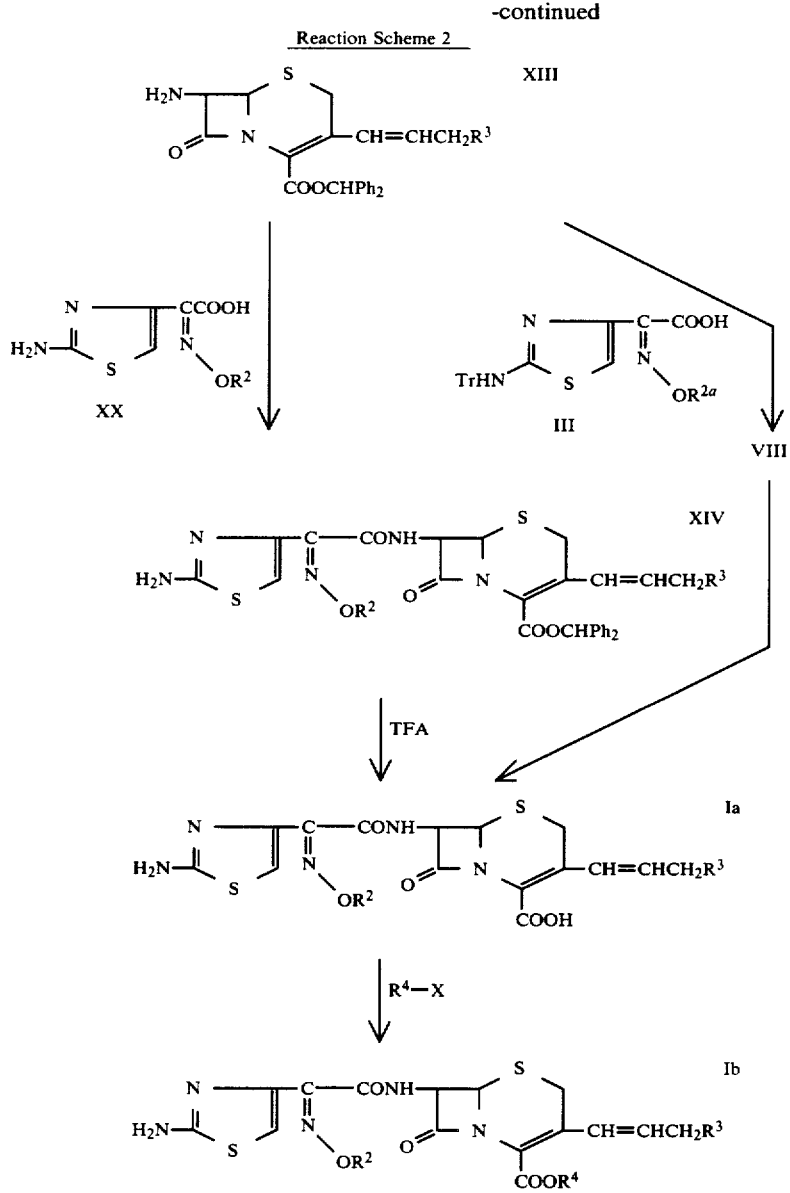
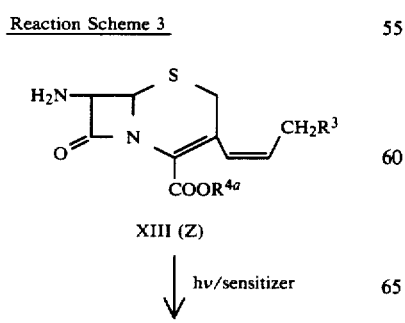
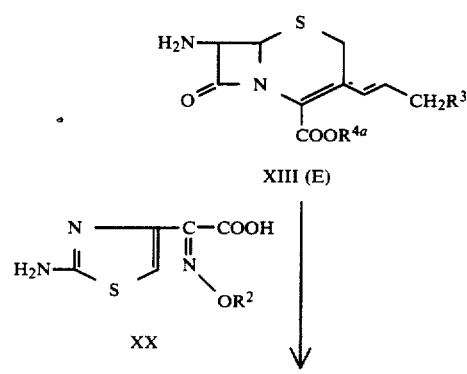

-continued
Reaction Scheme 3

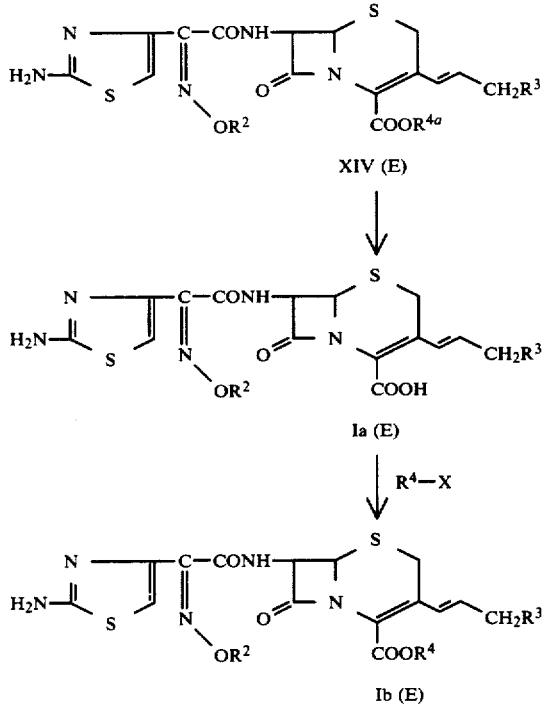

XIV (E)

↓

Ia (E)

↓ R⁴—X

Ib (E)

EXAMPLE 1

Diphenylmethyl 7-amino-3-(1-propenyl)-3-cephem-4-carboxylate (XIII, $R^3$=H)

To a solution of diphenylmethyl 7-benzylideneamino-3-[(triphenylphosphoranylidene)methyl]-3-cephem-4-carboxylate (XI) (2.9 g, 4 mmoles) in dichloromethane (16 ml) was added 90% acetaldehyde (10 ml, 0.2 mmole). The mixture was stirred at room temperature for 30 minutes, dried over sodium sulfate and concentrated in vacuo. The residue was dissolved in ethyl acetate (80 ml). To the solution was added isopropyl ether (160 ml) and then silica gel (25 g). The mixture was gently agitated and filtered to remove the solid. The filtrate was evaporated into dryness in vacuo. To a solution of the residue in ethyl acetate (48 ml) was added a mixture of Girard's reagent T (1.34 g, 8 mmoles), methanol (40 ml) and acetic acid (2 ml). The mixture was stirred at room temperature for 30 minutes and concentrated to ca. 10 ml. The residue was dissolved in ethyl acetate (100 ml). The solution was washed with aqueous sodium bicarbonate and water, dried over sodium sulfate and concentrated in vacuo. The residue was chromatographed on a silica gel column (50 g), which was eluted with 1% methanol in chloroform. The eluate was collected in 18-ml fractions. Fraction Nos. 22–40 were combined and concentrated to give 718 mg of the 3-propenyl derivative XIII ($R^3$=H). (Yield 44%, E/Z=½).

TLC: Rf 0.56 (silica gel, ethyl acetate).

HPLC*: Retention time (min.) 13.2 and 15.6 (relative intensity=3:1).

IR: $\nu_{max}$ (KBr) in cm$^{-1}$ 1770, 1720.

UV: $\lambda_{max}$ (C₂H₅OH) in nm (ε) 214 (20500), 222 (20800), 266 (4200), 273 (4200), 292 (3800).

NMR (a 1:3 mixture of E and Z isomers): δ(CDCl₃) in ppm 1.42 and 1.72 (relative intensity=3:1) (both are dd, J=2 and 7 Hz, CH₃), 3.37 (ABq, J=18 Hz, 2-H) and 3.52 (s, 2-H), 4.72 (d, J=4.5 Hz, 6-H), 4.97 (d, J=4.5 Hz, 7-H), 5.50 (dq, J=7 and 11 Hz, =CH—), 6.06 (dd, J=2 and 11 Hz, 3—CH=), 6.96 and 7.00 (3:1) (s, —OCHPh₂), 7.35 (s, phenyl-H).

*Packing: Lichrosorb RP-18 (4×300 mm). Mobile phase: CH₃CN—H₂O (1:1). Flow rate: 2.5 ml/min.

EXAMPLE 2

Diphenylmethyl 7-[(Z)-2-(2-aminothiazol-4-yl)-2-methoxyiminoacetamido]-3-(1-propenyl)-3-cephem-4-carboxylate (XIV, $R^2$=CH₃, $R^3$=H)

A mixture of diphenylmethyl 7-amino-3-(1-propenyl)-3-cephem-4-carboxylate (XIII, $R^3$=H) (3.37 g, 8.3 mmoles) and 1-[(Z)-2-(2-aminothiazol-4-yl)-2-methoxyiminoacetoxy]benzotriazole* (2.64 g, 8.3 mmoles) in THF (70 ml) was stirred at room temperature for 30 minutes and then evaporated in vacuo. A solution of the residue in ethyl acetate was washed successively with aqueous sodium bicarbonate and water, dried over anhydrous sodium sulfate and concentrated in vacuo to afford a crude product, which was dissolved in chloroform and chromatographed on a silica gel column (150 g) with 2% methanol in CHCl₃. The desired fractions (TLC: silica gel, Rf 0.49, 1:2 toluene-ethyl acetate) were combined and concentrated to yield 1.95 g (40%) of XIV ($R^2$=CH₃, $R^3$=H) [a 1:2 mixture of E and Z isomers with respect to 3-(1-propenyl) configuration].

*Hoechst, Japan Kokai No. 54-95593 (7/28/79) and Ger. Offen No. 2758000 (5/7/79) (Ger. Appl. No. P2758000.3, 12/24/77).

NMR (a 1:2 mixture of the E and Z isomers): δ(CDCl₃) in ppm 1.45 and 1.75 (relative intensity 2:1) (both are d, J=7 Hz, C—CH₃), 3.42 and 3.53 (2:1) (s, 2-H), 4.02 (s, OCH₃), 5.13 (d, J=4.5 Hz), 5.2–6.3 (m, 7-H and vinyl-H), 6.73 (s, thiazole-H), 6.93 (s, OCHPh₂), 7.30 (s, phenyl-H).

EXAMPLE 3

7-[(Z)-2-(2-Aminothiazol-4-yl)-2-methoxyiminoacetamido]-3-(1-propenyl)-3-cephem-4-carboxylic acid (Ia, $R^2$=CH₃, $R^3$=H)

Compound XIV ($R^2$=CH₃, $R^3$=H) (1.9 g, 3.2 mmoles) was treated with trifluoroacetic acid (TFA) (5 ml) at room temperature for 40 minutes. The mixture was diluted with isopropyl ether (IPE). The resulting precipitate was collected by filtration, dissolved in formic acid and passed through a column of the packing (50 ml) of a PrepPAK cartridge (Waters), which was washed with water and eluted with 15% methanol and 20% methanol successively. Evaporation and lyophilization of 15% methanol eluate gave 206 mg (15%) of the title compound (E/Z=1/17). Estimated purity 90% (by HPLCO. Mp.>180° C. (slow decomp.).

IR: $\nu_{max}$ (KBr) in cm$^{-1}$ 1770, 1660, 1630, 1530.

UV: $\nu_{max}$ (pH 7 phosphate buffer) in nm (ε) 228 (17400), 283 (16200).

NMR: δ(D₂O+K₂CO₃) in ppm 1.70 (3H, d, J=6 Hz, C—CH₃), 3.52 (2H, ABq, J=18 Hz, 2-H), 4.03 (3H, s, OCH₃), 5.28 (1H, d, J=4.5 Hz, 6-H), 5.6–6.2 (3H, m, 7-H and vinyl-H), 7.30 (1H, thiazole-H).

HPLC: Retention time, 6.8 times (1:3 methanol-pH 7 phosphate buffer, 1.5 ml/min.)

Anal. Calc'd. for $C_{16}H_{17}N_5O_5S_2 \cdot \frac{1}{2}H_2O$: C, 44.44; H, 4.20; N, 16.19; S, 14.83. Found: C, 44.37; H, 3.94; N, 16.18; S, 14.53.

EXAMPLE 4

Pivaloyloxymethyl 7-[(Z)-2-(2-aminothiazol-4-yl)-2-methoxyiminoacetamido]-3-[(Z)-1-propenyl]-3-cephem-4-carboxylate (Ib, $R^2=CH_3$, $R^3=H$, $R^4=PV^*$)

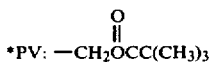

*PV: —CH$_2$OCC(CH$_3$)$_3$

To a mixture of 7-[(Z)-2-(2-aminothiazol-4-yl)-2-methoxyiminoacetamido]-3-(1-propenyl)-3-cephem-4-carboxylic acid (Ia, $R^2=CH_3$, $R^3=H$) (E/Z=1/17, 90 mg, 0.21 mmole) and potassium carbonate (44 mg, 0.32 mmole) in DMF (3 ml) was added at 0° C. pivaloyloxymethyl iodide (77 mg, 0.32 mmole). The mixture was stirred at 0° C. for 40 minutes, diluted with ethyl acetate (20 ml), washed with water, dried over anhydrous sodium sulfate and evaporated in vacuo. The residue was dissolved in CHCl$_3$ and chromatographed on a silica gel column (silica gel: 3 g) by eluting with 1% methanol in CHCl$_3$ to yield 85 mg (75%) of the title compound. Mp. 100°-104° C. Estimated purity 90% (by HPLC).

IR: $\nu_{max}$ (KBr) in cm$^{-1}$ 1780, 1760, 1680, 1620.

UR: $\lambda_{max}$ (methanol) in nm ($\epsilon$) 232 (17800), 287 (13500).

NMR: $\delta$(CDCl$_3$) in ppm 1.23 (9H, s, C(CH$_3$)$_3$), 2.15 (3H, d, J=7 Hz, CCH$_3$), 3.45 (2H, s, 2-H), 4.05 (3H, s, OCH$_3$), 5.12 (1H, d, J=4.5 Hz, 6-H), 5.6–6.2 (5H, m, 7-H, vinyl-H and —OCH$_2$O—), 6.85 (1H, s, thiazole-H).

HPLC: Retention time 8.1 times (1:1 CH$_3$CN—H$_2$O, 2 ml/min.)

EXAMPLE 5

1-Acetoxyethyl 7-[(Z)-2-(2-aminothiazol-4-yl)-2-methoxyiminoacetamido]-3-[(Z)-1-propenyl]-3-cephem-4-carboxylate (Ib, $R^2=CH_3$, $R^3=H$, $R^4=AX^*$)

*AX=—CH(CH$_3$)OCOCH$_3$

To a mixture of 7-[(Z)-2-(2-aminothiazol-4-yl)-2-methoxyiminoacetamido]-3-(1-propenyl)-3-cephem-4-carboxylic acid (190 mg, 0.45 mmole) and potassium carbonate (75 mg, 0.54 mmole) in DMF (5 ml) was added at 5° C. 1-bromoethyl acetate** (90 mg, 0.54 mmole). The mixture was stirred at 5° C. for 1.5 hours and diluted with ethyl acetate (20 ml). The dilute was washed successively with water and a saturated aqueous NaCl solution, dried over anhydrous magnesium sulfate and concentrated in vacuo. The residue was dissolved in chloroform and chromatographed on a silica gel column (5 g) with 1% methanol in chloroform. The desired fractions were combined and concentrated. The residue was dissolved in dioxane and lyophilized to yield 103 mg (45%) of the title compound as its dioxane solvate. Mp. 105°-110° C. Estimated purity 85% (by HPLC).

**E. Buckley and E. Whittle, Can. J. Chem., 40, 1611 (1962).

NMR: $\delta$(CDCl$_3$) in ppm 1.50 (3H, d, J=6 Hz, OCHCH$_3$), 1.65 (3H), d, J=7 Hz, =CH—CH$_3$), 2.07 (3H, s, COCH$_3$), 3.43 (2H, s, 2-H), 3.68 (4H, s, ½ dioxane), 4.05 (3H, s, OCH$_3$), 5.10 (1H, d, J=4.5 Hz, 6-H), 5.5–6.0 (2H, m, 7-H and =CH—CH$_3$), 6.12 (1H, d, J=12 Hz, 3-CH=), 6.83 (1H, s, thiazole-H), 6.98 (1H, q, J=6 Hz, OCHO).

HPLC: Retention time, 7.5 minutes (1:1 CH$_3$CN—H$_2$O, 1 ml/min.)

EXAMPLE 6

Diphenylmethyl 7-amino-3-[(Z)-1-butenyl]-3-cephem-4-carboxylate hydrochloride (XIII, $R^3$=CH$_3$ hydrochloride)

To a solution of propionaldehyde (10.7 g, 18 mmoles) and lithium iodide (13.4 g, 10 mmoles) in DMF/CH$_2$Cl$_2$ (50 ml/150 ml) was added XI (7.3 g 10 mmoles) at 0° C. The mixture was allowed to stand at 5° C. for 2 days and concentrated in vacuo. A solution of the residue in ethyl acetate (200 ml) was washed with water, dried over MgSO$_4$ and evaporated in vacuo to a syrup, which was treated with CCl$_4$ (200 ml) and filtered. The filtrate was concentrated to ca. 50 ml and the concentrate was stirred with 6N HCl (4 ml) at room temperature for 30 minutes. The resulting precipitate was collected by filtration and recrystallized from CHCl$_3$-ethyl acetate to yield 1.49 g (33%) of the title compound. Mp. 120°-127° C.

IR: $\nu_{max}$ (KBr) in cm$^{-1}$ 1780, 1710.

UV: $\lambda_{max}$ (methanol) in nm ($\epsilon$) 217 (13900), 286 (7400).

NMR: $\delta$(DMSO-d$_6$) in ppm 0.93 (3H, t, J=7 Hz, CH$_3$), 2.00 (2H, m, CH$_2$CH$_3$), 3.75 (2H, ABq, J=16 Hz, 2-H), 5.1–5.9 (3H, m, 6-H and 7-H, =CH—CH$_2$—), 6.33 (1H, d, J=12 Hz, 3-CH=), 6.97 (1H, s, —CHPh$_2$), 7.40 (10H, s, phenyl-H).

HPLC: Retention time (minutes) 10.4 and 12.0 (relative intensity=8:1) (4:1 methanol-pH 7 phosphate buffer, 1 ml/min.)

EXAMPLE 7

Diphenylmethyl 7-[(Z)-2-(2-aminothiazol-4-yl)-2-methoxyiminoacetamido]-3-[(Z)-1-butenyl]-3-cephem-4-carboxylate (XIV, $R^2$=CH$_3$, $R^3$=CH$_3$)

A suspension of diphenylmethyl 7-amino-3-[(Z)-1-butenyl]-3-cephem-4-carboxylate hydrochloride (1.41 g, 3.1 mmoles) in ethyl acetate (20 ml) was shaken with aqueous NaHCO$_3$ to give a clear two-layer solution. The organic layer was separated, washed with water and then an aqueous saturated NaCl solution, and dried over MgSO$_4$. To the dried filtrate was added 1-[(Z)-2-(2-aminothiazol-4-yl)-2-methoxyiminoacetoxy]benzotriazole (1.27 g, 4.0 mmoles), and the mixture was stirred at room temperature for 20 hours. The reaction mixture was filtered and the filtrate was washed with aqueous NaHCO$_3$, water and a saturated NaCl solution, dried over MgSO$_4$ and evaporated in vacuo. The residue was chromatographed on a silica gel column (40 g) with 3:1 CHCl$_3$-ethyl acetate to yield 1.7 g (91%) of the title compound. TLC (silica gel): Rf 0.25 (1:1 CHCl$_3$-ethyl acetate).

IR: $\nu_{max}$ (KBr) in cm$^{-1}$ 1780, 1720, 1680, 1620.

UV: $\nu_{max}$ (ethanol) in nm ($\epsilon$) 288 (12400).

NMR: $\delta$(CDCl$_3$) in ppm 0.86 (3H, t, J=7 Hz, —CH$_3$), 1.90 (2H, m, CH$_2$CH$_3$), 3.45 (2H, s, 2-H), 4.06 (3H, s, OCH$_3$), 5.15 (1H, d, J=4.5 Hz, 6-H), 5.45 (1H, dt, J=7 and 11 Hz, =CH—CH$_2$—), 6.05 (1H, dd, J=4.5 and 9 Hz, 7-H), 6.17 (1H, d, J=11 Hz, 3—CH=), 6.75 (1H, s, thiazole-H), 6.97 (1H, s, CHPh$_2$), 7.35 (10H, s, phenyl-H), 8.08 (1H, d, J=9=Hz, CONH).

EXAMPLE 8

7-[(Z)-2-(2-Aminothiazol-4-yl)-2-methoxyiminoacetamido]-3-[(Z)-1-butenyl]-3-cephem-4-carboxylic acid (Ia, $R^2$=CH$_3$, $R^3$=CH$_3$)

A mixture of diphenylmethyl 7-[(Z)-2-(2-aminothiazol-4-yl)-2-methoxyiminoacetamido]-3-[(Z)-1-butenyl]-3-cephem-4-carboxylate (1.65 g, 2.65 mmoles) and anisole (0.5 ml) was treated with TFA (5 ml) at room temperature for 1 hour. The mixture was diluted with IPE. The resulting precipitate*[1] was collected by filtration and chromatographed on a column of the packing (50 ml) of a PrepPAK cartridge (Waters) with 20–30% methanol to yield 605 mg (52%) of the title compound. Estimated purity 90% (by HPLC). Mp. >160° C. (grad. dec.).

*[1]HPLC: Retention time (minutes), 5.0 and 6.4 (relative intensity=8:1) (3:7 methanol-pH 7 phosphate buffer, 2 ml/min.)

IR: $\nu_{max}$ (KBr) in cm$^{-1}$ 1760, 1670, 1650, 1620.

UV: $\lambda_{max}$ (pH 7 phosphate buffer) in nm ($\epsilon$) 232 (16200), 283 (15500).

NMR: $\delta$(D$_2$O+NaHCO$_3$) in ppm 1.00 (3H, t, J=7 Hz, CH$_3$), 2.00 (2H, dq, J=7 and 7 Hz, —CH$_2$CH$_3$), 3.52 (2H, ABq, J=17 Hz, 2-H), 4.02 (3H, s, OCH$_3$), 5.27 (1H, d, J=4.5 Hz, 6-H), 5.4–6.1 (3H, m, 7-H and —CH=CH—), 7.00 (1H, s, thiazole-H).

Anal. Calc'd. for C$_{17}$H$_{19}$N$_5$O$_5$S$_2$.½H$_2$O: C, 45.73; H, 4.51; N, 15.69; S, 14.36. Found: C, 45.41, H, 4.23; N, 15.35; S, 14.21.

EXAMPLE 9

Pivaloyloxymethyl 7-[(Z)-2-(2-aminothiazol-4-yl)-2-methoxyiminoacetamido]-3-[(Z)-1-butenyl]-3-cephem-4-carboxylate (Ib, $R^2$=CH$_3$, $R^3$=CH$_3$, $R^4$=PV*)

*PV=—CH$_2$OCOC(CH$_3$)$_3$

Pivaloyloxymethyl iodide (162 mg, 0.67 mmole) was added at 0° C. to a mixture of 7-[(Z)-2-(2-aminothiazol-4-yl)-2-methoxyiminoacetamido]-3-[(Z)-1-butenyl]-3-cephem-4-carboxylic acid (197 mg, 0.45 mmole) and K$_2$CO$_3$ (93 mg, 0.67 mmole) in DMF (4 ml). The mixture was stirred at 0°–5° C. for 1 hour and diluted with ethyl acetate (30 ml). The dilute was washed with water and a saturated NaCl solution, dried over anhydrous MgSO$_4$ and evaporated in vacuo. The residue was chromatographed on a silica gel column (5 g) with 1% methanol in CHCl$_3$. The desired fractions were combined and concentrated in vacuo. The residue was dissolved in dioxane and lyophilized to afford 242 mg (97%) of the dioxane solvate of the title compound. Silica gel TLC: Rf 0.25 (1:1 CHCl$_3$-ethyl acetate). Estimated purity 85% (by HPLC). Mp. 90°–95° C.

IR: $\nu_{max}$ (KBr) in cm$^{-1}$ 1780, 1750, 1670.

UV: $\lambda_{max}$ (ethanol) in nm ($\epsilon$) 233 (15300), 285 (11300).

NMR: $\delta$(CDCl$_3$) in ppm 0.97 (3H, t, J=7 Hz CH$_2$CH$_3$), 1.23 (9H, s, C(CH$_3$)$_3$), 2.03 (2H, dq, J=7 and 7 Hz, —CH$_2$CH$_3$), 3.43 (2H, s, 2-H), 3.67 (4H, s, ½ dioxane), 4.02 (3H, s, OCH$_3$), 5.10 (1H, d, J=4.5 Hz, 6-H), 5.3–6.3 (5H, m, 7-H, —CH=CH— and —OCH$_2$O—), 6.82 (1H, s, thiazole-H), 7.97 (1H, d, J=8 Hz, CONH).

HPLC: Retention time, 10.0 minutes (1:1 CH$_3$CN—H$_2$O, 2 ml/min.).

Anal. Calc'd. for C$_{23}$H$_{29}$N$_5$O$_7$S$_2$.½C$_4$H$_8$O$_2$: C, 50.41; H, 5.58; N, 11.76; S, 10.76. Found: C, 49.94; H, 5.57; N, 11.56; S, 10.76.

EXAMPLE 10

1-Acetoxyethyl 7-[(Z)-2-(2-aminothiazol-4-yl)-2-methoxyiminoacetamido]-3-[(Z)-1-butenyl]-3-cephem-4-carboxylate (Ib, $R^2$=CH$_3$, $R^3$=CH$_3$, $R^4$=AX*)

*AX=—CH(CH$_3$)OCOCH$_3$

To a mixture of 7-[(Z)-2-(2-aminothiazol-4-yl)-2-methoxyiminoacetamido]-3-[(Z)-1-butenyl]-3-cephem-4-carboxylic acid (1.55 g, 3.54 mmoles) and K$_2$CO$_3$ (636 mg, 4.6 mmoles) in DMF (4 ml) was added at 5° C. 1-bromoethyl acetate (769 mg, 4.6 mmoles). The mixture was stirred at 5° C. for 1 hour, diluted with ethyl acetate (300 ml), washed with water, dried over anhydrous MgSO$_4$ and concentrated in vacuo. The residue was dissolved in chloroform and chromatographed on a silica gel column (50 g) with 1% methanol in CHCl$_3$. The desired fractions were combined and concentrated to a small volume. The resdiue was triturated with isopropyl ether to give 1.29 g (70%) of the title compound as the isopropyl ether solvate. Estimated purity 90% (by HPLC). Mp. 103°–110° C. (dec.).

IR: $\nu_{max}$ (KBr) in cm$^{-1}$ 1770 (br.), 1670, 1620.

UV: $\lambda_{max}$ (ethanol) in nm ($\epsilon$) 233 (14300), 288 (11000).

NMR: $\delta$(CDCl$_3$) in ppm 1.00 (3H, t, J=7 Hz, —CH$_2$CH$_3$), 1.12 (12H, d, J=6 Hz, isopropyl ether CH$_3$), 1.53 (3H, d, J=5 Hz, OCHCH$_3$), 1.95 (2H, m, CH$_2$CH$_3$), 2.08 (3H, s, COCH$_3$), 3.43 (2H, s, 2-H), 3.62 (2H, m, isopropyl ether CH), 4.08 (3H, s, OCH$_3$), 5.13 (1H, d, J=4.5 Hz, 6-H), 5.2–6.2 (3H, m, 7-H and —CH=CH—), 6.87 (1H, s, thiazole-H), 7.00 (1H, q, J=5 Hz, —CHCH$_3$).

HPLC: Retention time, 10.8 minutes (1:1 CH$_3$CN—H$_2$O, 1 ml/min.)

Anal. Calc'd. for C$_{21}$H$_{25}$N$_5$O$_7$S$_2$.C$_6$H$_{14}$O: C, 51.83; H, 6.28; N, 11.19; S, 10.25. Found: C, 51.62; H, 6.07; N, 11.16; S, 10.05.

EXAMPLE 11

Diphenylmethyl 7-[(Z)-2-methoxyimino-2-(2-tritylaminothiazol-4-yl)acetamido]-3-[(Z)-3-methoxy-1-propenyl]-3-cephem-4-carboxylate (VIII, $R^{2a}$=CH$_3$, $R^3$=OCH$_3$)

A solution of diphenylmethyl 7-[(Z)-2-methoxyimino-2-(2-tritylaminothiazol-4-yl)acetamido]-3-triphenylphosphoniomethyl-3-cephem-4-carboxylate iodide (1.19 g, 1 mmole) in CH$_2$Cl$_2$ (30 ml) was shaken with 1N NaOH (5 ml) for 2 minutes. The organic layer was separated, washed with water and a saturated aqueous NaCl solution, dried over anhydrous sodium sulfate and filtered. To the filtrate was added isopropyl alcohol (15 ml) and methoxyacetaldehyde (7.41 mg, 10 mmoles). The mixture was stirred at room temperature overnight and evaporated to dryness in vacuo. The residue was dissolved in CHCl$_3$ and chromatographed on a silica gel column (20 g) with a 1:20 ethyl acetate-toluene as eluant to afford 570 mg (66%) of the title compound.

IR: $\nu_{max}$ (KBr) in cm$^{-1}$ 1775, 1720, 1670, 1525, 1175.

NMR: $\delta$(CDCl$_3$+D$_2$O) in ppm 3.24 (3H, s, OCH$_3$), 3.3–3.8 (4H, m, S—CH$_2$ and OCH$_2$), 4.13 (3H, s, NOCH$_3$), 5.15 (1H, d, J=4.5 Hz, 6-H), 5.98 (1H, d, J=4.5 Hz, 7-H), 6.3 (1H, d, J=11 Hz, vinyl-H), 6.8 (1H, s, thiazole-H), 6.98 (1H, s, CHPH$_2$), 7.1–7.5 (25H, phenyl-H).

HPLC: Retention time 13.6 minutes (3:1 CH$_3$CN—H$_2$O, 1 ml/min.).

EXAMPLE 12

7-[(Z)-2-(2-Aminothiazol-4-yl)-2-methoxyiminoacetamido]-3-[(Z)-3-methoxy-1-propenyl]-3-cephem-4-carboxylic acid (Ia, $R^2=CH_3$, $R^3=OCH_3$)

A solution of diphenylmethyl 7-[(Z)-2-methoxyimino-2-(2-tritylaminothiazol-4-yl)acetamido]-3-[(Z)-3-methoxy-1-propenyl]-3-cephem-4-carboxylate (550 mg, 0.64 mmole) in anisole-TFA (0.5 ml/5 ml) was allowed to stand at room temperature for 50 minutes and diluted with isopropyl ether to give a precipitate, which was collected by filtration and washed with IPE. The solid was dissolved in methanol and chromatographed on a column of the packing (40 ml) of a Prep-PAK cartridge (Waters) with 30% methanol as eluant to afford 104 mg (36%) of the title compound. Mp. 155°–159° C. (dec.). Estimated purity 90% (by HPLC).

IR: $\nu_{max}$ (KBr) in cm$^{-1}$ 1765, 1660, 1630, 1530, 1040.

UV: $\lambda_{max}$ (methanol) in nm ($\epsilon$) 234 (16600), 287 (14500).

NMR: $\delta$(DMSO-$d_6$+$D_2O$) in ppm 3.19 (3H, s, OCH$_3$), 3.83 (3H, s, OCH$_3$), 5.17 (1H, d, J=5 Hz, 6-H), 5.4–5.8 (1H, m, vinyl-H), 5.72 (1H, d, J=5 Hz, 7-H), 6.27 (1H, d, J=12 Hz, vinyl-H), 6.72 (1H, s, thiazole-H).

HPLC: Retention time 9.6 minutes (1:3 methanol-pH 7 phosphate buffer, 1 ml/min.).

Anal. Calc'd. for $C_{17}H_{19}N_5O_6 \cdot H_2O$: C, 43.30; H, 4.49; N, 14.85; S, 13.60. Found: C, 43.04; H, 4.09; N, 14.59; S, 13.89.

EXAMPLE 13

Pivaloyloxymethyl 7-[(Z)-2-(2-aminothiazol-4-yl)-2-methoxyiminoacetamido]-3-[(Z)-3-methoxy-1-propenyl]-3-cephem-4-carboxylate (Ib, $R^2=CH_3$, $R^3=OCH_3$, $R^4=PV$)

Esterification of 7-[(Z)-2-(2-aminothiazol-4-yl)-2-methoxyiminoacetamido]-3-[(Z)-3-methoxy-1-propenyl]-3-cephem-4-carboxylic acid (226 mg, 0.5 mmole) in a similar manner to that described in Example 9 gave the title compound (97 mg, 34%). Mp. 100°–102° C. Estimated purity 90% (by HPLC, 1:1 methanol-pH 7 phosphate buffer).

IR: $\nu_{max}$ (KBr) in cm$^{-1}$ 1775, 1750, 1670, 1530, 1370, 1120.

UV: $\lambda_{max}$ (methanol) in nm ($\epsilon$) 232 (16600), 289 (13500).

NMR: $\delta$(DMSO-$d_6$+$D_2O$) in ppm 1.18 (9H, s, 3×CH$_3$), 3.19 (3H, s, OCH$_3$), 3.57 (2H, br., SCH$_2$), 3.85 (3H, s, OCH$_3$), 5.23 (1H, d, J=5 Hz, 6-H), 5.4–5.9 (4H, m, 7-H, OCH$_2$O and vinyl-H), 6.24 (1H, d, J=12 Hz, vinyl-H), 6.74 (1H, s, thiazole-H).

EXAMPLE 14

1-Acetoxyethyl 7-[(Z)-2-(2-aminothiazol-4-yl)-2-methoxyiminoacetamido]-3-[(Z)-3-methoxy-1-propenyl]-3-cephem-4-carboxylate (Ib, $R^2=CH_3$, $R^3=OCH_3$, $R^4=AX$)

Esterification of 7-[(Z)-2-(2-aminothiazol-4-yl)-2-methoxyiminoacetamido]-3-[(Z)-3-methoxy-1-propenyl]-3-cephem-4-carboxylic acid (300 mg, 0.66 mmole) with 1-bromoethyl acetate in a similar manner to that described in Example 10 gave the title compound (154 mg, 43%). Mp. 102°–105° C. (dec.). Estimated purity 95% (by HPLC, 1:1 CH$_3$CN-pH 7 phosphate buffer).

IR: $\nu_{max}$ (KBr) in cm$^{-1}$ 1775–1760, 1670, 1530, 1375.

UV: $\lambda_{max}$ (methanol) in nm ($\epsilon$) 232 (15900), 288 (13000).

NMR: $\delta$(CDCl$_3$+$D_2O$) in ppm 1.51 (3H, d, J=5 Hz, CHCH$_3$), 2.07 (3H, s, COCH$_3$), 3.29 (3H, s, CH$_2$OCH$_3$), 3.45 (2H, br., S—CH$_2$), 3.87 (2H, d, J=7 Hz, =CHCH$_2$O), 4.04 (3H, s, NOCH$_3$), 5.09 (1H, d, J=5 Hz, 6-H), 5.55–5.9 (1H, m, vinyl-H), 5.97 (1H, d, J=5 Hz, 7-H), 6.8 (1H, d, J=12 Hz, vinyl-H), 6.83 (1H, s, thiazole-H), 6.97 (1H, q, J=5 Hz, OCHCH$_3$).

EXAMPLE 15

7-[(Z)-2-(2-Aminothiazol-4-yl)-2-methoxyiminoacetamido]-3-[(E)-1-butenyl]-3-cephem-4-carboxylic acid (Ia, $R^2=CH_3$, $R^3=CH_3$, E isomer)

A mixture of the diphenylmethyl 7-[(Z)-2-(2-aminothiazol-4-yl)-2-methoxyiminoacetamido]-3-[(Z)-1-butenyl]-3-cephem-4-carboxylate which was obtained in Example 7 (7.6 g, 1.3 mmoles), TFA (25 ml) and anisole (5 ml) was stirred at 5° C. for 1 hour and diluted with isopropyl ether. The resulting precipitate was collected by filtration, dissolved in formic acid and purified by preparative HPLC (Waters, System 500, PrepPAK-500/C$_{18}$) with 40% methanol. The eluate was monitored by analytical HPLC and grouped in two fractions, which were evaporated in vacuo to give 0.94 g of the Z isomer of Ia ($R^2=CH_3$, $R^3=CH_3$) and 1.65 g of a mixture of the Z isomer and the corresponding E isomer. The mixture was dissolved in formic acid and chromatographed on a column of the packing (50 ml) of a PrepPAK cartridge (Waters) with 20–30% methanol to yield 0.22 g (4%) of the E isomer together with 0.90 g of the Z isomer. Estimated purity 90% (by HPLC). Mp. >170° C. (grad. dec.).

IR: $\nu_{max}$ (KBr) in cm$^{-1}$ 1760, 1660.

UV: $\lambda_{max}$ (pH 7 phosphate buffer) in nm ($\epsilon$) 232 (15400), 292 (19400).

NMR: $\delta$($D_2O$+NaHCO$_3$) in ppm 1.18 (3H, t, J=7 Hz, CH$_2$CH$_3$), 2.30 (2H, m, CH$_2$CH$_3$), 3.83 (2H, s, 2-H), 4.15 (3H, s, OCH$_3$), 5.37 (1H, d, J=5 Hz, 6-H), 5.92 (1H, d, J=5 Hz, 7-H), 5.9–6.4 (1H, m, =CHCH$_2$), 5.66 (1H, d, J=16 Hz, 3-CH=), 7.18 (1H, s, thiazole-H).

HPLC: Retention time 6.4 minutes (3:7 methanol-pH 7 phosphate buffer, 2.0 ml/min.)

EXAMPLE 16

1-Acetoxyethyl 7-[(Z)-2-(2-aminothiazol-4-yl)-2-methoxyiminoacetamido]-3-[(E)-1-butenyl]-3-cephem-4-carboxylate (Ib, $R^2=CH_3$, $R^3=CH_3$, $R^4=AX$ E isomer)

To a mixture of 7-[(Z)-2-(2-aminothiazol-4-yl)-2-methoxyiminoacetamido]-3-[(E)-1-butenyl]-3-cephem-4-carboxylic acid (130 mg, 0.3 mmole) and K$_2$CO$_3$ (55 mg, 0.4 mmole) in DMF (2.5 ml) was added at 5° C. 1-bromoethyl acetate (67 mg, 0.4 mmole). The mixture was stirred at 5° C. for 1 hour, diluted with ethyl acetate (25 ml), washed successively with water and an aqueous NaCl solution, dried over anhydrous MgSO$_4$ and concentrated in vacuo. The residue was dissolved in chloroform and chromatographed on a silica gel column with 1% methanol in CHCl$_3$. The desired fractions were combined and concentrated in vacuo to yield 77 mg (49%) of the title compound. Estimated purity 90% (by HPLC). Mp. 110°–115° C.

IR: $\nu_{max}$ (KBr) in cm$^{-1}$ 1760 (br.), 1670, 1510.

UV: $\lambda_{max}$ (methanol) in nm ($\epsilon$) 232 (15100), 298 (17000).

NMR: $\delta$(CDCl$_3$) in ppm 1.05 (3H, t, J=7 Hz, CH$_2$CH$_3$), 1.54 (3H, d, J=6 Hz, CHCH$_3$), 2.08 (3H, s, COCH$_3$), 2.0–2.4 (2H, m, —CH$_2$CH$_3$), 3.57 (2H, s, 2-H), 4.05 (3H, s, OCH$_3$), 5.07 (1H, d, J=5 Hz, 6-H), 5.8–6.3 (2H, m, 7-H and =CH—CH$_2$—), 6.86 (1H, s, thiazole-H), 6.8–7.1 (2H, m, OCH and 3-CH=).

HPLC: Retention time, 7.7 minutes (1:1 CH$_3$CN—H$_2$O, 1.5 min/ml.).

EXAMPLE 17

Acetoxymethyl 7-[(Z)-2-(2-aminothiazol-4-yl)-2-methoxyiminoacetamido]-3-[(Z)-1-butenyl]-3-cephem-4-carboxylate (Ib. R$^2$=CH$_3$, R$^3$=CH$_3$, R$^4$=CH$_2$OCOCH$_3$, Z isomer)

To a mixture of 7-[(Z)-2-(2-aminothiazol-4-yl)-2-methoxyiminoacetamido]-3-[(Z)-1-butenyl]-3-cephem-4-carboxylic acid (300 mg, 0.69 m mole) and K$_2$CO$_3$ (95 mg, 0.69 m mole) in dry DMF (3 ml) was added dropwise at 0° C. a solution of bromomethyl acetate (105 mg, 0.69 m mole) in dry DMF (0.25 ml) and the mixture was stirred at 0° C. for 15 minutes. To the mixture was added again a solution of bromomethyl acetate (105 mg, 0.69 m mole) in dry DMF (0.25 ml). The reaction mixture was stirred for another 30 minutes and diluted with ethyl acetate (20 ml). The dilute was washed with water and a saturated NaCl solution, dried over anhydrous Na$_2$SO$_4$ and evaporated to dryness. The residue was dissolved in methanol and passed through a column of the packing (40 ml) of a PrepPAK cartridge (Waters), which was washed with water and then eluted with 50% methanol. The eluate was monitored by HPLC. The desired fractions were collected and evaporated to give 96 mg (27%) of the title compound. Estimated purity 90% (by HPLC). M.p. 149°–152° C.

IR: $\nu_{max}$ (KBr) in cm$^{-1}$ 1780, 1660, 1535, 1375, 1170, 1045.

UV: $\lambda_{max}$ (methanol) in nm ($\epsilon$) 231 (17000), 289 (13100).

NMR: $\delta$(CDCl$_3$+D$_2$O) in ppm 0.99 (3H, t, J=7.2 Hz, CH$_3$), 2.11 (3H, s, COCH$_3$), 1.75–2.5 (2H, m, CH$_2$CH$_3$), 3.45 (2H, s, S—CH$_2$), 4.05 (3H, s, OCH$_3$), 5.11 (1H, d, J=4.5 Hz, 6-H), 5.81 (2H, s, OCH$_2$O), 5.99 (1H, d, J=4.5 Hz, 7-H), 6.18 (1H, d, J=12 Hz, 3-CH=), 6.76 (1H, s, thiazole-H).

HPLC: Retention time, 6.3 minutes (3:2 CH$_3$CN-pH 7 phosphate buffer).

Anal. Calcd. for C$_{20}$H$_{23}$N$_5$O$_7$S$_2$.½H$_2$O: C, 46.32; H, 4.66; N, 13.50; S, 12.37. Found: C, 46.51; H, 4.44; N, 13.34; S, 12.25.

EXAMPLE 18

4-[N-(t-Butoxycarbonyl)glycyloxy)benzoyloxymethyl 7-[(Z)-2-(2-aminothiazol-4-yl)-2-methoxyiminoacetamido]-3-[(Z)-1-butenyl]-3-cephem-4-carboxylate (Ib. R$^2$=CH$_3$, R$^3$=CH$_3$, R$^4$=BOC-GBM*)

*BOC—GBM =

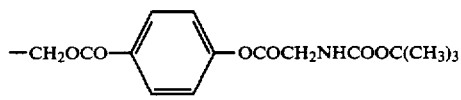

A solution of chloromethyl 4-[N-(t-butoxycarbonyl)-glycyloxybenzoate (584 mg, 1.7 m moles) in acetone (10 ml) was stirred with sodium iodide (1.28 g, 8.5 m moles) at room temperature for 6 hr. The separated sodium chloride was removed by filtration. The filtrate was concentrated in vacuo. The residue was dissolved in dimethylformamide (10 ml) and added at −20° C. to a mixture of 7-[(Z)-2-(2-aminothiazol-4-yl)-2-methoxyiminoacetamido]-3-[(Z)-1-butenyl]-3-cephem-4-carboxylic acid (437 mg, 1 m mole) and potassium carbonate (207 mg, 1.5 m mole) in dimethylformamide (5 ml). The mixture was stirred at 0° C. for 1 hr, diluted with ethyl acetate (50 ml), washed successively with water and an aqueous solution of sodium chloride, dried over anhydrous magnesium sulfate and concentrated in vacuo. The residue was chromatographed on a silica gel column (20 g) eluting with 1:1 toluene-ethyl acetate to yield 533 mg (76%) of the title compound. TLC (silica gel): Rf 0.16 (1:1 toluene-ethyl acetate). M.p. 110°–117° C.

IR: $\nu_{max}$ (KBr) in cm$^{-1}$ 1770, 1740, 1670.

UV: $\lambda_{max}$ (methanol) in nm ($\epsilon$) 237 (26700), 287 (11800).

NMR: $\delta$(CDCl$_3$+D$_2$O) in ppm 0.90 (3H, t, J=7 Hz, CH$_2$CH$_3$), 1.48 (9H, s, C(CH$_3$)$_3$), 2.00 (2H, dq, J=7 and 7 Hz, CH$_2$CH$_3$), 3.43 (2H, s, 2-E), 3.98 (3H, s, OCH$_3$), 4.13 (2H, s, CH$_2$NH), 5.10 (1H, d, J=4.5 Hz, 6-H), 5.50 (1H, dt, J=11 and 7 Hz), 5.9–6.3 (4H, m, 7-H, vinyl-H and OCH$_2$O), 6.52 (1H, s, thiazole-H), 7.17 and 8.06 (2H each, d, J=8 Hz, benzene-H).

EXAMPLE 19

4-Glycyloxybenzoyloxymethyl 7-[(Z)-2-(2-aminothiazol-4-yl)-2-methoxyiminoacetamido]-3-[(Z)-1-butenyl]-3-cephem-4-carboxylate dihydrochloride (Ib, R$^2$=CH$_3$, R$^3$=CH$_3$, R$^4$=GBM*, hydrochloride)

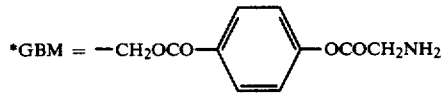

*GBM = —CH$_2$OCO—⟨benzene⟩—OCOCH$_2$NH$_2$

A mixture of the N-(t-butoxycarbonyl) derivative (349 mg, 0.5 m mole) obtained in Example 18, anisole (3 drops) and 2N hydrochloric acid in ethyl acetate (2.5 ml) was stirred at 5° C. for 15 min. The resulting precipitate was collected by filtration and dissolved in methanol (3 ml). After filtration, ethyl acetate (39 ml) was added to the filtrate. The resulting precipitate was collected by filtration to yield 166 mg (46%) of the title compound. M.p. >160° C. (dec.). Estimated purity 90% (by HPLC).

IR: $\nu_{max}$ (KBr) in cm$^{-1}$ 1780, 1745, 1670, 1630.

UV: $\lambda_{max}$ (methanol) in nm ($\epsilon$) 235 (27200), 287 (12900).

NMR: $\delta$(DMSO-d$_6$) in ppm 0.78 (3H, t J=7 Hz, CH$_2$CH$_3$), 2.00 (2H, m, CH$_2$CH$_3$), 3.52 (2H, s, 2-H), 3.90 (3H, s, OCH$_3$), 4.05 (2H, s, CH$_2$NH), 5.22 (1H, d, J=5 Hz, 6-H), 5.5–6.2 (5H, m, 7-H), vinyl-H×2 and OCH$_2$O), 6.88 (1H, s, thiazole-H), 7.35 and 8.00 (2H each, d, J=8 Hz, benzene-H).

Anal. Calcd. for C$_{27}$H$_{28}$N$_6$O$_9$S$_2$.2HCl.½H$_2$O: C, 44.63; H, 4.30; N, 11.57; S, 8.82; Cl, 9.76. Found: C, 44.60; H, 4.34; N, 11.13; S, 8.46; Cl, 9.18.

HPLC: Retention time, 5.2 minutes (3:2 CH$_3$CN—H$_2$O, 1 ml/min.)

EXAMPLE 20

Diphenylmethyl
7-amino-3-(1-pentenyl)-3-cephem-4-carboxylate (XIII, $R^3 = CH_2CH_3$)

To a cooled and stirred solution of 8.7 g (0.1 mole) of anhydrous lithium bromide in 50 ml of DMF was added in one portion a solution of 7.3 g (0.01 mole) of the ylide (XI) in 250 ml of methylene chloride. To the solution was added 30 ml of n-butyraldehyde and the mixture was stirred at room temperature for 24 hours. After concentrating to 50 ml, the residue was extracted with 300 ml of ethyl acetate. The extract was washed with water and a saturated NaCl solution, and dried with anhydrous MgSO$_4$. Wako-gel (C-100, 10 g) and active carbon (1 g) were added. The mixture was filtered and the filtrate was concentrated to 100 ml. To the concentrate was added 5 g (0.03 mole) of Girard T in 100 ml of methanol containing 5 ml of acetic acid and the mixture was stirred at room temperature for 30 min. After being evaporated to dryness, the residue was extracted with 300 ml of ethyl acetate. The extract was washed successively with water, an aqueous sodium bicarbonate solution, water and a saturated NaCl solution and dried with anhydrous MgSO$_4$. After evaporating to dryness, the residue was chromatographed on a silica gel column (Merck Kieselgel 60, 120 g) by eluting with toluene-ethyl acetate (5:1). The desired fraction collected by monitoring with TLC were evaporated to dryness to give 1.78 g (41%) of title compound as a foamy solid.

NMR: $\delta$(CDCl$_3$) in ppm 0.7–2.0 (7H, m, CH$_2 \times$2 & C—CH$_3$), 3.28 (1H, d, J=18 Hz, 2-H), 3.58 (1H, d, J=18 Hz, 2-H), 4.75 (1H, d, J=4.5 Hz, 6-H), 5.01 (1H, d, J=4.5 Hz, 7-H), 5.2–5.7 (1H, m, CH=C), 6.12 (1H, d, J=11 Hz, 3-CH=C), 7.00 (1H, s, CHPh$_2$), 7.2–7.6 (10H, m, phenyl-H).

EXAMPLE 21

Diphenylmethyl
7-[(Z)-2-(2-aminothiazol-4-yl)-2-methoxyiminoacetamido]-3-(1-pentenyl)-3-cephem-4-carboxylate (XIV, $R^2 = CH_3$, $R^3 = CH_2CH_3$)

A mixture of 1.7 g (3.9 m mole) of XIII ($R^3 = CH_2CH_3$) and 1.24 g (3.9 m mole) of 1-[(Z)-2-(2-aminothiazol-4-yl)-2-methoxyiminoacetoxy]benzotriazole in 150 ml of ethyl acetate was stirred at room temperature for 20 hours and the mixture was evaporated to dryness. The residue was chromatographed on a silica gel column (Merck Kieselgel 60, 60 g) by eluting with chloroform and 1% methanol in chloroform successively. The desired fractions, eluted with chloroform-methanol and monitored by silica gel TLC (1:15 MeOH-CHCl$_3$, Rf 0.50), were collected and evaporated to dryness. The residue was triturated with ether-isopropyl ether to give 1.94 g (85%) of the title compound, melting at 115°–120° C. (dec.)

IR: $\nu_{max}$(KBr) in cm$^{-1}$ 1775, 1720, 1670, 1610, 1530, 1380, 1220, 1180, 1030.

UV: $\lambda_{max}$ (methanol) in nm ($\epsilon$) 290 (14000).

NMR: $\delta$(CDCl$_3$) in ppm 0.6–2.1 (7H, m, CH$_2 \times$2 & CH$_3$), 3.42 (2H, brs, 2-H), 4.04 (3H, s, OCH$_3$), 5.15 (1H, d, J=4.5 Hz, 6-H), 5.3–5.8 (3H, m, CH=C & NH$_2$), 6.02 (1H, d-d, J=4.5 & 8 Hz, 7-H), 6.15 (1H, d, J=11 Hz, 3-CH=C), 6.80 (1H, s, thiazole, H), 6.98 (1H, s, CHPh$_2$), 7.2–7.5 (10H, m, phenyl-H), 8.0 (1H, d, J=8 Hz, NH).

EXAMPLE 22

7-[(Z)-2-(2-Aminothiazol-4-yl)-2-methoxyiminoacetamido]-3-[(Z)-1-pentenyl]-3-cephem-4-carboxylic acid (Ia, $R^2 = CH_3$, $R^3 = CH_2CH_3$, Z isomer)

A mixture of 2.5 g (4.27 m moles) of XIV ($R^2 = CH_3$, $R^3 = CH_2CH_3$), 2.5 ml of anisole and 7.5 ml of trifluoroacetic acid was stirred at room temperature for 10 min and concentrated to 3 ml. The residue was diluted with 100 ml of isopropyl ether to give 2 g of trifluoroacetate of the title compound (a 5:1 mixture of Z and E isomers). The crude product was dissolved in aqueous methanol and the solution was chromatographed on a column of the packing of PrepPAK C$_{18}$ cartridge (Waters, 300 ml) by eluting successively with water, 10% methanol, 20% methanol, 30% methanol and 40% methanol. The elutate was monitored with HPLC. The Z isomer-containing fractions of the 40% methanol elutate were collected and evaporated to dryness and the residual solid was dissolved in methanol and filtered. To the filtrate was added 200 ml of isopropyl ether and the resulting solid was collected by filtration, washed with isopropyl ether and dried in vacuo over P$_2$O$_5$ to give 695 mg (39%) of the product, which was 90% pure by HPLC. M.p. 150°–155° (dec.).

IR: $\nu_{max}$(KBr) in cm$^{-1}$ 1770, 1670, 1630, 1530, 1370, 1180, 1040.

UV: $\lambda_{max}$ (pH 9 phosphate buffer) in nm ($\epsilon$) 229 (16000), 283 (15000).

NMR: $\delta$(D$_2$O + Na$_2$CO$_3$) in ppm 1.01 (3H, t, J=7 Hz, CH$_2$CH$_3$), 1.3–1.7 (2H, CH$_2$CH$_2$CH$_3$), 2.0–2.3 (2H, m, =CH—CH$_2$—CH$_2$), 3.46 (1H, d, J=18 Hz, 2-H), 3.76 (1H, d, J=18 Hz, 2-H), 4.15 (3H, s, OCH$_3$), 5.38 (1H, d, J=4.5 Hz, 6-H), 5.5–5.9 (1H, m, CH=C), 5.92 (1H, d, J=4.5 Hz, 7-H), 6.09 (1H, d, J=11 Hz, 3-CH=C), 7.16 (1H, s, thiazole-H).

Anal. Calcd. for C$_{18}$H$_{21}$N$_5$O$_5$S$_2$.½H$_2$O: C, 46.94; H, 4.82; N, 15.21; S, 13.92. Found: C, 46.93, 47.04; H, 4.66; 4,71; N, 15.00, 15.00; S, 13.34, 13.36.

HPLC: Retention time, 9.9 minutes (2:3 MeOH-pH 7 phosphate buffer, 1 ml/min.).

EXAMPLE 23

7-[(Z)-2-(2-Aminothiazol-4-yl)-2-methoxyiminoacetamido]-3-[(E)-1-pentenyl]-3-cephem-4-carboxylic acid (Ia, $R^2 = CH_3$, $R^3 = CH_2CH_3$, E isomer)

The E isomer-containing fractions of the 40% methanol eluate (cf. Example 22) were collected and evaporated to dryness to give 455 mg of a mixture of cis and trans isomers (1:1). The crude product was rechromatographed on a column of the packing of PrepPAK C$_{18}$ cartridge (Waters, 300 ml) by eluting with 35% methanol and monitoring with HPLC. The desired fractions containing the trans isomer were collected and concentrated to 10 ml and lyophilized to give 89 mg (5%) of the product which was 75% pure by HPLC. M.p. 180° C. (grad. dec.).

IR: $\nu_{max}$(KBr) in cm$^{-1}$ 1770, 1660, 1630, 1530, 1380, 1040.

UV: $\lambda_{max}$ (pH 7 phosphate buffer) in nm ($\epsilon$) 228 (17000), 292 (22000).

NMR: $\delta$(D$_2$O + Na$_2$CO$_3$) in ppm 1.05 (3H, t, J=7 Hz, CH$_2$CH$_3$), 1.2–1.8 (2H, m, CH$_2$CH$_2$CH$_3$), 2.1–2.5 (2H, m, =CH—CH$_2$CH$_2$), 3.81 (2H, s, 2-H), 4.16 (3H, s, OCH$_3$), 5.37 (1H, d, J=4.5 Hz, 6-H), 5.91 (1H, d, J=4.5 Hz, 7-H), 5.9–6.3 (1H, m, CH=C), 6.67 (1H, d, J=16 Hz, 3-CH=C), 7.17 (1H, s, thiazole-H).

HPLC: Retention time, 12.3 minutes (2:3 MeOH-pH 7 phosphate buffer, 1 ml/min.).

EXAMPLE 24

1-Acetoxyethyl 7-[(Z)-2-(2-aminothiazol-4-yl)-2-methoxyiminoacetamido]-3-[(Z)-1-pentenyl]-3-cephem-4-carboxylate (Ib. $R^2=CH_3$, $R^3=CH_2CH_3$, $R^4=AX$, Z isomer)

To a stirred mixture of Ia ($R^2=CH_3$, $R^3=CH_2CH_3$, Z isomer) (225 mg, 0.5 m mole) and 69 mg (0.5 m mole) of potassium carbonate in 5 ml of DMF was added at 0°–5° C. a solution of 84 mg (0.5 m mole) of 1-acetoxyethyl bromide in 1 ml of DMF and the mixture was stirred at room temperature for 30 min. To the mixture was added again a solution of 84 mg (0.5 m mole) of the bromide in 1 ml of DMF and the mixture was stirred at 5°–10° C. for 30 min. Then, the mixture was extracted with 100 ml of ethyl acetate. The extract was washed with an aqueous sodium bicarbonate solution, water and a saturated NaCl solution successively and dried with $MgSO_4$. After evaporating to dryness, the oily residue was chromatographed on a silica gel column (Kieselgel 60, 30 g) by eluting with chloroform and 1% methanol in chloroform successively, and monitoring with TLC and HPLC. The desired fractions eluting with 1% methanol in chloroform were collected and evaporated to dryness. The residue was triturated with ether-n-hexane to give 91 mg of the title compound. The crude side fractions were re-chromatographed similarly to give additional 63 mg of the product. The total yield was 154 mg (57%). Est'd purity 80% by HPLC. M.p. 100°–110° C. (dec.).

IR: $\nu_{max}$(KBr) in $cm^{-1}$ 1765, 1670, 1610, 1530, 1380, 1240, 1210, 1180, 1100, 1070, 1040.

UV: $\lambda_{max}$ (methanol) in nm ($\epsilon$) 233 (17000), 290 (13000).

NMR: $\delta$(CDCl$_3$) in ppm 0.90 (3H, t, J=7 Hz, CH$_2$CH$_3$), 1.2–1.8 (5H, m, CHCH$_3$ & CH$_2$CH$_2$CH$_3$), 1.8–2.1 (2H, m, =CH—CH$_2$CH$_2$), 2.06 (3H, s, COCH$_3$), 3.43 (2H, br-s, 2-H), 4.05 (3H, s, OCH$_3$), 5.08 (1H, d, J=4.5 Hz, 6-H), 5.32 (2H, br-s, NH$_2$), 5.5–5.7 (1H, m, CH=C), 5.94 (1H, d-d, J=8 & 4.5 Hz, 7-H), 6.13 (1H, d, J=11 Hz, 3-CH=C), 6.84 (1H, s, thiazole-H), 6.97 (1H, q, J=7 Hz, CH—CH$_3$), 7.48 (1H, d, J=8 Hz, NH).

HPLC: Retention time, 8.1 minutes (7:3 MeOH-pH 7 phosphite buffer, 1 ml/min).

EXAMPLE 25

Diphenylmethyl 7-[2-(2-tritylaminothiazol-4-yl)-2-(Z)-isopropyloxyiminoacetamido]-3-[(Z)-1-propenyl]-3-cephem-4-carboxylate (VIII, $R^{2a}=CH(CH_3)_2$, $R^3=H$)

To a mixture of 2-(2-tritylaminothiazol-4-yl)-2-(Z)-isopropyloxyiminoacetic acid (III, $R^{2a}=CH(CH_3)_2$: 754 mg, 1.60 m moles) and dichloromethane (7 ml) was added phosphorus pentachloride (332 mg, 1.60 m moles) at −10° C. The mixture was allowed to stand for 20 min at the same temperature and added dropwise to a solution of diphenylmethyl 7-amino-3-[(Z)-1-propenyl]-3-cephem-4-carboxylate hydrochloride (XIII, $R^3=H$: 443 mg, 1 m mole) and N,O-bis(trimethylsilyl)acetamide (0.74 ml, 4.4 m moles) in dichloromethane (5 ml) at −10° C. The reaction mixture was allowed to stand for 30 min. at the same temperature and poured into ice-water. Extraction of the mixture with ethyl acetate followed by evaporation of the extracts under reduced pressure gave the crude product as on oil, which was chromatographed on a column of silica gel (eluted with chloroform) to give 419 mg (49%) of VIII ($R^2=CH(CH_3)_2$, $R^3=H$) as an amorphous powder.

IR: $\nu_{max}$(KBr) in $cm^{-1}$ 1780, 1720, 1680.

*R. Bucourt et al., Tetrahedron 34, 2233 (1978)

EXAMPLE 26

7-[2-(2-Aminothiazol-4-yl)-2-(Z)-isopropyloxyiminoacetamido]-3-((Z)-1-propenyl)-3-cephem-4-carboxylic acid (Ia, $R^2=CH(CH_3)_2$, $R^3=H$)

A mixture of VIII ($R^{2a}=CH(CH_3)_2$, $R^3=H$: 400 mg, 0.47 m mole) and 85% formic acid (2 ml) was stirred for 3 hr at room temperature and to the mixture was added hydrochloric acid (0.08 ml). The mixture was stirred for additional 4 hr and evaporated under reduced pressure. The residue was triturated with isopropyl ether to give the crude product, which was purified by column chromatography on C-18 silica gel (eluent, 30% aq. MeOH) followed by concentration under reduced pressure to give the title compound as needles. Yield 70 mg (33%). M.p. 170°–175° C. (dec.). Est'd purity 90%.

IR: $\nu_{max}$(KBr) in $cm^{-1}$ 1760, 1660, 1540, 1380.

UV: $\lambda_{max}$ (pH 7 phosphate buffer) in nm ($E_{1\ cm}^{1\%}$) 232 (370), 284 (357).

NMR: $\delta$ (D$_2$O+NaHCO$_3$) in ppm 1.50 (6H, d, J=6 Hz, i-Pr), 1.76 (3H, d, J=6 Hz, =CH—CH$_3$), 3.65 (2H, ABq, J=18 Hz, 2-H), 5.42 (1H, d, J=4 Hz, 6-H), 5.80–6.40 (3H, m, vinyl-H, 7-H), 7.15 (1H, s, thiazole-H).

EXAMPLE 27

Diphenylmethyl 7-[2-(2-tritylaminothiazol-4-yl)-2-(Z)-allyloxyiminoacetamido]-3-((Z)-1-propenyl)-3-cephem-4-carboxylate (2) (VIII, $R^{2a}=CH_2CH=CH_2$, $R^3=H$)

To a mixture of 2-(2-tritylaminothiazol-4-yl)-2-(Z)-allyloxyiminoacetic acid (III, $R^{2a}=CH_2CH=CH_2$) (750 mg, 1.60 m moles) and dichloromethane (5 ml) was added phosphorus pentachloride (332 mg, 1.60 m moles) at −10° C. The mixture was allowed to stand for 20 min at the same temperature and added dropwise to a solution of diphenylmethyl 7-amino-3-((Z)-1-propenyl)-3-cephem-4-carboxylate hydrochloride (XIII, $R^3=H$: 443 mg, 1 m mole) and N,O-bis(trimethylsilyl)acetamide (0.74 ml, 4.4 m moles) in dichloromethane (5 ml) at −10° C. The reaction mixture was allowed to stand for 30 min. at the same temperature and poured into ice-water. Extraction of the mixture with chloroform and evaporation of the extracts under reduced pressure gave the crude product as an oil, which was chromatographed on a column of silica gel (eluted with chloroform) to give 817 mg (95%) of VIII ($R^{2a}=CH_2CH=CH_2$, $R^3=H$) as an amorphous powder.

IR: $\nu_{max}$(KBr) in $cm^{-1}$ 1780, 1720, 1680.

*R. Bucourt et al., Tetrahedron 34, 2233 (1978)

EXAMPLE 28

7-[2-(2-Aminothiazol-4-yl)-2-(Z)-alloxyiminoacetamido]-3-((Z)-1-propenyl)-3-cephem-4-carboxylic acid (Ia, $R^2=CH_2CH=CH_2$, $R^3=H$)

A mixture of VIII ($R^{2a}=CH_2CH=CH_2$, $R^3=H$: 810 mg, 0.95 m mole) and 85% formic acid (2 ml) was stirred for 3 hr at room temperature and to the mixture was added hydrochloric acid (0.1 ml). The mixture was stirred for 3 hr and evaporated under reduced pressure. Trituration of the residue with isopropyl ether gave the crude product, which was dissolved in a small amount of methanol and chromatographed on a column of C-18 silica gel (eluted with 30% aq. MeOH). The eluate was concentrated under reduced pressure and freeze-dried to give 215 mg (50%) of the title compound as an amorphous powder. M.p. 140° C. (dec.). Est'd purity 80%.

IR: $\nu_{max}$ (KBr) in cm$^{-1}$ 1770, 1660, 1620.

UV: $\lambda_{max}$ (pH 7 phosphate buffer) in nm (E$_1$ $_{cm}$$^{1\%}$) 232 (378), 285 (326).

NMR: δ (D$_2$O+NaHCO$_3$) in ppm 1.78 (3H, d, J=6 Hz, C=CH—CH$_3$), 3.62 (2H, ABq, J=18 Hz, 2-H), 5.50–6.30 (7H, m, vinyl-H, 6,7-H), 7.18 (1H, s, thiazole-H).

EXAMPLE 29

7-[(Z)-2-(2-Aminothiazol-4-yl)-2-(Z)-ethoxyiminoacetamido]-3-((Z)-1-propenyl)-3-cephem-4-carboxylic acid (Ia, R$^2$=C$_2$H$_5$, R$^3$=H)

To a solution of (Z)-2-(2-N-tritylaminothiazol-4-yl)-2-ethoxyiminoacetic acid* (III, R$^{2a}$=C$_2$H$_5$) (458 mg, 1.0 m mole) and 1-hydroxybenzotriazole (135 mg, 1.0 m mole) in a mixture of dichloromethane (20 ml) and tetrahydrofuran (7 ml) at room temperature was added dicyclohexylcarbodiimide (210 mg, 1.0 m mole). The mixture was stirred for 80 min, filtered and the filtrate was concentrated to dryness. The residue was dissolved in tetrahydrofuran (10 ml) and diphenylmethyl 3-propenyl-3-cephem-4-carboxylate hydrochloride (XIII, R$^3$=H: 443 mg, 1 m mole) and sodium bicarbonate (84 mg, 1 m mole) were added. Water (10 drops) was added and the resulting solution was stirred at room temperature for 12 hr. The reaction mixture was diluted with ether and filtered. The filtrate was concentrated to give an oil. The oil was chromatographed on silica gel (230–400 mesh), eluting with 2:1 hexane-ethyl acetate to give the acylation product (VIII, R$^{2a}$=C$_2$H$_5$, R$^3$=H) (400 mg). This was dissolved in formic acid (1.6 ml), stirred vigorously for 60 min and 12N HCl (50 μl) was added. The mixture was stirred at room temperature for 3 hr, diluted with water (2 ml) and toluene (20 ml) and evaporated at 30° C. to dryness. The residue was triturated with isopropyl ether, the resulting precipitates were collected and washed with isopropyl ether. The solid was chromatographed on C-18 silica gel, eluting with 3:7 methanol-water to give the title compound as an amorphous solid, 100 mg (23%), M.p. 158° C. (dec.). Est'd purity 90% (based on HPLC).

*R. Bucourt et al., Tetrahedron 34, 2233 (1978)

IR: $\nu_{max}$ (KBr) in cm$^{-1}$ 3600–2600, 1765, 1660, 1620, 1530, 1385, 1355, 1035.

UV: $\lambda_{max}$ (MeOH) in nm (ε) 235 (16100), 286 (13800).

NMR: δ (D$_2$O+NaHCO$_3$) in ppm 1.45 (3H, t, J=7 Hz), 1.77 (3H, d, J=6 Hz), 3.45 and 3.75 (2H, ABq, J=18 Hz), 4.40 (2H, q, J=7 Hz), 5.40 (1H, d, J=5 Hz), 5.75–6.20 (3H, m), 7.13 (1H, s).

EXAMPLE 30

7-[(Z)-2-(2-Aminothiazol-4-yl)-2-cyclopropylmethoxyiminoacetamido]-3-((Z)-1-propenyl)-3-cephem-4-carboxylic acid

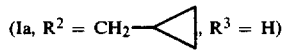

To a solution of (Z)-2-(2-N-tritylaminothiazol-4-yl)-2-cyclopropylmethyliminoacetic acid*

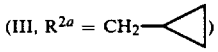

(484 mg, 1.0 m mole) and 1-hydroxybenzotriazole (135 mg, 1.0 m mole) in a mixture of dichloromethane (20 ml) and tetrahydrofuran (7 ml) at room temperature was added dicyclohexylcarbodiimide (210 mg, 1.0 m mole). The mixture was stirred for 80 min, filtered and the filtrate was concentrated to dryness. The residue was dissolved in tetrahydrofuran (10 ml) and diphenylmethyl 3-propenyl-3-cephem-4-carboxylate hydrochloride (XIII, R$^3$=H) (443 mg, 1.0 m mole) and sodium bicarbonate (84 mg, 1.0 m mole) were added. Water (10 drops) was added and the resulting solution was stirred at room temperature for 12 hr. The reaction mixture was diluted with ether and filtered. The filtrate was concentrated to give an oil. The oil was chromatographed on silica gel (230–400 mesh), eluting with 2:1 hexane-ethyl acetate to give the acylation product

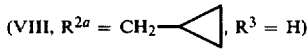

(500 mg). This was dissolved in formic acid (2.0 ml), stirred vigorously for 60 min at room temperature and 12N HCl (50 μl) was added. The mixture was stirred at room temperature for 3 hr, diluted with water (2 ml) and toluene (20 ml) and evaporated at 30° C. to dryness. The residue was triturated with isopropyl ether and the resulting precipitates were collected and washed with isopropyl ether. The solid was chromatographed on C-18 silica gel, eluting with 4:6 methanol-water to give the title compound as an amorphous solid, 80 mg (19%), M.p. 150° C. (dec.). Est'd purity 85% (based on HPLC).

*Glaxo, Japan Kokai No. 59-106492 (6/20/84)

IR: $\nu_{max}$ (KBr) in cm$^{-1}$ 3600–2600, 1765, 1660, 1620, 1530, 1350,1025, 1010.

UV: $\lambda_{max}$ (MeOH) in nm (ε) 236 (17200), 286 (14400).

NMR: δ (D$_2$O+NaHCO$_3$) in ppm 0.25–0.85 (4H, m), 1.20–1.60 (1H, m), 1.75 (3H, d, J=6 Hz), 3.45 and 3.75 (2H, ABq, J=18 Hz), 4.17 (2H, d, J=7 Hz), 5.40 (1H, d, J=5 Hz), 5.75–6.20 (3H, m), 7.14 (1H, s).

EXAMPLE 31

Diphenylmethyl 7-[2-(2-tritylaminothiazol-4-yl)-2-(propargyloxyiminoacetamido)]-3-((Z)-1-propenyl)-3-cephem-4-carboxylate (VIII, R$^{2a}$=CH$_2$C≡CH, R$^3$=H To a cooled solution of 750 mg (1.65 m moles) of diphenylmethyl 7-amino-3-[(Z)-1-propenyl]-3-cephem-4-carboxylate hydrochloride (XIII, R$^3$=H) and 1.05 ml (5 m moles) of N,O-bis(trimethylsilyl)acetamide in 17 ml of dry methlene chloride was added a solution of 750 mg (1.65 m moles) of 2-tritylaminothiazol-4-yl-2-(2-propargyloxyimino)acetic acid* (III, R$^{2a}$=CH$_2$C≡CH) and 415 mg (2.0 m moles) of phosphorus pentachloride in 17 ml of dry methylene chloride, and the mixture was stirred for 1 hr at room temperature. The reaction mixture was poured into an aqueous NaHCO$_3$ solution (30 ml) and diluted with 60 ml of ethyl acetate. The organic layer was washed with water (30 ml×2) and brine (20 ml), dried over MgSO$_4$ and concentrated under reduced pressure. The oily residue was chromatographed on a column of silica gel (Wako gel-200, 20 g) which was eluted with CHCl$_3$. Fractions containing the desired product were combined and concentrated under reduced pressure to give 90.5 mg (97%) of the title compound. M.p. 155° C. (dec.).
*U.S. Pat. No. 4,294,960 (10/13/81)

IR: $\nu_{max}$ (KBr) in cm$^{-1}$ 3280, 2120, 1780, 1720, 1670.

EXAMPLE 32

7-[(Z)-2-(2-Aminothiazol-4-yl)-2-(propargyloxyiminoacetamido)]-3-[(Z)-1-propenyl]-3-cephem-4-carboxylic acid (Ia, R$^2$=CH$_2$C≡CH, R$^3$=H)

A solution of 900 mg (1.18 m moles) of VIII (R$^{2a}$=CH$_2$C≡CH, R$^3$=H) in 3 ml of 85% formic acid was stirred at room temperature for one hour. To the reaction mixture was added 0.3 ml of conc. HCl and the suspension was stirred for 4 hr at ambient temperature. The mixture was filtered and washed with a small portion of formic acid and concentrated under reduced pressure. The residue was chromatographed on a column of reverse phase silica gel which was taken out of a PrepPAK-500/C$_{18}$ cartridge column (Waters). The column was eluted with water and 30% MeOH-water, successively. Fractions containing the desired product were combined and lyophilized to afford 105 mg (22%) of the title compound.

IR: $\nu_{max}$ (KBr) in cm$^{-1}$ 3400, 3280, 1770, 1670, 1630.

UV: $\lambda_{max}$ (pH 7 phosphate buffer) in nm ($\epsilon$) 229 (17000), 285 (14200).

NMR: $\delta$(D$_2$O+NaHCO$_3$) in ppm 1.75 (3H, d, J=6 Hz, CH=CH—CH$_3$), 3.61 (2H, ABq, 2-H), 4.98 (2H, s, O-CH$_2$—C≡CH), 5.39 (1H, d, J=5 Hz, 6-H), 5.80 (1H, m, CH=CH—CH$_3$), 5.92 (1H, d, J=5 Hz, 7-H), 6.08 (1H, d, J=11 Hz, CH=CHCH$_3$), 7.22 (1H, s, thiazole-5H).

EXAMPLE 33

Diphenylmethyl 7-[(Z)-2-(2-tritylaminothiazol-4-yl)-2-trityloxyiminoacetamido]-3-((Z)-1-propenyl)-3-cephem-4-carboxylate (VIII, R$^{2a}$=Tr, R$^3$=H)

To a mixture of 2-(2-tritylaminothiazol-4-yl)-2-(Z)-trityloxyiminoacetic acid (III, R$^{2a}$=Tr) (873 mg, 1.30 m moles) and dichloromethane (5 ml) was added phosphorus pentachloride (297 mg, 1.43 m moles) at −5° C. The mixture was allowed to stand for 20 min at the same temperature and added dropwise to a solution of diphenylmethyl 7-amino-3-(1-propenyl)-3-cephem-4-carboxylate hydrochloride (XIII, R$^3$=H: 443 mg, 1 m mole) and N,O-bis(trimethylsilyl)acetamide (0.74 ml, 4.4 m moles) in dichloromethane (5 ml) at −5° C. The reaction mixture was allowed to stand for 20 min. at the same temperature and poured into ice-water. Extraction of the mixture with ethyl acetate and evaporation of the extracts under reduced pressure gave the crude product as an oil, which was chromatographed on a column of silica gel (eluted with chloroform) to give the title compound as an amorphous powder. Yield 510 mg (48%).

IR: $\nu_{max}$ (nujol) in cm$^{-1}$ 1780, 1720, 1680.
*R. Bucourt et al., Tetrahedron 34, 2233 (1978)

EXAMPLE 34

7-[(Z)-B 2-(2-Aminothiazol-4-yl)-2-hydroxyiminoacetamido]-3-[(Z)-1-propenyl]-3-cephem-4-carboxylic acid (Ia. R$^2$=R$^3$=H)

A mixture of VIII (R$^{2a}$=Tr, R$^3$=H) (810 mg, 0.76 m mole) and 85% formic acid (2 ml) was stirred for 1 hr at room temperature. To the reaction mixture was added hydrochloric acid (0.1 ml). The mixture being stirred for 2 hr and evaporated under reduced pressure, the residue was triturated with isopropyl ether to give the crude product, which was chromatographed on a column of C-18 silica gel (eluted with 20% aq. MeOH). The eluate was concentrated under reduced pressure and freeze-dried to give the title compound as an amorphous powder. Yield 109 mg (35%). M.p. 170° C. (dec.). Est'd purity 75%.

IR: $\nu_{max}$ (KBr) in cm$^{-1}$ 1770, 1760, 1630.

UV: $\lambda_{max}$ (pH 7 phosphate buffer) in nm (E$_{1\ cm}^{1\%}$) 225 (450), 282 (370).

NMR: $\delta$(D$_2$O+NaHCO$_3$) in ppm 1.78 (3H, d, J=6 Hz, CH=CH—CH$_3$), 3.64 (2H, ABq, J=18 Hz, 2-H), 5.40 (1H, d, J=4 Hz, 6-H), 5.70–6.25 (3H, m, 7-H, vinyl-H), 7.14 (1H, d, thiazole-H).

EXAMPLE 35

1-Acetoxyethyl 7-[(Z)-2-(2-aminothiazol-4-yl)-2-hydroxyiminoacetamido]-3-[(Z)-1-propenyl]-3-cephem-4-carboxylate (Ib, R$^2$=R$^3$=H, R$^4$=AX)

To an ice-cooled and stirred solution of Ia (R$^2$=R$^3$=H, Example 34) (270 mg, 0.66 m mole) in dry DMF (2 ml) were added sodium carbonate (105 mg, 0.99 m mol) and a solution of 1-acetoxyethyl bromide (397 mg, 2.38 m mol) in DMF (0.6 ml) in three portions at 15-minute intervals. The reaction was monitored by TLC (Merck Kieselgel 60F$_{254}$, 10:1 MeCN—H$_2$O). The mixture was stirred for additional 30 minutes, showing three major spots at Rf 0.11, 0.58 and 0.75. After dilution with ethyl acetate (50 ml), the resulting precipitate was filtered off, and the filtrate washed with water (×3) and subsequently with saturated aqueous sodium chloride, and dried over magnesium sulfate. The filtrate was evaporated to dryness in vacuo and the residue was dissolved in a small amount of chloroform. The solution was chromatographed on a Kieselgel 60 column (20 g), which was eluted with CHCl$_3$ and then with a 1:20 mixture of MeOH and CHCl$_3$. Fractions showing a spot at Rf 0.58 by TLC were combined and concentrated to a small volume. To the concentrate was added isopropyl ether to give a precipitate, which was collected by filtration to afford 61 mg (19%) of the desired acetoxyethyl ester. M.p. 120°–125° C. Estimated purity 75% by HPLC.*
*Packing: TSK gel 120 T (4×250 mm) Mobile phase: CH$_3$CN/pH 6 phosphate buffer (≴)

IR: $\nu_{max}$ (KBr) in cm$^{-1}$ 1765, 1665, 1610, 1530, 1375.

UV: $\lambda_{max}$ (EtOH) in nm ($\epsilon$) 223 (19000), 264 (12000), 285 (12000).

NMR: $\delta$(CDCl$_3$) in ppm 1.50 (3H, d, J=5.0 Hz, CHCH$_3$), 1.65 (3H, d, J=6.0 Hz, =CHCH$_3$), 2.07 (3H, s, COCH$_3$), 3.45 (2H, br, SCH$_2$), 5.08 (1H, d, J=5.5 Hz, 6-H), 5.5–6.0 (2H, m, 7-H & =CH), 6.15 (1H, d, J=10 Hz, 3-CH=), 6.96 (2H, m, thiazole-H & OCHCH$_3$).

EXAMPLE 36

1-Acetoxyethyl 7-[(Z)-2-(2-Aminothiazol-4-yl)-2-acetoxyiminoacetamido]-3-[(Z)-1-propenyl]-3-cephem-4-carboxylate (Ib, R$^2$=Ac, R$^3$=H, R$^4$=AX)

To a stirred mixture of Ia (R$^2$=R$^3$=H) (200 mg, 0.49 m mole) and K$_2$CO$_3$ (34 mg, 0.24 m mole) in dry DMF (5 ml) was added at 0° C. a solution of 1-acetoxyethyl bromide (81 mg, 0.49 m mole) in dry DMF (0.1 ml).

Potassium carbonate and the bromide were added to the mixture additional 4 times at 45-minute intervals. The reaction mixture was monitored by HPLC (Lichrosorb RP-18 4×300 mm, 4:1 MeCN—H$_2$O). After the addition, the mixture was stirred for 30 min. The reaction mixture showing a major peak at 4.5 min (retention time) was diluted with AcOEt (40 ml), washed with water (×3) and a saturated NaCl solution, dried over MgSO$_4$ and evaporated to a small volume. The concentrate was chromatographed on a Kieselgel 60 (8 g) column by eluting with a 1:20 mixture of MeOH—CHCl$_3$. The eluate was monitored by HPLC and the fractions showing a peak of a retention time at 4.5 min were combined and concentrated to ca. 2 ml. To the concentrate was added isopropyl ether (20 ml) to give 190 mg (72%) of the title compound as an isopropyl ether solvate. Est'd purity 85%.

IR: $\nu_{max}$ (KBr) in cm$^{-1}$ 3280 (w), 1770 (s), 1680 (m), 1540 (m), 1215 (s).

UV: $\lambda_{max}$ (MeOH) in nm ($\epsilon$) 231 (17600), 293 (9800).

NMR: $\delta$(CDCl$_3$+D$_2$O) in ppm 1.5 (3H, d, J=6 Hz, OCHCH$_3$), 1.65 (3H, d—d, J=7 & 1 Hz, =CHCH$_3$), 2.05 (3H, s, COCH$_3$), 2.2 (3H, s, COCH$_3$), 3.44 (2H, br, SCH$_2$), 5.1 (1H, d, J=5 Hz, 6-H), 5.5–6.0 (1H, m, 3-CH=CH), 5.9 (1H, d, J=5 Hz, 7-H), 6.15 (1H, d, J=11 Hz, 3-CH=CH), 6.89 (1H, m, OCHCH$_3$), 6.92 (1H, s, thiazole-H).

Anal. Calcd. for C$_{21}$H$_{23}$N$_5$O$_8$S$_2$.4/5[(CH$_3$)$_2$CH]$_2$O: C, 50.04; H, 5.57; N, 11.31; S, 10.35. Found: C, 49.78; H, 5.47; N, 10.90; S, 10.28.

Example 37

7-[(Z)-2-(2-Aminothiazol-4-yl)-2-(acetyloxyiminoacetamido)]-3-[(Z)-1-propenyl]-3-cephem-4-carboxylic acid (Ia, R$^2$=Ac, R$^3$=H)

A suspension of 200 mg (1.30 m moles) of 1-hydroxy-1H-benzotriazole monohydrate, 631 mg (1.30 m moles) of 2-(2-tritylaminothiazol-4-yl)-2-acetoxyimino acetic acid* and 268 mg (1.30 m moles) of dicyclohexylcarbodiimide was stirred for 1 hr at 5° C. To the mixture was added 510 mg (1.26 m moles) of diphenylmethyl 7-amino-3-[(Z)-1-propenyl]-3-cephem-4-carboxylate. The mixture was stirred for 5 hr at room temperature and diluted with 50 ml of AcOEt. The reaction mixture was washed with 1N HCl (25 ml), water (25 ml) and brine (25 ml), dried over MgSO$_4$, and concentrated under diminished pressure. The residue was chromatographed on a column of silica gel (30 g) which was eluted with toluene-AcOEt (10/1). Fractions showing a spot at Rf 0.20 by TLC (10:1 toluene-AcOEt) were combined and evaporated in vacuo. The residual oil (ca. 1.15 g) was dissolved in a mixture of 8 ml of 95% TFA and 2 ml of anisole and the mixture was stirred for 1 hr in an ice-bath. The solution was concentrated under reduced pressure and triturated with isopropyl ether (40 ml) and n-hexane (10 ml) to give 432 mg of the crude product, which was purified by a column of Bondapak C-18, eluted with 30% aqueous MeOH. Fractions showing a peak of retention time 6.9 min. (HPLC) were combined, concentrated and lyophilized to give 153 mg (27%) of the title compound as an amorphous powder. M.p. 155° C. (dec.). Estimated purity 65%. HPLC (Lichrosorb RP-18 4×300 mm, 3:7 MeOH-pH 7 buffer); retention time, 6.9 min.
*Japan Kokai No. 59-184 186 (10/19/84, Meiji Seika)

IR: $\nu_{max}$ (KBr) in cm$^{-1}$ 3260, 1775, 1765, 1665.

UV: $\lambda_{max}$ (EtOH) in nm ($\epsilon$) 230 (20100), 292 (12700).

NMR: $\delta$(DMSO-d$_6$) in ppm 1.63 (3H, dd, J=1 & 7 Hz, =CHCH$_3$), 2.16 (3H, s, OAc), 3.55 (br.s, 2H, 2-H), 5.22 (1H, d, J=5 Hz, 6-H), 5.70 (1H, m, =CHCH$_3$), 5.76 (1H, dd, J=5 & 8 Hz, 7-H), 6.10 (1H, d, J=11 Hz, 3-CH=CH—), 7.05 (1H, s, thiazole-H), 7.28 (2H, s, —NH$_2$), 9.80 (1H, d, J=8 Hz).

EXAMPLE 38

1-Acetoxyethyl 7-[(Z)-2-(2-aminothiazol-4-yl)-2-acetoxyiminoacetamido]-3-[(Z)-1-propenyl]-3-cephem-4-carboxylate (Ib, R$^2$=AC, R$^3$=H, R$^4$=AX)

To a solution of 20 mg (0.05 m mole) of Ia (R$^2$=AC, R$^3$=H) in 0.2 ml of dry DMF was added 6 mg (0.05 m mole) of K$_2$CO$_3$ and the mixture was stirred for 5 minutes at 5° C. 1-Acetoxyethyl bromide (10 μl) was added to the mixture and the suspension was stirred for 1 hr at the same temperature. The reaction mixture was diluted with 5 ml of AcOEt, washed successively with water (2 ml×3) and brine, dried over MgSO$_4$ and concentrated under reduced pressure. The residue was triturated with 10 ml of isopropyl ether to give the desired acetoxyethyl ester, which was filtered off and dried. Yield 15 mg (63%). Spectral data of the product were consistent with those of the compound prepared in Example 36.

EXAMPLE 39

Pivaloyloxymethyl 7-[(Z)-2-(2-aminothiazol-4-yl)-2-hydroxyiminoacetmido]-3-[(Z)-1-propenyl]-3-cephem-4-carboxylate (Ib, R$^2$=R$^3$=H, R$^4$=PV)

To a stirred mixture of Ib (R$^2$=R$^3$=H) (200 mg, 0.49 m mole) and Na$_2$CO$_3$ (26 mg, 0.24 m mole) in dry dimethylacetamide (5 ml) was added at −5° C. pivaloyloxymethyl iodide (118 mg, 0.49 m mole) and the mixture was stirred for 45 min. Sodium carbonate (13 mg, 0.12 m mole) and the iodide (59 mg, 0.12 m mole) were added again to the mixture and the mixture was stirred at the same temperature. After 30 min., the mixture showing spots at Rf 0.60 (major), 0.70 (minor) and 0.80 (minor) by TLC (Merck Kieselgel 60 F$_{254}$, 20:1 MeCN—H$_2$O) was diluted with ethyl acetate (25 ml) and the solution was washed with water (×3) and a saturated NaCl solution, dried over MgSO$_4$ and evaporated to dryness. The residue was dissolved in a small amount of CHCl$_3$ and passed through a column of Kieselgel 60 (13 g), which was washed with CHCl$_3$ (50 ml) and eluted with 1:20 MeOH—CHCl$_3$ (150 ml). The fractions showing a spot at Rf 0.60 by TLC were combined and evaporated. The residue was dissolved in benzene and the solution was lyophilized to afford 63 mg (25%) of the title compound. M.p. 101°–104° C. Estimated purity 80%. HPLC (Develosil 4×100 mm, 3:2 MeCN—pH 7 phosphate buffer): retention time, 4.6 min.

IR: $\nu_{max}$ (KBr) in cm$^{-1}$ 1780, 1755, 1670, 1530, 1120.

UV: $\lambda_{max}$ (MeOH) in nm ($\epsilon$) 270 (12000).

NMR: $\delta$(CDCl$_3$+D$_2$O) in ppm 1.22 (9H, s, 3×CH$_3$), 1.56 (3H, dd, J=1 & 7 Hz, =CHCH$_3$), 3.45 (2H, m, S—CH$_2$) 5.11 (1H, d, J=4 Hz, 6-H), 5.5–5.95 (4H, m, 7-H, =CHCH$_3$ & OCH$_2$O), 6.14 (1H, d, J=11 Hz, 3-CH=), 7.02 (1H, s, thiazole-H).

EXAMPLE 40

Acetoxymethyl 7-[(Z)-2-(2-aminothiazol-4-yl)-2-hydroxyiminoacetamido]-3-[(Z)-1-propenyl]-3-cephem-4-carboxylate (Ib, $R^2=R^3=H$, $R^4=AM^*$)

*AM = —CH$_2$OCOCH$_3$

To a stirred suspension of Ia ($R^2=R^3=H$) (280 mg, 0.68 m mole) and Na$_2$CO$_3$ (36 mg, 0.34 m mole) in dry DMF (5 ml) was added at $-10°$ C. over 10 min. a solution of acetoxymethyl bromide in dry DMF (104 mg, 0.68 m mole/100 µl). After 30 min, additional Na$_2$CO$_3$ (18 mg, 0.17 m mole) and the bromide solution (52 mg, 0.34 m mole/50 µl) were added in small portions over 10 min. The mixture was stirred at the same temperature for 30 min. The reaction mixture showing four spots at Rf 0.10 (BMY-28232), 0.15, 0.60 and 0.75 by TLC (Merck Kieselgel 60 F$_{254}$, 10:1 MeCN—H$_2$O) was diluted with AcOEt (25 ml), washed with water ($\times$3) and a saturated NaCl solution, dried over MgSO$_4$ and evaporated. The residue was dissolved in a small amount of CHCl$_3$ and charged on a column of Kieselgel 60 (18 g), which was washed with CHCl$_3$ (50 ml) and eluted with MeOH—CHCl$_3$ (1:20, 250 ml). The fractions showing a spot at Rf 0.60 by TLC were combined and evaporated in vacuo. The residue was dissolved in benzene and lyophilized to afford 45 mg (14%) of the title compound. M.p. 107–110° C. Estimated purity 70%. HPLC (Lichrosorb 4×300 mm, 2:3 MeCN—H$_2$O): retention time, 6.0 min.

IR: $\nu_{max}$ (KBr) in cm$^{-1}$ 1770, 1665, 1530, 1370, 1200, 1000, 985.

UV: $\lambda_{max}$ (MeOH) in nm ($\epsilon$) 268 (10900).

NMR: $\delta$(CDCl$_3$+D$_2$O) in ppm 1.65 (3H, s, J=7 Hz, =CHC$\underline{H}$$_3$), 2.1 (3H, s, COCH$_3$), 3.43 (2H, br, SCH$_2$), 5.1 (1$\overline{H}$, d, J=5 Hz, 6-H), 5.3–5.95 (4H, m, 7-H, =C$\underline{H}$CH$_3$ & OCH$_2$O), 6.15 (1H, d, J=11 Hz, 3-CH=), 6.96 (1H, s, thiazole-H).

EXAMPLE 41

Diphenylmethyl 7-amino-3-[(E)-1-butenyl]-3-cephem-4-carboxylate hydrochloride (XIII (E), $R^3=CH_3$, $R^{4a}=CHPh_2$)

A mixture of diphenylmethyl 7-amino-3-[(Z)-1-butenyl]-3-cephem-4-carboxylate hydrochloride (from Example 6) (2.9 g, 6.5 m moles) and benzophenone (1.2 g, 6.5 m moles) in methanol (300 ml) was irradiated with a low pressure Hg lamp (2537 Å, 6 W) at room temperature for 26 hr. The solvent was evaporated in vacuo and the residue was dissolved in chloroform. The solution was treated with carbon and filtered. The filtrate was diluted with ether to precipitate 2.2 g (76%) of the title compound E isomer contaminated with 10% of the Z isomer which was used for the next step without further purification.

IR: $\nu_{max}$ (KBr) in cm$^{-1}$ 1780, 1720, 1625.

UV: $\lambda_{max}$ (MeOH) in nm ($\epsilon$) 298 (10200).

NMR: $\delta$(DMSO-d$_6$) in ppm 0.97 (3H, t, J=7 Hz, CH$_3$), 2.15 (2H, m, C$\underline{H}$$_2$CH$_3$), 3.84 (2H, br-s, 2-H), 5.15 (1H, d, J=5 Hz, 6-H)$\overline{,}$ 5.30 (1H, d, J=5 Hz, 7-H), 6.65 (1H, d, J=16 Hz, 3-CH=), 6.97 (1H, s, OCH), 7.45 (10H, s, phenyl-H).

HPCL: Lichrosorb RP-18 (4×250 mm), 3:2 CH$_3$CN- pH 7 phosphate buffer, 2 ml/min. Retention time: Z isomer, 5.1 min; E isomer, 6.7 min.

EXAMPLE 42

Diphenylmethyl 7-[(Z)-2-(2-aminothiazol-4-yl)-2-methoxyiminoacetamido]-3-[(E)-1-butenyl]-3-cephem-4-carboxylate (XIV (E), $R^2=R^3=CH_3$, $R^{4a}=CHPh_2$)

A suspension of crude diphenylmethyl 7-amino-3-[(E)-1-butenyl]-3-cephem-4-carboxylate hydrochloride (1.97 g, 4.3 m moles) in AcOEt (30 ml) was shaken with aqueous NaHCO$_3$ to give a clear two-layer solution. The organic layer was separated, washed with water and then an aqueous saturated NaCl solution, dried over MgSO$_4$ and concentrated in vacuo. The residue was dissolved in DMF (20 ml). To the solution was added 1-[(Z)-2-(2-aminothiazol-4-yl)-2-methoxyiminoacetoxy]benzotriazole (2.07 g, 6.5 m moles). The mixture was stirred at room temperature for 1 hr and diluted with AcOEt (100 ml). The diluted solution was washed with aqueous NaHCO$_3$, water and aqueous NaCl, successively, dried over MgSO$_4$ and evaporated in vacuo. The residue was chromatographed on a silica gel column (50 g) and eluted with 2:1 toluene-ethyl acetate to yield 1.58 g (61%) of the title compound.

IR: $\nu_{max}$ (KBr) in cm$^{-1}$ 1770, 1720, 1670.

UV: $\lambda_{max}$ (MeOH) in nm ($\epsilon$) 297 (18800).

NMR: $\delta$(CDCl$_3$+D$_2$O) in ppm 0.97 (3H, t, J=7 Hz, CH$_2$C$\underline{H}$$_3$), 2.12 (2H, m, C$\underline{H}$$_2$CH$_3$), 3.52 (2H, s, 2-H), 4.00 (3$\overline{H}$, s, OCH$_3$), 5.10 (1$\overline{H}$, d, J=4.5 Hz, 6-H), 5.93 (1H, d, J=4.5 Hz, 7-H), 5.7–6.3 (1H, m, =C$\underline{H}$—CH$_2$), 6.74 (1H, s, thiazole-H), 6.96 (1H, s, OCH), 7.25 (10H, s, phenyl-H).

EXAMPLE 43

7-[(Z)-2-(2-Aminothiazol-4-yl)-2-methoxyiminoacetamido]-3-[(E)-1-butenyl]-3-cephem-4-carboxylic acid (Ia (E), $R^2=R^3=CH_3$)

A mixture of diphenylmethyl 7-[(Z)-2-(2-aminothiazol-4-yl)-2-methoxyiminoacetamido]-3-[(E)-1-butenyl]-3-cephem-4-carboxylate (650 mg, 1.1 m moles), TFA (3ml) and anisole (1 ml) was stirred at 5° C. for 30 min and diluted with isopropyl ether. The resulting precipitate was collected by filtration. It was dissolved in formic acid (3 ml) and chromatographed on a column of the packing (100 ml) of a PrepPAK cartridge (Waters), which was washed with water and then eluted with 30% methanol. The eluate was monitored by HPLC and the desired fractions were combined, concentrated and lyophilized to give 277 mg (59%) of the title compound*. M.p.>170° C. (grad. dec.). Estimated purity 90%.

*The 3-trans-butenyl cephalosporin Ia (E, $R^2=R^3=CH_3$), which was identical with that described in Example 15.

IR: $\nu_{max}$ (KBr) in cm$^{-1}$ 1770, 1660.

UV: $\lambda_{max}$ (pH 7 phosphate buffer) in nm ($\epsilon$) 232 (15700), 292 (22400).

NMR: $\delta$(D$_2$O+NaHCO$_3$) in ppm 1.18 (3H, t, J=7 Hz, CH$_2$C$\underline{H}$$_3$), 2.30 (2H, m, C$\underline{H}$$_2$CH$_3$), 3.83 (2H, s, 2-H), 4.15 (3$\overline{H}$, s, OCH$_3$), 5.37 (1$\overline{H}$, d, J=5 Hz, 6-H), 5.92 (1H, d, J=5 Hz, 7-H), 5.9–6.4 (1H, m, =C$\underline{H}$CH$_2$), 5.66 (1H, d, J=16 Hz, 3-CH=), 7.18 (1H, s, thiazole-H).

Anal. Calcd. for C$_{17}$H$_{19}$N$_5$O$_5$S$_2$. ½H$_2$O: C, 45.73; H, 4.51; N, 15.69; S, 14.36. Found: C, 45.63; H, 4.28; N, 15.33; S, 14.27.

EXAMPLE 44

1-Acetoxyethyl 7-[(Z)-2-(2-aminothiazol-4-yl)-2-methoxyiminoacetamido]-3-[(E)-1-butenyl]-3-cephem-4-carboxylate (Ib (E), $R^2=R^3=CH_3$, $R^4=AX$)

A mixture of Ia (E) ($R^2=R^3=CH_3$) (438 mg, 1 m mole) and $K_2CO_3$ (207 mg, 1.5 m moles) in DMF (10 ml) was treated with 1-acetoxyethyl bromide (250 mg, 1.5 m moles) by a similar procedure to that described in Example 16 to give 350 mg (67%) of the desired AX ester, which was identical with that in Example 16. M.p. 110°-115° C. Estimated purity, 90% by HPLC.

IR: $\nu_{max}$ (KBr) in cm$^{-1}$ 1760 (br.), 1670, 1610.

UV: $\lambda_{max}$ (MeOH) in nm ($\epsilon$) 232 (16600), 298 (19300).

NMR: $\delta$(CDCl$_3$) in ppm 1.05 (3H, t, J=7 Hz, CH$_2$CH$_3$), 1.54 (3H, d, J=6 Hz, CHCH$_3$), 2.08 (3H, s, COCH$_3$), 2.0-2.4 (2H, m, —CH$_2$CH$_3$), 3.57 (2H, s, 2-H), 4.05 (3H, s, OCH$_3$), 5.07 (1H, d, J=5 Hz, 6-H), 5.8-6.3 (2H, m, 7H & =CHCH$_2$—), 6.86 (1H, s, thiazole-H), 6.8-7.1 (2H, m, OCH & 3-CH=)

Anal. Calcd. for C$_{21}$H$_{25}$N$_5$O$_7$S$_2$.¼[(CH$_3$)$_2$CH]$_2$O : C, 49.21; H, 5.23; N, 12.75; S, 11.68. Found: C, 49.44; H, 5.28; N, 12.24; S, 11.70.

EXAMPLE 45

7-Amino-3-[(E)-1-propenyl]-3-cephem-4-carboxylic acid (XIII (E), $R^3=R^{4a}=H$)

A solution of 7-amino-3-[(Z)-1-propenyl]-3-cephem-4-carboxylic acid* (1.2 g, 5 m moles) and benzophenone (900 mg, 5 m moles) in methanol (800 ml) containing 1 ml of 6N hydrochloric acid was irradiated with low-pressure Hg lamp (2537 Å, 6 W) at room temperature for 44 hrs. The reaction mixture was evaporated to dryness and the residue was distributed in a mixture of 0.15N HCl (200 ml) and ether (200 ml). The aqueous layer was separated, treated with active carbon and filtered. The filtrate was adjusted to pH 3 with a dilute NaOH solution and cooled to give a precipitate. It was collected by filtration and washed with water and acetone to give 476 mg of the title compound E isomer, melting at 245° C. (grad. dec.). The second crop (195 mg) was obtained by concentrating the filtrate to 30 ml. Total yield 671 mg (56%). The product contained less than 5% of the corresponding Z isomer.

*A 4:1-mixture of Z and E isomers.

IR: $\nu_{max}$ (KBr) in cm$^{-1}$ 1800, 1620, 1540, 1420, 1360.

UV: $\lambda_{max}$ (pH 7 phosphate buffer) in nm ($\epsilon$) 292 (15000).

NMR: $\delta$(D$_2$O+Na$_2$CO$_3$) in ppm 1.78 (3H, d, J=6 Hz, =CH—CH$_3$), 3.62 (2H, s, 2-H), 5.03 (1H, d, J=4.5 Hz, 6-H), 5.3-6.2 (2H, m, =CH & 7-H), 6.52 (1H, d, J=16 Hz, 3-CH=C).

Anal. Calcd. for C$_{10}$H$_{12}$N$_2$O$_3$S.½H$_2$O: C, 48.18; H, 5.25; N, 11.24; S, 12.86. Found: C, 47.88; H, 4.83; N, 10.79; S, 12.83.

EXAMPLE 46

7-[(Z)-2-(2-Aminothiazol-4-yl)-2-methoxyiminoacetamido]-3-[(E)-1-propenyl]-3-cephem-4-carboxylic acid (Ia (E), $R^2=CH_3$, $R^3=H$)

To a stirred solution of 7-amino-3-trans-propenyl derivatives XIII (E, $R^3=R^{4a}=H$) (720 mg, 3 m moles) and sodium bicarbonate (504 mg, 6 m moles) in 50% DMF (60 ml) was added 1-[(Z)-2-(2-aminothiazol-4-yl)-2-methoxyiminoacetoxy]benzotriazole (954 mg, 3 m moles) and the mixture was stirred for 30 min. An additional amount of the active ester (1.81 g, 6 m moles) was added in four portions at 30-min intervals. The mixture was stirred for additional 2 hr at room temperature and passed through a column packed with the packing of prepPAK-C$_{18}$ cartridge (300 ml, Waters). The column was washed with water and then eluted successively with 10% methanol and 20% methanol. Fractions of 20% methanol eluate showing a peak at retention time 5.57 min by HPLC* were collected and evaporated to dryness. The residue was dissolved in methanol and filtered. The filtrate was concentrated to 5 ml and the residue was triturated with a mixture of ether-isopropyl ether to give 805 mg (63%) of the title compound, melting at 180° C. (grad. dec.), 80% pure by HPLC*.

*Packing: Lichrosorb RP-18 (4×300 mm), Mobile phase: MeOH-pH 7 buffer (35:65).

IR: $\nu_{max}$ (KBr) in cm$^{-1}$ 1770, 1670, 1630, 1540, 1380, 1040.

UV: $\lambda_{max}$ (MeOH) in nm ($\epsilon$) 234 (17000), 293 (20000).

NMR: $\delta$(D$_2$O+Na$_2$CO$_3$) in ppm 1.93 (3H, d—d, J=6 & 1.5 Hz, =CH—CH$_3$). 3.76 (2H, s, 2-H), 4.12 (3H, s, OCH$_3$), 5.32 (1H, d, J=4.5 Hz, 6-H), 5.86 (1H, d, J=4.5 Hz, 7-H), 5.8-6.3 (1H, m, =CH—CH$_3$), 6.61 (1H, d—d, J=16 & 1.5 Hz, CH=C), 7.13 (1H, s, thiazole-H).

Anal. Calcd. for C$_{16}$H$_{17}$N$_5$O$_5$S$_2$: C, 45.38; H, 4.05; N, 16.54; S, 15.14. Found: C, 45.57, 45.41; H, 4.37, 4.29; N, 15.94, 15.76; S, 13.90, 13.62.

EXAMPLE 47

1-Acetoxyethyl 7-[(Z)-2-(2-aminothiazol-4-yl)-2-methoxyiminoacetamido]-3-[(E)-1-propenyl]-3-cepehm-4-carboxylate (Ib (E), $R^2=CH_3$, $R^3=H$, $R^4=AX$)

To a stirred mixture of 317 mg (0.75 m mole) of the trans-propenyl cephalosporin Ia (E, $R^2=CH_3$, $R^3=H$) and 104 mg (0.75 m mole) of potassium carbonate in 5 ml of DMF was added at 0°-5° C. a solution of 167 mg (1 m mole) of 1-acetoxyethyl bromide in 0.5 ml of DMF and the mixture was stirred at 5° C. for 15 min. An additional amount of each of potassium carbonate (204 mg, 1.5 m moles) and the bromide solution in DMF (334 mg, 2 m moles/1 ml) was added in two portions over a period of 15 min to complete the reaction. The mixture was stirred at 5° C. for additional 30 min and diluted with 150 ml of ethyl acetate. The dilute solution was washed with water and aqueous NaCl, dried with MgSO$_4$, and concentrated to dryness. The oily residue was dissolved in a small volume of CHCl$_3$ and chromatographed on a silica gel column (Merck Kieselgel 60, 40 g), which was washed with chloroform and eluted with chloroform-methanol (50:1). The desired fractions showing a spot at Rf 0.40 by TLC (silica gel, chloroform-methanol, 10:1) and a peak at retention time 7.7 min by HPLC (acetonitrile-pH 7 buffer, 1:1), were collected and evaporated to dryness to give an oily residue, which was triturated with a mixture of ether and isopropyl ether to give 270 mg (70.5%) of the desired title ester, melting at 140° C. (dec.). Estimated purity 80% by HPLC.

IR: $\nu_{max}$ (KBr) in cm$^{-1}$ 1770, 1670, 1620, 1540, 1380, 1210, 1100, 1070, 1040.

UV: $\lambda_{max}$ (MeOH) in nm ($\epsilon$) 234 (17000), 297 (19000).

NMR: $\delta$(CDCl$_3$) in ppm 1.53 (3H, d, J=5 Hz, C-CH$_3$), 1.86 (3H, d, J=6 Hz, CH=CH—CH$_3$), 2.08 (3H, s, OCOCH$_3$), 3.55 (2H, br-s, 2-H), 4.05 (3H, s, OCH$_3$), 5.07 (1H, d, J=4.5 Hz, 6-H), 5.38 (2H, br-s, NH$_2$), 5.95 (1H, d, J=4.5 Hz, 7-H), 5.7-6.2 (1H, m, CH=CH—CH$_3$), 6.81 (1H, s, thiazole-H), 6.9-7.1 (2H, m, CH—CH$_3$ & CH=CH—CH$_3$), 7.55 (1H, d, J=8 Hz, NH).

EXAMPLE 48

Diphenylmethyl 7-[(Z)-2-(2-tritylaminothiazol-4-yl)-2-methoxyiminoacetamido]-3-[(triphenylphosphoranylidene)methyl]-3-cephem-4-carboxylate (VII, R$^{2a}$=CH$_3$)

A solution of diphenylmethyl 7-[(Z)-2-(2-tritylaminothiazol-4-yl)-2-methoxyiminoacetamido]-3-[(triphenylphosphonio)methyl]-3-cephem-4-carboxylate iodide* (3.0 g, 2.5 m moles) in dichloromethane (40 ml) was shaken with 1N NaOH (10 ml) until the spot of the starting material disappeared on TLC (silica gel, CHCl$_3$—MeOH=10:1). Organic layer was separated and concentrated under reduced pressure. The residue was triturated with n-hexane and the product was collected by filtration to give 2.5 g (93%) of the title compound.
*U.S. Pat. No. 4,486,586, Column 33, Preparation No. 17, Compound VIII-1.

IR: $\nu_{max}$ (KBr) in cm$^{-1}$ 1760, 1740, 1560.

UV: $\lambda_{max}$ (CH$_2$Cl$_2$) in nm ($\epsilon$) 310 (8800), 388 (15000).

EXAMPLE 49

Diphenylmethyl 7-[(Z)-2-(2-tritylaminothiazol-4-yl)-2-methoxyiminoacetamido]-3-[3-(Z)-acetoxy-1-propenyl]-3-cephem-4-carboxylate (VIII, R$^{2a}$=CH$_3$, R$^3$=OAc)

A mixture of diphenylmethyl 7-[(Z)-2-(2-tritylaminothiazol-4-yl)-2-methoxyiminoacetamido]-3-(triphenylphosphoranylidene)methyl-3-cephem-4-carboxylate (2.13 g, 2.9 m moles) and acetoxyacetaldehyde$^{(1)}$ (0.61 g, 6.0 m moles) in dichloromethane (10 ml) was stirred for 3 hr at room temperature. The mixture was concentrated under reduced pressure and the residue was chromatographed on a column of silica gel. The column was eluted with n-hexane—CHCl$_3$ (1:2) and the fractions containing the desired product were combined. Evaporation of the solvent under reduced pressure afforded 1.0 g (56%) of the title compound.
*(1) J. Corbet and C. Benezra, J. Org. Chem, 46, 1141 (1981).

IR: $\nu_{max}$ (liq.) in cm$^{-1}$ 1785, 1735, 1675, 1430, 1230, 1180.

NMR: $\delta$(CDCl$_4$) in ppm 6.08 (1H, d, J=13 Hz).

EXAMPLE 50

Diphenylmethyl 7-amino-3-[(Z)-3-acetoxy-1-propenyl]-3-cephem-4-carboxylate (XIII, R$^3$=OAc)

To a cooled mixture of LiBr (8.6 g, 0.1 mole) in dry DMF (40 ml) were successively added a solution of diphenylmethyl 7-benzylideneamino-3-[(triphenylphosphoranylidene)methyl]-3-cephem-4-carboxylate (XI) (7.3 g, 10 m moles) in dry methylene chloride (200 ml) and acetoxyacetaldehyde (3.06 g, 0.03 mole), and the mixture was stirred at room temperature for 44 hrs. After concentration to 50 ml, the oily residue was diluted with ethyl acetate and the solution was washed with water, a saturated NaCl solution, dried over MgSO$_4$ and concentrated to 100 ml. To the stirred concentrate was added a solution of the Girard T reagent (5 g, 0.03 mole) in methanol (100 ml) containing 1 ml of acetic acid and the mixture was stirred at room temperature for 40 min. After evaporation of the solvent, the residue was dissolved in 300 ml of ethyl acetate and the solution was washed with sodium bicarbonate solution, water, a saturated NaCl solution and dried with MgSO$_4$. Evaporation of the solvent gave an oily residue which was chromatographed on a silica gel column (Merck Kiesel gel 60, 100 g) by eluting with chloroform. The eluate was monitored by TLC (chloroform:methanol=30:1) and the fractions showing a spot at Rf 0.30 were combined and concentrated to afford an oily residue, which was triturated with ether-isopropyl ether to give 2.8 g (60%) of the title compound, melting at 130°–135° C. (dec.)

IR: $\nu_{max}$ (KBr) in cm$^{-1}$ 1770, 1720, 1390, 1370, 1220, 1100.

UV: $\lambda_{max}$ (MeOH) in nm ($\epsilon$) 286 (7500).

NMR: $\delta$(CDCl$_3$) in ppm 1.83 (2H, br s, NH$_2$), 2.02 (3H, s, COCH$_3$), 3.27 (1H, d, J=18 Hz, 2-H), 3.65 (1H, d, J=18 Hz, 2-H), 3.9–4.9 (2H, m, CH$_2$OAc), 4.78 (1H, d, J=4.5 Hz, 6-H), 5.02 (1H, d, J=4.5 Hz, 7-H), 5.3–5.8 (1H, m, =CH—CH$_2$—), 6.27 (1H, d, J=11 Hz, CH=CH—CH$_2$), 6.97 (1H, s, CH-Ph), 7.2–7.6 (10H, m, phenyl H).

Anal. Calcd. for C$_{25}$H$_{24}$N$_2$O$_5$S: C, 64.64; H, 5.21; N, 6.03; S, 6.90. Found: C, 64.79; H, 5.33; N, 5.89; S, 6.94.

EXAMPLE 51

Diphenylmethyl 7-[(Z)-2-(2-aminothiazol-4-yl)-2-methoxyiminoacetamido]-3-[(Z)-3-acetoxy-1-propenyl]-3-cephem-4-carboxylate (XIV, R$^3$=OAc)

A mixture of diphenylmethyl 7-amino-3-[(Z)-3-acetoxy-1-propenyl]-3-cephem-4-carboxylate (2.32 g, 5 m moles) and benzotriazol-1-yl (Z)-2-(2-aminothiazol-4-yl)-2-methoxyiminoacetate (1.9 g, 6 m moles) in 100 ml of dry THF was stirred at room temperature for 20 hr and the solvent was evaporated to dryness. After extraction with ethyl acetate (200 ml), the solution was washed with aqueous sodium bicarbonate, a saturated NaCl solution and water, dried with MgSO$_4$ and concentrated to give an oily residue, which was chromatographed on a silica gel column (Kiesel gel 60, 80 g Merck), by eluting successively with chloroform and chloroform-methanol (50:1). The desired fractions eluted with chloroform-methanol (50:1) were combined and concentrated to give a residue which was triturated with ether-isopropyl ether to give 1.97 g (61%) of the title compound, melting at 120° C. (grad. dec.).

IR: $\nu_{max}$ (KBr) in cm$^{-1}$ 1780, 1730, 1670, 1610, 1530, 1370, 1220, 1030.

UV: $\lambda_{max}$ (MeOH) in nm ($\epsilon$) 286 (14000).

NMR: $\delta$(CDCl$_3$) in ppm 1.97 (3H, s, COCH$_3$), 3,42 (2H, s, 2-H), 4.02 (3H, s, OCH$_3$), 5.15 (1H, d, J=4.5 Hz, 6-H), 6.03 (1H, d-d, J=4.5 & 9 Hz, 7-H), 6.27 (1H, d, J=11 Hz, CH=CH-CH$_2$), 6.78 (1H, s, thiazole-H), 6.94 (1H, s, CHPh), 7.2–7.6 (10H, m, phenyl-H), 8.03 (1H, d, J=9 Hz, NH).

EXAMPLE 52

7-[(Z)-2-(Aminothiazol-4-yl)-2-methoxyiminoacetamido]-3-[(Z)-3-acetoxy-1-propenyl]-3-cephem-4-carboxylic acid (Ia, R$^2$=CH$_3$, R$^3$=OAc)

(A) From XIV (R$^3$=OAc)—A mixture of diphenylmethyl 7-[(Z)-2-(2-aminothiazol-4-yl)-2-methoxyiminoacetamido]-3-[(Z)-3-acetoxy-1-propenyl]-3-cephem-4-carboxylate (1.88 g, 2.9 m moles), 3 ml of anisole and 9 ml of TFA was stirred at room temperature for 10 min and the mixture was concentrated to 5 ml. After dilution with 50 ml of ether and 100 ml of isopropyl ether, the resulting precipitate was collected by filtration to give 1.5 g of crude trifluoroacetate of Ia (R$^2$=CH$_3$, R$^3$=OAc). It was chromatographed on a column packed with the packing of prepPAK-C$_{18}$ cartridge (400 ml, Waters), which was successively diluted with water and 20% methanol. The desired fractions eluted with 20% methanol were collected and concentrated to give a solid, which was dissolved in 100 ml of methanol and the solution was treated with active carbon and concentrated to give 10 ml. To the chilled concentrate was added ether (200 ml) and the resulting precipitate was collected by filtration, washed with ether and dried in vacuo over P$_2$O$_5$ to give 938 mg (67%) of the title compound, melting at 160° C. (grad. dec.).

IR: $\nu_{max}$ (KBr) in cm$^{-1}$ 1770, 1720, 1670, 1620, 1530, 1370, 1230, 1030.

UV: $\lambda_{max}$ (pH 7 phosphate buffer) in nm ($\epsilon$) 231 (17000), 284 (16000).

NMR: $\delta$(D$_2$O+Na$_2$CO$_3$) in ppm 2.22 (3H, s, COCH$_3$), 3.47 (1H, d, J=18 Hz, 2-H), 3.76 (1H, d, J=18 Hz, 2-H), 4.13 (3H, s, OCH$_3$), 5.39 (1H, d, J=4.5 Hz, 6-H), 5.92 (1H, d, J=4.5 Hz, 7-H), 6.36 (1H, d, J=11 Hz, CH=CH—CH$_2$), 7.14 (1H, s, thiazole-H).

Anal. Calcd. for C$_{18}$H$_{19}$N$_5$O$_7$S$_2$.½H$_2$O: C, 44.07; H, 4.11; N, 14.28; S, 13.07. Found: C, 44.29; H, 4.07; N, 13.98; S, 13.03.

(B) From VIII (R$^{2a}$=CH$_3$, R$^3$=OAc)—Diphenylmethyl 7-[(Z)-2-(tritylaminothiazol-4-yl)-2-methoxyiminoacetamido]-3-[(Z)-3-acetoxy-1-propenyl]methyl-3-4-carboxylate (1.0 g, 1.12 m moles) was dissolved in 85% formic acid (5 ml) and the solution was stirred for 2 hr at room temperature. Hydrochloric acid (0.1 ml) was added and the stirring was continued for further 2 hr. After removal of excess formic acid by evaporation, the mixture was triturated with isopropyl ether to precipitate the crude product, which was collected by filtration and purified by chromatography to give 154 mg (31%) of the title compound, which was identical with that obtained from the procedure A.

EXAMPLE 53

1-Acetoxyethyl 7-[(Z)-2-(2-aminothiazol-4-yl)-2-methoxyiminoacetamido]-3-[(Z)-3-acetoxy-1-propenyl]-3-cephem-4-carboxylate (Ib, R$^2$=CH$_3$, R$^3$=OAc, R$^4$=AX)

To a cooled and stirred solution of Ia (R$^2$=CH$_3$, R$^3$=OAc) (362 mg, 0.75 m mole) in DMF (5 ml) were added K$_2$CO$_3$ (312 mg, 2.25 m moles) and a solution of 1-acetoxyethyl bromide (501 mg, 3 m moles) in DMF (1.5 ml) in three portions at 15 minute intervals, and the mixture was stirred for additional 30 minutes. After dilution with ethyl acetate (200 ml), the solution was washed with water, a saturated NaCl solution, dried and evaporated to dryness. The oily residue was purified by chromatography on a silica gel column (Merck Kiesel gel 60, 40 g) by eluting successively with chloroform and chloroform-methanol (50:1). The fractions showing a peak at retention time 6.1 min by HPLC* were collected and evaporated to dryness to give a residue which was triturated with ether to give 236 mg (68%) of the title compound. Estimated purity 60%. This compound contained ca. 25% of Δ$^2$ isomer as an impurity. M.p. 110° C. (grad. dec.).
*HPLC (Lichrosorb RP-18, 4×300 mm, 50% acetonitrile-buffer (pH 7).

IR: $\nu_{max}$ (KBr) in cm$^{-1}$ 1780, 1760, 1740, 1670, 1610, 1530, 1370, 1230, 1070, 1030.

UV: $\lambda_{max}$ (MeOH) in nm ($\epsilon$) 268 (15000).

NMR: $\delta$(CDCl$_3$) in ppm 1.51 (3H, d, J=6 Hz, CH—CH$_3$), 2.04 (3H, s, COCH$_3$), 2.08 (3H, s, COCH$_3$), 3.03 and 3.60 (1.5H, ABq, J=18 Hz, 2-H), 4.05 (3H, s, OCH$_3$), 6.17 (0.3H, s, Δ$^2$-H), 6.26 (1H, d, J=11 Hz, CH=CH—CH$_2$).

EXAMPLE 54

Diphenylmethyl 7-amino-3-[(E)-3-acetoxy-1-propenyl]-3-cephem-4-carboxylate (XIII (E), R$^3$=H, R$^{4a}$=—CHPh$_2$)

To a solution of diphenylmethyl 7-amino-3-[(Z)-3-acetoxy-1-propenyl]-3-cephem-4-carboxylate (2.7 g, 5.8 m moles) and acetophenone (720 mg, 6 m moles) in methanol (1 L) was added 1N hydrochloric acid (6 ml). The solution was irradiated with low-pressure Hg lamp (2537 Å, 6 W) under stirring at room temperature for 22 hrs and evaporated to dryness. The residue was dissolved in ethyl acetate (300 ml) and the solution was washed with aqueous sodium bicarbonate, water, a saturated NaCl solution and dried with MgSO$_4$. After evaporation of the solvent, the residue was chromatographed on a silica gel column (Merck Kiesel gel 60, 100 g) by eluting with chloroform. The fractions showing a spot at Rf 0.45 by TLC (chloroform: methanol=30:1) were combined and concentrated to give a residue. Trituration of the residue with ether gave 910 mg (34%) of the title compound, melting at 157° C. (dec.)

The latter fraction showing a spot at 0.40 on TLC gave 583 mg (22%) of the starting Z isomer.

IR: $\nu_{max}$ (KBr) in cm$^{-1}$ 1760, 1730, 1710, 1360, 1240, 1210, 1090.

UV: $\lambda_{max}$ (MeOH) in nm ($\epsilon$) 301 (15000).

NMR: $\delta$(CDCl$_3$) in ppm 1.8 (2H, br.s, NH$_2$), 2.02 (3H, s, COCH$_3$), 3.56 (2H, s, 2-H), 4.73 (1H, d, J=4.5 Hz, 6-H), 4.95 (1H, d, J=4.5 Hz, 7-H), 6.87 (1H, d, J=16Hz, CH=CH—CH$_2$), 7.05 (1H, s, CHPh), 7.3–7.6 (10H, m, Ph).

Anal. Calcd. for C$_{25}$H$_{24}$N$_2$O$_5$S: C, 64.64; H, 5.21; N, 6.03; S, 6.72. Found: C, 64.28; H, 5.21; N, 5.88; S, 6.82.

EXAMPLE 55

Diphenylmethyl 7-[(Z)-2-(2-aminothiazol-4-yl)-2-methoxyiminoacetamido]-3-[(E)-3-acetoxy-1-propenyl]-3-cephem-4-carboxylate (XIV (E), R$^2$=CH$_3$, R$^3$=OAc, R$^{4a}$=—CHPh$_2$)

A mixture of Diphenylmethyl 7-amino-3-[(E)-3-acetoxy-1-propenyl]-3-cephem-4-carboxylate (930 mg, 2 m moles) and 1-[(Z)-2-(2-aminothiazol-4-yl)-2-methoxyiminoacetoxy]benzotriazole (954 mg, 3 m moles) in dry THF (40 ml) was stirred at room temperature for 4 hrs and the mixture was concentrated to dryness. The residue was dissolved in ethyl acetate (100 ml) and the solution was washed with an aqueous sodium bicarbonate, water, a saturated NaCl solution and dried with MgSO$_4$. After evaporation of the solvent, the residue was chromatographed on a silica gel column (Merck Kiesel gel 60, 40 g) by eluting successively with chloroform and chloroform-methanol (50%). The desired fractions were collected and evaporated to dryness and the residue was triturated with ether to give 910 mg (70%) of the title compound, melting at 110° C. (grad. dec.).

IR: $\nu_{max}$ (KBr) in cm$^{-1}$ 1780, 1730, 1680, 1610, 1530, 1380, 1220.

UV: $\lambda_{max}$ (MeOH) in nm ($\epsilon$) 297 (22000).

NMR: δ(CDCl$_3$) in ppm 1.99 (3H, s, COCH$_3$), 3.56 (2H, s, 2-H), 4.04 (3H, s, OCH$_3$), 4.52 (2H, d, J=6 Hz, CH=CH—CH$_2$), 5.08 L (1H, d, J=4.5 Hz, 6-H), 5.97 (1H, d—d, J=8 & 4.5 Hz, 7-H), 5.7–6.2 (1H, m, CH=CH—CH$_2$), 6.83 (1H, s, thiazole-H), 6.96 (1H, s, CHPh).

EXAMPLE 56

7-[(Z)-2-(2-Aminothiazol-4-yl)-2-methoxyiminoacetamido]-3-[(E)-3-acetoxy-1-propenyl]-3-cephem-4-carboxylic acid (Ia (E), R$^2$=CH$_3$, R$^3$=OAc)

A mixture of diphenylmethyl 7-[(Z)-2-(2-aminothiazol-4-yl)-2-methoxyiminoacetamido]-3-[(E)-3-acetoxy-1-propenyl]-3-cephem-4-carboxylate (870 mg, 1.34 m moles) and anisole (0.8 ml) was dissolved in 2.4 ml of trifluotoacetic acid and the solution was stirred at room temperature for 15 min. The reaction mixture was worked up and purified by a similar procedure to that described in Example 52 (procedure A) to give 429 mg (66%) of the title compound, melting at 180° C. (grad. dec.).

IR: ν$_{max}$(KBr) in cm$^{-1}$ 1770, 1730, 1670, 1630, 1530, 1370, 1240, 1030.

UV: λ$_{max}$ (pH 7 phosphate buffer) in nm (ε) 231 (17000), 292 (26000).

NMR: δ(D$_2$O+Na$_2$CO$_3$) in ppm 2.20 (3H, s, COCH$_3$), 3.75 (2H, s, 2-H), 4.10 (3H, s, OCH$_3$), 4.75 (2H, s, CH$_2$OAc), 5.32 (1H, d, J=4.5 Hz, 6-H), 5.88 (1H, d, J=4.5 Hz, 7-H), 5.9–6.3 (1H, m, CH=CH—CH$_2$), 6.73 (1H, d, J=16 Hz, CH=CH—CH$_2$), 7.09 (1H, s, thiazole-H).

EXAMPLE 57

1-Acetoxyethyl 7-[(Z)-2-(2-aminothiazol-4-yl)-2-methoxyiminoacetamido]-3-[(E)-3-acetoxy-1-propenyl]-3-cephem-4-carboxylate (Ib (E), R$^2$=CH$_3$, R$^3$=OAc R$^4$=AX)

To a stirred solution of Ia (E) (R$^2$=CH$_3$, R$^3$=OAc) (241 mg, 0.5 m mole) in dry DMF (4 ml) were added at 0°–5° C. K$_2$CO$_3$ (140 mg, 1 m mole) and a solution of 1-acetoxyethyl bromide (336 mg, 2 m moles) in DMF (2 ml) in four protions at 15-minute intervals, and the mixture was stirred at the same temperature for additional 1 hr. After dilution with ethyl acetate, the solution was washed with water and a saturated NaCl solution, dried with MgSO$_4$ and concentrated to dryness. The residue was chromatographed on a silica gel column (Merck Kiesel gel 60, 30 g) by eluting with chloroform and chloroform-methanol (50:1), successively. The desired fractions eluted with chloroform-methanol were collected and evaporated to dryness and the residue was triturated with ether to give 185 mg (65%) of the title compound, melting at 120° C. (grad. dec.).

IR: ν$_{max}$(KBr) in cm$^{-1}$ 1770, 1680, 1620, 1500, 1390, 1240, 1080, 1040.

UV: λ$_{max}$ (MeOH) in nm (ε) 232 (18000), 295 (21000).

NMR: δ(CDCl$_3$) in ppm 1.56 (3H, d, J=6 Hz, CH—CH$_3$), 2.08 (6H, s, COCH$_3$), 3.6 (2H, br-s, 2-H), 4.06 (3H, s, OCH$_3$), 5.07 (1H, d, J=4.5 Hz, 6-H), 5.39 (2H, br-s, NH$_2$), 5.7–6.4 (2H, m, CH=CHCH$_2$ & 7-H), 6.81 (1H, s, thiazole-H), 7.56 (1H, d, J=8 Hz, NH).

EXAMPLE 58

Diphenylmethyl 7-[(Z)-2-(2-tritylaminothiazol-4-yl)-2-trityloxyiminoacetamido]-3-chloromethyl-3-cephem-4-carboxylate (IV, R$^{2a}$=Tr)

To a mixture of (Z)-2-(2-tritylaminothiazol-4-yl)-2-trithyloxyiminoacetic acid* (6.71 g, 10 m moles) and 1-hydroxybenzotriazole mono hydrate (1.53 g, 11 m moles) in THF (50 ml) was added dicyclohexylcarbodiimide (2.06 g, 0 m moles) at 5° C. and the mixture was stirred for 2 hr at the same temperature and filtered to give a solution of active ether. A suspension of diphenylmethyl 7-amino-3-chloromethyl-3-cephem-4-carboxylate hydrochloride (4.51 g, 10 m moles) in ethyl acetate (50 ml) was washed with saturated NaHCO$_3$ solution (10 ml×3), water and dried. The solution was poured into the solution of active ester prepared above with stirring at 0° C. and the mixture was allowed to stand for 2 days at 5° C. After evaporation, the residue was chromatographed on a column of silica gel (silica gel 60, 100 g) and the column was eluted with CHCl$_3$-n-hexane (2:1). The fractions containing desired product was concentrated under reduced pressure. Trituration of the residue with n-hexane gave 10.0 g (94%) of the title compound as an amorphous powder.

*R. Bucourt et al., Tetrahedron, 34, 2233 (1978)

IR: ν$_{max}$ (KBr) in cm$^{-1}$ 1780, 1720, 1680, 1490.

UV: λ$_{max}$ (CH$_2$Cl$_2$) in nm (ε) 245 (23000).

NMR: δ(CDCl$_3$) in ppm 3.4 (2H, ABq, J=12 Hz, 2-H), 5.02 (1H, d, J=4 Hz, 6-H), 6.01 (1H, d—d, J=4 and 6 Hz, 7-H), 6.45 (1H, s, thiazole-H), 7.00 (1H, s, CHPh$_2$), 7.1–7.7 (40H, phenyl-H).

EXAMPLE 59

Diphenylmethyl 7-[(Z)-2-(2-tritylaminothiazol-4-yl)-2-trityloxyiminoacetamido]-3-(triphenylphosphoranylidene)-methyl-3-cephem-4-carboxylate (VII, R$^{2a}$=Tr)

A mixture of diphenylmethyl 7-[(Z)-2-(2-tritylaminothiazol-4-yl)-2-trityloxyiminoacetamido]-3-chloromethyl-3-cephem-4-carboxylate (9.9 g, 9.3 m moles) and NaI (11 g, 73 m moles) in acetone (100 ml) was stirred for 30 min at room temperature and concentrated under reduced pressure. The residue was diluted with ethyl acetate (100 ml), and the mixture was washed with aqueous 10% Na$_2$S$_2$O$_3$ solution (50 ml×2) and water. To the mixture was added triphenylphosphine (3.93 g, 15 m moles) and the mixture was stirred for 3 hr at room temperature. After evaporation, the residue was triturated with isopropyl ether and the precipitate was collected by filtration to give the phosphonium salt (14.2 g). It was dissolved in CH$_2$Cl$_2$ (100 ml) and the solution was washed with 1N NaOH (ca. 50 ml) until the phosphonium salt was completely converted into the ylide by monitoring with TLC (Merck silica gel 60 F$_{254}$, CHCl$_3$-MeOH, 10:1). The organic layer was separated, washed with water and concentrated under reduced pressure. The residue was triturated with isopropyl ether to give 12.0 g (94%) of the title compound.

IR: ν$_{max}$ (KBr) in cm$^{-1}$ 1760, 1740, 1650, 1480.

UV: λ$_{max}$ (CH$_2$Cl$_2$) in nm (ε) 310 (9200), 388 (16200).

EXAMPLE 60

Diphenylmethyl 7-[(Z)-2-(2-tritylaminothiazol-4-yl)-2-trityloxyiminoacetamido]-3-[(Z)-3-acetoxy-1-propenyl]-3-cephem-4-carboxylate (VIII, $R^{2a}$=Tr, $R^3$=OAc)

A mixture of diphenylmethyl 7-[(Z)-2-(tritylaminothiazol-4-yl)-2-trityloxyiminoacetamido]-3-(triphenylphosphoranylidene)methyl-3-cephem-4-carboxylate (2.58 g, 2 m moles) and acetoxyacetaldehyde* (612 mg, 3 m moles) in dichloromethane (10 ml) was stirred overnight at room temperature and concentrated under reduced pressure. The residue was chromatographed on a column of silica gel (Merck silica gel 60, 50 g) and the column was eluted with toluene-ethyl acetate (9:1). Evaporation of the fractions containing the desired product gave 1.0 g (45%) of the title compound.
*J. Corbet and C. Benezra, J. Org. Chem., 46, 1141 (1981)

IR: $\nu_{max}$ (KBr) in cm$^{-1}$ 1780, 1730, 1680, 1520, 1220.
UV: $\lambda_{max}$ (CH$_2$Cl$_2$) in nm ($\epsilon$) 305 (12200).
NMR: $\delta$(CDCl$_3$) in ppm 2.00 (3H, s, COCH$_3$), 3.20 (2H, ABq, J=18 Hz, 2-H), 5.1 (1H, d, J=4 Hz, 6-H), 6.20 (1H, d, J=11 Hz, =CH), 6.48 (1H, s, thiazole-H), 6.95 (1H, s, CHPh$_2$), 7.1-7.6 (40H, phenyl-H).

EXAMPLE 61

7-[(Z)-2-(2-Aminothiazol-4-yl)-2-hydroxyiminoacetamido]-3-[(Z)-3-acetoxy-1propenyl]-3-cephem-4-carboxylic acid (Ia, $R^2$=H, $R^3$=OAc)

A mixture of diphenylmethyl 7-[(Z)-2-(2-tritylaminothiazol-4-yl)-2-trityloxyiminoacetamido]-3-[(Z)-3-acetoxy-1-propenyl]-3-cephem-4-carboxylate (3.29 g, 2.94 m moles) and 85% formic acid (15 ml) was stirred for 2 hr at room temperature. To the solution was added conc. hydrochloric acid (0.6 ml) and the mixture was stirred for 2 hr. After evaporation of the solvent, the residue was triturated with isopropyl ether to give 1.2 g of a crude product, which was chromatographed on a column of C18-silica gel (20 mm×200 mm) by eluting with 20% MeOH. The fractions containing the desired product were combined and concentrated to a small volume under reduced pressure. Lyophilization of the concentrate afforded 412 mg (30%) of the title compound, melting at 180° C. (dec.). Estimated purity 60%.

IR: $\nu_{max}$ (KBr) in cm$^{-1}$ 1760, 1620, 1530, 1370, 1240.
UV: $\lambda_{max}$ (pH 7 phosphate buffer) in nm ($\epsilon$) 279 (15300).
NMR: $\delta$(DMSO-d$_6$) in ppm 2.00 (3H, s, COCH$_3$), 4.50 (2H, d, J=8 Hz, CH$_2$O), 5.15 (1H, d, J=4 Hz, 6-H), 6.30 (1H, d, J=12 Hz, =CH—), 6.65 (1H, s, thiazol-H), 7.00 (2H, s, NH$_2$), 9.40 (1H, d, J=8 Hz, 7-CONH), 11.30 (1H, s, =N—OH).

EXAMPLE 62

1-Acetoxyethyl 7-[(Z)-2-(2-aminothiazol-4-yl)-2-hydroxyiminoacetamido]-3-[(Z)-3-acetoxy-1-propenyl]-3-cephem-4-carboxylate (Ib, $R^2$=H, $R^3$=OAc, $R^4$=AX)

To a stirred solution of Ia ($R^2$=H, $R^3$=OAc) (280 mg, 0.6 m mole) in dry DMF (2 ml) was added at −5° C. Na$_2$CO$_3$ (105 mg, 1 m mole) and a solution of 1-acetoxyethyl bromide (396 mg, 2.37 m moles) in DMF (2 ml) in three portions at 20-minute intervals and the mixture was stirred for additional 10 minutes. After dilution with ethyl acetate, the solution was washed with water and concentrated under reduced pressure. Trituration of the residue with isopropyl ether gave 195 mg of the crude product, which was chromatographed on a column of silica gel (25 g). The column was eluted with chloroform containing 1-2% methanol and the fractions containing the desired product were combined and evaporated under reduced pressure. Trituration of the residue with isopropyl ether gave 75 mg (23%) of the product, melting at 100° C. (dec.). Estimated purity 70%.

IR: $\nu_{max}$ (KBr) in cm$^{-1}$ 1780, 1730, 1670, 1530, 1380, 1240.
UV: $\lambda_{max}$ (CH$_2$Cl$_2$) in nm ($\epsilon$) 249 (17300).
NMR: $\delta$(CDCl$_3$) in ppm 1.0 (3H, d, J=5 Hz, CH—CH$_3$), 2.03 (3H, s, COCH$_3$), 2.05 (3H, s, COCH$_3$), 5.10 (1H, d, J=4 Hz, 6-H), 6.30 (1H, d, J=12 Hz, =CH—), 6.95 (1H, s, thiazole-H).

What is claimed is:
1. A compound of the formula wherein
$R^1$ is hydrogen or a conventional amino-protecting group,
$R^2$ is hydrogen, or alkanoyl having 2 to 4 carbon atoms,
$R^3$ is hydrogen, or lower alkanoyloxy having 2 to 3 carbon atoms, and
$R^4$ is hydrogen, or a physiologically hydrolyzable ester group with provision that when $R^4$ is hydrogen at least one of $R^2$ and $R^3$ is other than hydrogen.

2. A compound of the formula wherein
$R^1$ is hydrogen or a conventional amino-protecting group,
$R^2$ is hydrogen, or alkanoyl having 2 to 4 carbon atoms,
$R^2$ is hydrogen, or lower alkanoyloxy having 2 to 3 carbon atoms, and
$R^4$ is hydrogen, or a physiologically hydrolyzable ester group selected from pivaloyloxymethyl,1-(acetoxy)ethyl, or acetoxymethyl with provision that when $R^4$ is hydrogen at least one of $R^2$ and $R^3$ is other than hydrogen.

3. The compound of claim 2 wherein $R^1$ is hydrogen and $R^2$ is hydrogen, or acetyl.

4. The compound of claim 3 wherein $R^2$ is hydrogen.

5. The compound of claim 4 wherein $R^3$ is hydrogen.

6. The compound of claim 5 wherein $R^4$ is acetoxymethyl.

7. The compound of claim 6 which is acetoxymethyl 7$\beta$-[(Z)-2-(2-aminothiazol-4-yl)-2-(hydroxyimino)acetamido]-3-[(Z)-prop-1-en-1-yl]-3-cephem-4-carboxylate.

8. The compound of claim 6 which is acetoxymethyl 7β-[(Z)-2-(2-aminothiazol-4-yl)-2-(hydroxyimino)acetamido]-3-[(E)-prop-1-en-1-yl]-3-cephem-4-carboxylate.

9. The compound of claim 5 wherein R⁴ is 1-acetoxyethyl.

10. The compound of claim 9 which is 1-acetoxyethyl 7β-[(Z)-2-(2-aminothiazol-4-yl)-2-(hydroxyimino)acetamido]-3-[(Z)-prop-1-en-1-yl]-3-cephem-4-carboxylate.

11. The compound of claim 9 which is 1-acetoxyethyl 7β-[(Z)-2-(2-aminothiazol-4-yl)-2-(hydroxyimino)acetamido]-3-[(E)-prop-1-en-1-yl]-3-cephem-4-carboxylate.

12. The compound of claim 5 wherein R⁴ is pivaloyloxymethyl.

13. The compound of claim 12 which is pivaloyloxymethyl 7β-[(Z)-2-(2-aminothiazol-4-yl)-2-(hydroxyimino)acetamido]-3-[(Z)-prop-1-en-1-yl]-3-cephem-4-carboxylate.

14. The compound of claim 12 which is pivaloyloxymethyl 7β-[(Z)-2-(2-aminothiazol-4-yl)-2-(hydroxyimino)acetamido]-3-[(E)-prop-1-en-1-yl]-3-cephem-4-carboxylate.

15. The compound of claim 4 wherein R³ is acetoxy.

16. The compound of claim 15 wherein R⁴ is hydrogen.

17. The compound of claim 16 which is 7β-[(Z)-2-(2-aminothiazol-4-yl)-2-(hydroxyimino)acetamido]-3-[(Z)-3-acetoxyprop-1-en-1-yl]-3-cephem-4-carboxylic acid.

18. The compound of claim 16 which is 7β[(Z)-2-(2-aminothiazol-4-yl)-2-(hydroxyimino)acetamido]-3-[(E)-3-acetoxyprop-1-en-1-yl]-3-cephem-4-carboxylic acid.

19. The compound of claim 15 wherein R⁴ is acetoxymethyl.

20. The compound of claim 19 which is acetoxymethyl 7β-[(Z)-2-(2-aminothiazol-4-yl)-2-(hydroxyimino)acetamido]-3-[(Z)-3-acetoxyprop-1-en-1-yl]-3-cephem-4-carboxylate.

21. The compound of claim 19 which is acetoxymethyl 7β-[(Z)-2-(2-aminothiazol-4-yl)-2-(hydroxyimino)acetamido]-3-[(E)-3-acetoxyprop-1-en-1-yl]-3-cephem-4-carboxylate.

22. The compound of claim 15 wherein R⁴ is 1-acetoxyethyl.

23. The compound of claim 22 which is 1-acetoxyethyl 7β-[(Z)-2-(2-aminothiazol-4-yl)-2-(hydroxyimino)acetamido]-3-[(Z)-3-acetoxyprop-1-en-1-yl]-3-cephem-4-carboxylate.

24. The compound of claim 22 which is 1-acetoxyethyl 7β-[(Z)-2-(2-aminothiazol-4-yl)-2-(hydroxyimino)acetamido]-3-[(E)-3-acetoxyprop-1-en-1-yl]-3-cephem-4-carboxylate.

25. The compound of claim 15 wherein R⁴ is pivaloyloxymethyl.

26. The compound of claim 25 which is pivaloyloxymethyl 7β-[(Z)-2-(2-aminothiazol-4-yl)-2-(hydroxyimino)acetamido]-3-[(Z)-3-acetoxyprop-1-en-1-yl]-3-cephem-4-carboxylate.

27. The compound of claim 25 which is pivaloyloxymethyl 7β-[(Z)-2-(2-aminothiazol-4-yl)-2-(hydroxyimino)acetamido]-3-[(E)-3-acetoxyprop-1-en-1-yl]-3-cephem-4-carboxylate.

28. The compound of claim 3 wherein R² is acetyl.

29. The compound of claim 28 wherein R³ is hydrogen.

30. The compound of claim 29 wherein R⁴ is hydrogen.

31. The compound of claim 30 which is 7β-[(Z)-2-(2-aminothiazol-4-yl)-2-(acetoxyimino)acetamido]-3-[(Z)-prop-1-en-1-yl]-3-cephem-4-carboxylic acid.

32. The compound of claim 30 which is 7β-[(Z)-2-(2-aminothiazol-4-yl)-2-(acetoxyimino)acetamido]-3-[(E)-prop-1-en-1-yl]-3-cephem-4-carboxylic acid.

33. The compound of claim 29 wherein R⁴ is acetoxymethyl.

34. The compound of claim 33 which is acetoxymethyl 7β-[(Z)-2-(2-aminothiazol-4-yl)-2-(acetoxyimino)acetoamido]-3-[(Z)-prop-1-en-1-yl]-3-cephem-4-carboxylate.

35. The compound of claim 33 which is acetoxymethyl 7β-[(Z)-2-(2-aminothiazol-4-yl)-2-(acetoxyimino)acetamido]-3-[(E)-prop-1-en-1-yl]-3-cephem-4-carboxylate.

36. The compound of claim 29 wherein R⁴ is 1-acetoxyethyl.

37. The compound of claim 36 which is 1-acetoxyethyl 7β-[(Z)-2-(2-aminothiazol-4-yl)-2-(acetoxyimino)acetamido]-3-[(Z)-prop-1-en-1-yl]-3-cephem-4-carboxylate.

38. The compound of claim 36 which is 1-acetoxyethyl 7β-[(Z)-2-(2-aminothiazol-4-yl)-2-(acetoxyimino)acetamido]-3-[(E)-prop-1-en-1-yl]-3-cephem-4-carboxylate.

39. The compound of claim 29 wherein R⁴ is pivaloyloxymethyl.

40. The compound of claim 39 which is pivaloyloxymethyl 7β-[(Z)-2-(2-aminothiazol-4-yl)-2-(acetoxyimino)acetamido]-3-[(Z)-prop-1-en-1-yl]-3-cephem-4-carboxylate.

41. The compound of claim 39 which is pivaloyloxymethyl 7β-[(Z)-2-(2-aminothiazol-4-yl)-2-(acetoxyimino)acetamido]-3-[(E)-prop-1-en-1-yl]-3-cephem-4-carboxylate.

42. The compound of claim 28 wherein R³ is acetoxy.

43. The compound of claim 42 wherein R⁴ is hydrogen.

44. The compound of claim 43 which is 7β-[(Z)-2-(2-aminothiazol-4-yl)-2-(acetoxyimino)acetamido]-3-[(Z)-3-acetoxyprop-1-en-1-yl]-3-cephem-4-carboxylic acid.

45. The compound of claim 43 which is 7β-[(Z)-2-(2-aminothiazol-4-yl)-2-(acetoxyimino)acetamido]-3-[(E)-3-acetoxyprop-1-en-1-yl]-3-cephem-4-carboxylic acid.

46. The compound of claim 42 wherein R⁴ is acetoxymethyl.

47. The compound of claim 46 which is acetoxymethyl 7β-[(Z)-2-(2-aminothiazol-4-yl)-2-(acetoxyimino)acetamido]-3-[(Z)-3-acetoxyprop-1-en-1-yl]-3-cephem-4-carboxylate.

48. The compound of claim 46 which is acetoxymethyl 7β-[(Z)-2-(2-aminothiazol-4-yl)-2-(acetoxyimino)acetamido]-3-[(E)-3-acetoxyprop-1-en-1-yl]-3-cephem-4-carboxylate.

49. The compound of claim 42 wherein R⁴ is 1-acetoxyethyl.

50. The compound of claim 49 which is 1-acetoxyethyl 7β-[(Z)-2-(2-aminothiazol-4-yl)-2-(acetoxyimino)acetamido]-3-[(Z)-3-acetoxyprop-1-en-1-yl]-3-cephem-4-carboxylate.

51. The compound of claim 49 which is 1-acetoxyethyl 7β-[(Z)-2-(2-aminothiazol-4-yl)-2-(acetoxyimino)acetamido]-3-[(E)-3-acetoxyprop-1-en-1-yl]-3-cephem-4-carboxylate.

52. The compound of claim 42 wherein $R^4$ is pivaloyloxymethyl.

53. The compound of claim 52 which is pivaloyloxymethyl 7β-[(Z)-2-(2-aminothiazol-4-yl)-2-(acetoxyimino)acetamido]-3-[(Z)-3-acetoxyprop-1-en-1-yl]-3-cephem-4-carboxylate.

54. The compound of claim 52 which is pivaloyloxymethyl 7β-[(Z)-2-(2-aminothiazol-4-yl)-2-(acetoxyimino)acetamido]-3-[(E)-3-acetoxyprop-1-en-1-yl]-3-cephem-4-carboxylate.

55. The compound of claim 1 wherein $R^4$ is 5-methyl-2-oxo-1,3-dioxolen-4-ylmethyl.

56. The compound of claim 55 which is 5-methyl-2-oxo-1,3-dioxolen-4-ylmethyl 7β-[(Z)-2-(2-aminothiazol-4-yl)-2-(acetoxyimino)acetamido]-3-[(Z)-prop-1-en-1-yl]-3-cephem-4-carboxylate.

57. The compound of claim 55 which is 5-methyl-2-oxo-1,3-dioxolen-4-ylmethyl 7β-[(Z)-2-(2-aminothiazol-4-yl)-2-(acetoxyimino)acetamido]-3-[(E)-prop-1-en-1-yl]-3-cephem-4-carboxylate.

58. The compound of claim 1 wherein $R^4$ is 5-methyl-2-oxo-1,3-dioxolen-4-ylmethyl.

59. The compound of claim 58 which is 5-methyl-2-oxo-1,3-dioxolen-4-ylmethyl 7β-[(Z)-2-(2-aminothiazol-4-yl)-2-(acetoxyimino)acetamido]-3-[(Z)-3-acetoxyprop-1-en-1-yl]-3-cephem-4-carboxylate.

60. The compound of claim 58 which is 5-methyl-2-oxo-1,3-dioxolen-4-ylmethyl 7β-[(Z)-2-(2-aminothiazol-4-yl)-2-(acetoxyimino)acetamido]-3-[(E)-3-acetoxyprop-1-en-1-yl]-3-cephem-4-carboxylate.

61. A pharmaceutical antibacterial composition comprising an effective amount of a compound of claim 3 in association with a pharmaceutically acceptable substantially nontoxic carrier or excipient.

62. A method for the treatment of a bacterial infection in a mammal caused by an organism sensitive to a substance claimed in claim 3, which comprises administering an antibacterially effective non-toxic dose of one of said substances to the infected mammal on a repetitive dosage regimen for a treatment period of sufficient duration to mitigate said infection.

* * * * *

UNITED STATES PATENT AND TRADEMARK OFFICE
CERTIFICATE OF CORRECTION

PATENT NO. : 4,708,955
DATED : November 24, 1987
INVENTOR(S) : Seiji Iimura, et al It is certified that error appears in the above-identified patent and that said Letters Patent is hereby corrected as shown below:

Claim 55, line 1, "Claim 1" should read -- Claim 29 --.

Claim 58, line 1 "Claim 1" should read -- Claim 42 --.

Signed and Sealed this

Twenty-first Day of June, 1988

Attest:

DONALD J. QUIGG

Attesting Officer Commissioner of Patents and Trademarks